(12) United States Patent
Nakatani

(10) Patent No.: US 7,067,646 B2
(45) Date of Patent: Jun. 27, 2006

(54) METHODS AND COMPOSITIONS FOR MODULATING TUMOR SUPPRESSION

(75) Inventor: Yoshihiro Nakatani, Boston, MA (US)

(73) Assignee: Dana Farber Cancer Institute, Boston, MA (US)

(*) Notice: Subject to any disclaimer, the term of this patent is extended or adjusted under 35 U.S.C. 154(b) by 541 days.

(21) Appl. No.: 10/107,521

(22) Filed: Mar. 25, 2002

(65) Prior Publication Data
US 2003/0166230 A1    Sep. 4, 2003

Related U.S. Application Data

(60) Provisional application No. 60/278,245, filed on Mar. 23, 2001, provisional application No. 60/278,244, filed on Mar. 23, 2001.

(51) Int. Cl.
*C07H 19/00* (2006.01)
*C07H 21/04* (2006.01)

(52) U.S. Cl. ............... 536/23.5; 536/23.1; 536/23.5; 435/320.1

(58) Field of Classification Search ............... 536/23.1, 536/23.5; 435/320.1
See application file for complete search history.

(56) References Cited

U.S. PATENT DOCUMENTS 6,569,622 B1* 5/2003 Arthur et al. ............... 435/6

FOREIGN PATENT DOCUMENTS

| WO | WO 99/60164 | 2/1999 |
|---|---|---|
| WO | WO 02/077019 | 10/2002 |
| WO | WO 02/086122 | 10/2002 |

OTHER PUBLICATIONS

Friend, et al., A human DNA segment with properties of the gene that predisposes to retinoblastoma and osteosarcoma, *Nature*, Oct. 16, 1986, pp. 643-646, vol. 323.
Fung, et al., Structural Evidence for the Authenticity of the Human Retinoblastoma Gene, *Science*, Jun. 26, 1987, pp. 1657-1661, vol. 236.
Ono, et al., The Structure, Expression, and Properties of Additional Members of the Protein Kinase C Family, *The Journal of Biological Chemistry*, May 15, 1988: pp. 6927-6932; vol. 263; No. 14.
Altschul, et al., Basic Local Alignment Search tool, *J. Mol. Biol.*, 1990, pp. 403-410: vol. 215.
Kaye, et al., A single amino acid substitution results in a retinoblastoma protein defective in phosphorylation and oncoprotein binding, *Proc. Natl. Acad. Sci. USA*, Sep. 1990, pp. 6922-6926, vol. 87.
Yang, Gene Transfer into Mammalian Somatic Cells In Vivo, *Critical Reviews in Biotechnology*, 1992, pp. 335-356, vol. 12, No. 4.

Huang, et al., The Retinoblastoma Protein Region Required for Interaction with the E2F Transcription Factor Includes the T/E1A Binding and Carboxy-Terminal Sequences, *DNA and Cell Biology*, 1992, pp. 539-548, vol. 11, No. 7.
Lee, et al., Mice deficient for Rb are nonviable and show defects in neurogenesis and haematopoiesis, *Nature*, Sep. 24, 1992, pp. 288-294, vol. 359.
Jacks, et al., Effects of an *Rb* mutation in the mouse, *Nature*, Sep. 24, 1992, pp. 295-300. vol. 359.
Clarke, et al., Requirement for a functional *Rb-1* gene in murine development. *Nature*, Sep. 24, 1992, pp. 328-330, vol. 359.
Kratzke, et al., Functional Analysis at the $Cys^{706}$ Residue of the Retinoblastoma Protein: *The Journal of Biological Chemistry*; Dec. 25, 1992: pp. 25998-26003: vol. 267: No. 36.
Goodrich, et al., Molecular characterization of the retinoblastoma susceptibility gene, *Biochimica et Biophysica Acta*, 1993, pp. 43-61.
Kratzke, et al., Partial inactivation of the RB product in a family with incomplete penetrance of familial retinoblastoma and benign retinal tumors, *Oncogene*, 1994, pp. 1321-1326, vol. 9.
Neuman, et al., Transcription of the E2F-1 Gene Is Rendered Cell Cycle Dependent by E2F DNA-Binding Sites within Its Promoter, *Molecular and Cellular Biology*, Oct. 1994, pp. 6607-6615, vol. 14, No. 10.
Weinberg, The Retinoblastoma Protein and Cell Cycle Control: *Cell*; May 5, 1995; pp. 323-330; vol. 81.
Jeffrey, et al., Mechanism of CDK activation revealed by the structure of a cyclinA-CDK2 complex. *Nature*, Jul. 27, 1995, pp. 313-320, vol. 376.
Bagby, et al., Solution Structure of the C-Terminal Core Domain of Human TFIIB: Similarity to cyclin A and Interaction with TATA-Binding Protein: *Cell*; Sep. 8, 1995; pp. 857-867, vol. 82.

(Continued)

*Primary Examiner*—Jeffrey Siew
*Assistant Examiner*—Brandon Fetterolf
(74) *Attorney, Agent, or Firm*—Fish & Richardson P.C.

(57) ABSTRACT

The purification of native RB (retinoblastoma) as a complex, including P107, P130, and a 600 kDa subunit, termed MTAF600 (microtubule associated factor 600) is described. MTAF600 binds to RB regardless of the phosphorylation status of RB, and binds to RB without disrupting the interaction between RB and E2F. It is further shown that E2F and DP proteins co-purified with MTAF600 and RB, such that hypophosphorylated RB may gain access to E2F as a complex with MTAF600. In addition, MTAF600 binds to microtubules and plays a role in active repression of E2F-responsive genes, cell cycle arrest, and genomic stability. The sequence of MTAF600 is described herein, along with its binding properties to proteins such as RB and microtubules, and its sequence homology. Further, methods and reagents for assaying the presence of MTAF600 or mutants thereof, pharmaceutical formulations, and methods for treating disease are also described.

7 Claims, 30 Drawing Sheets

OTHER PUBLICATIONS

Nikolov, et al., Crystal structure of a TFIIB-TBP-TATA-element ternary complex, *Nature*, Sep. 14, 1995, pp. 119-128, vol. 377.

Zalvide, et al., Role of pRb-Related Proteins in Simian Virus 40 Large-T-Antigen-Mediated Transformation, *Molecular and Cellular Biology*, Oct. 1995, pp. 5800-5810, vol. 15, No. 10.

Cobrinik, et al., Shared role of the pRB-related p130 and p107 proteins in limb development, *Genes & Development*, 1996, pp. 1633-1644, vol. 10.

Sherr, Cancer Cell Cycles, *Science*, 1996. pp. 1672-1677, vol. 274, <http://www.sciencemag.org/cgi/content/full/274/5293/1672>.

Shan, et al., Disruption of RB/E2F-1 interaction by single point mutations in E2F-1 enhances S-phase entry and apoptosis, *Proc. Natl. Acad. Sci. USA*, Jan. 1996, pp. 679-684, vol. 93.

Richards, et al., Mutations in the *Drosophila pushover* Gene Confer Increased Neuronal Excitability and Spontaneous Synaptic Vesicle Fusion, *Genetics*, Apr. 1996, pp. 1215-1223, vol. 142.

Flint, et al., Viral Transactivating Proteins, *Annu. Rev. Genet*, 1997, pp. 177-212, vol. 31.

Seki, et al., Characterization of cDNA clones in size-fractionated cDNA libraries from human brain.

Allen, et al., Distinct mechanisms of nuclear accumulation regulate the functional consequence of E2F transcription factors, *Journal of Cell Science*, 1997, pp. 2819-2831, vol. 110.

Altschul, et al., Gapped Blast and PSI-Blast: a new generation of protein database search programs, *Nucleic Acids Research*, 1997, pp. 3389-3402, vol. 25, No. 17.

Jiang, et al., The retinoblastoma gene family is differentially expressed during embryogenesis. *Oncongene*, 1997, pp. 1789-1797, vol. 14.

Verona, et al., E2F Activity Is Regulated by Cell Cycle-Dependent Changes in Subcellular Localization, *Molecular and Cellular Biology*, Dec. 1997. pp. 7268-7282, vol. 17, No. 12.

Mittnacht, Control of pRB phosphorylation, *Current Opinion in Genetics & Development*, 1998, pp. 21-27, vol. 8.

Sellers, et al. Stable binding to E2F is not required for the retinoblastoma protein to activate transcription, promote differentiation, and suppress tumor cell growth, *Genes & Development*, 1998, pp. 95-106, vol. 12.

Dyson, The regulation of E2F by pRB-family proteins, *Genes & Development*, 1998, pp. 2245-2262, vol. 12.

Yilmaz, et al., Abstract: Twelve novel RBI gene mutations in patients with hereditary retinoblastomas. Mutations in brief No. 206. Online., *Hum Mutat*, 1998, p. 434, vol. 12, No. 6 <http://www.ncbi.nlm.nih.gov/entrez/query.fcgi?cmd=Retrieve&db=PubMed&list_uids=1 0 . . . >.

Cartwright, et al., E2F-6: a novel member of the E2F family is an inhibitor of E2F-depend transcription, *Oncogene*, 1998, pp. 611-623, vol. 17.

Brehm, et al., Retinoblastoma protein recruits histone deacetylase to repress transcription, *Nature*, Feb. 5, 1998, pp. 597-601, vol. 391.

Magnaghi-Jaulin, et al., Retinoblastoma protein represses transcription by recuiting a histone deacetylase, *Nature*, Feb. 5, 1998. pp. 601-605, vol. 391.

Luo, et al., Rb Interacts with Histone Deacetylase to Repress Transcription: *Cell*. Feb. 20, 1998: pp. 463-473: vol. 92.

Trimarchi, et al., E2F-6, a member of the E2F family that can behave as a transcriptional repressor. *Proc. Natl. Acad. Sci. USA*, Mar. 1998, pp. 2850-2855, vol. 95.

Mulligan, et al., The retinoblastoma gene family: cousins with overlapping interests, *TIG*, Jun. 1998, pp. 223-229 vol. 14. No. 6.

Ogryzko, et al., Histone-like TAFs within the PCAF Histone Acetylase Complex: *Cell*; Jul. 10, 1998: pp. 35-44;vol. 94.

Gaubatz, et al., Unusual proliferation arrest and transcriptional control properties of a newly discovered E2F family member, E2F-6; *Proc Natl. Acad. Sci. USA*; Aug. 1998; pp. 9190-9195; vol. 95.

Ferreira, et al., The three members of the pocket proteins family share the ability to repress E2F activity through recruitment of a histone deacetylase, *Proc. Natl. Acad. Sci. USA*, Sep. 1998, pp. 10493-10498, vol. 95.

Xu, et al., Retinal Targets for Calmodulin Include Proteins Implicated in Synaptic Transmission, *The Journal of Biological Chemistry*; Nov. 20, 1998; pp. 31297-31307; vol. 273, No. 47.

Black, et al., Regulation of E2F: a family of transcription factors involved in proliferation control: *Gene*, 1999, pp. 281-302, 237.

Kingston, et al., A TP-dependent remodeling and acetylation as regulators of chromatin fluidity. *Genes & Development*, 1999. pp. 2339-2352, vol. 13.

Lohman, RBI Gene Mutations in Retinoblastoma, *Human Mutation*, 1999, pp. 283-288, vol. 14.

Sekelsky, et al., Identification of Novel Drosophila Meiotic Genes Recovered in a P-Element Screen, *Genetics*, Jun. 1999, pp. 529-542, vol. 152.

Harbour, et al., Chromatin remodeling and Rb activity, *Current Opinion in Cell Biology*, 2000, pp. 685-689, vol. 12.

Sage, et al., Targeted disruption of the three Rb-related genes leads to loss of $G_1$ control and immortalization, *Genes & Development*, 2000, pp. 3037-3050, vol. 14.

Dannenberg, et al., Ablation of the Retinoblastoma gene family deregulates $G_1$ control causing immortalization and increased cell turnover under growth-restricting conditions, *Genes & Development*, 2000, pp. 3051-3064, vol. 14.

Fuks, et al., DNA methyltransferase Dnmt 1 associates with histone deacetylase activity, *nature genetics*, Jan. 2000, pp. 88-91, vol. 24.

Zhang, et al., Exit from G1 and S Phase of the Cell Cycle Is Regulated by Repressor Complexes Containing HDAC-Rb-hSWI/SNF and Rb-hSWI/SNF; *Cell*; Mar. 31, 2000: pp. 79-89; vol. 101.

Dick, et al., Mutagenesis of the pRB Pocket Reveals that Cell Cycle Arrest Functions Are Separable from Binding to Viral Oncoproteins, *Molecular and Cellular Biology*, May 2000, pp. 3715-3727, vol. 20, No. 10.

Robertson, et al., DNMTI forms a complex with Rb. E2FI and HDAC1 and represses transcription from E2F-responsive promoters, *nature genetics*, Jul. 2000, pp. 338-342, vol. 25.

Dahiya, et al., Role of the LXCXE Binding Site in Rb Function, *Molecular and Cellular Biology*, Sep. 2000, pp. 6799-6805, vol. 20, No. 18.

Classon, et al., Combinatorial roles for pRB. p107, and p130 in E2F-mediated cell cycle control; *PNAS*; Sep. 26, 2000; pp. 10820-10825; vol. 97, No. 20.

Gil, et al., BIG: a calossin-like protein required for polar auxin transport in *Arabidopsis, Genes & Development*, Jun. 4, 2001, pp. 1985-1997, vol. 15.

Zamore, RNA interference: listening to the sound of silence, *Nature Structural Biology*, Sep. 2001, pp. 746-750, vol. 8, No. 9.

Luschnig, Auxin transport: Why Plants like to think BIG, *Current Biology*, 2001, pp. R831-R833, vol. 11.

Nakatani, Accession No. AAY53675, Database Genbank, pct-us-02-09382-1.rag.

Nakatani, Accession No. T00076 and T08689. Database Genbank, pct-us-02-09382-1.rpr.

International Search Report mailed on Sep. 12, 2002 for International Application No. PCT/US02/09382 filed Mar. 25, 2002.

GenBank Accession No.:075050, (XP002311873), Seki et al., Nov. 1, 1998.

GenBank Accession No.: AF348492, (XP002311874), Konishi et al., Mar. 6, 2002.

Reeck et al., "Homology in Proteins and Nucleic Acids: A Terminology Muddle and a Way out of it" Cell, Cell Press, vol. 50:667, 1987.

Wang, J., "Retinoblastoma protein in growth suppression and death protection" Curr. Opin. In Gen. and Dev. vol. 7(1):39-45, 1997.

Weaver et al., "A Crustacean Neuronal Cytoskeletal Protein with Characteristics of Neurofilaments and . . . " J. of Comparative Neurol. 320:110-120, 1992.

* cited by examiner

DEDUCED AMINO ACID SEQUENCE OF MTAF600

```
   1 MATSGGERAA AAAPAPGTPA TGADTTPGWE VAVPPLLSAS ISAFEMKELP QLVASVIESE SEILHHEKQY EPFYSSFVAL STHYITTVCS LIPRNQLQSV
 101 AACKVLIEF SLLRLENPDE ACAVSQKHLI LLIKGLCTSC SRLDRTEIIT PTAWMKSAKL PQTVKTLSDV EDQKELASPV SPELRQKEVQ MNFLNQLTSV
 201 FNPRTVASQP ISTQTLVEGE NDEQSSTTQA SAIKTKNVFI AQNVASLQEL GGSEKLLRVC LNLPYFLRYI NRFQDAVLAN SFFIMPATVA DATAVRNGFH
 301 SLVIDVTMAL DTLSLPVLEP LNPSRLQDVT VLSLSCLVAG VSVATCMAIL HVGSAQQVRT GSTSSKEDDY ESDAATIVQK CLEIYDMIGQ AISSSRRAGG
 401 EHYQNFQLLG AWCLLNSLFL ILMLSPTALA DKGKEKDPLA ALRVRDILSR TKEGVGSPKL GPGKHQGFG VLSVILANHA IKLLTSLPQD LQVEALHKGW
 501 ETDGPPAALS IMAQSTSIQR IQRLIDSVPL MNLLLTLLST SYRKACVIQR QRKGSMSSDA SASTDSNTYI EDDFSSTEED SSQDDDSEPI LGQWFEETIS
 601 PSKEKAAPPP PPPPPLESS PRVKSPSKQA PGEKGNILAS RKDPELFLGL ASNILNFITS SMLNSRNNFI RNYLSVSLSE HHMATLASII KEVDKDGLKG
 701 SSDEEFAAAL YBFNHSLVTS DLQSPNLQNT LLQQLGVAPF SEGPWPLYIH PQSLSVLSRL LLIWQHKASA QGDPDVPECL KVMDRFLSTM KQMALQGVVP
 801 SETEDLNVEH LQMLLLIFHN FTETGRRAIL SLFVQIIQEL SVNMDAQMRF VPLILARLIL IFDYLLHQYS KAPVLFEQV QHNLLSPPFG WASGSQDSNS
 901 RRATTPLYHG FKEVEENMSK HFSSDAVPHP RFYCVLSPEA SEDDLNRLDS VACDVLFSKL VKYDELYAAL TALLAAGSQL DTVRRKENKN VTALBACALQ
1001 YYFLILMRIL GILPPSKTYI NQLSMNSPEM SECDILHTLR WSSRLRISSY VNWIKDHLIK QGMKAEHASS LLELASTTKC SSVKIDVEIV EEYPARQISS
1101 FCSIDCTTIL QLHEIPSLQS IYPLDAAISK VQVSLDEHFS KMAAETDPHK SSEITKNLLP ATLQLIDTYA SFTRAYLLQN FNEBGTTEKP SKEKLQGFAA
1201 VLAIGSSRCK ANTLGPTLVQ NLPSSVQTVC ESWNNIHTNE FPNIGSWRNA FANDTIPSES YISAVQAAHL GTLCSQSLPL AASLRHTLLS LVRLTGDLIV
1301 WSDEMNPPQV IRTLLPLLLE SSTESVAEIS SNSLERTLGP AESDEFLARV YEKLITGCYN ILANHADPNS GLDESILEEC LQYLBKQLBS SQARKAMEEP
1401 FSDSGELVQI MMATANENLS AKFCNRVLKF FTKLFQLTEK SPNPSLLHLC GSLAQLACVE PVRLQAWLTR MTTSPPKDSD QLDVIQENRQ LLQLLTYIV
1501 RENSQVGEGV CAVLLGTLTP MAFEMLANGD GTGFPELMVV MATLASAGQG AGHLQLNNAA VDWLSRCKKY LSQKNVVEKL NAPVMHGKHV MILPCTCHIM
1601 SYLADVTNAL SQSMGQGPSH LSVDGEERAI EVDSDWVEEL AVEEEDSQAE DSDEDSLCNK LCTFTITQKE FMNQHWYHCH TCKMVDGVGV CTVCAKVCKK
1701 DHEISTAKYG SFFCDCGAKE DGSCLALVKR TPSSGMSSTM KESAFQSEPR ISESLVRHAS TSSPADKAKV TISDGKVADE EKPKKSSLCR TVEGCREELQ
1801 MQANFSFAPL VLDMLNFLMD AIQTNFQQAS AVGSSSPAQQ ALSELHTVEK AVEMTDQLMV PTLGSQEGAF ENVRMNYSGD QGQTIRQLIS AHVLRRVAMC
1901 VLSSPHGRRQ HLAVSHEKGK ITVLQLSALL KQADSSKRKL TLTRLASAPV PFTVLSLTGN PCKEDYLAVC GLKDCHVLTF SSSGSVSDHL VLHPQLATGN
2001 FIIKAVWLPG SQTELSIVTA DFVKIYDLCV MLFFSYCQGK DALSPTFYFL LPSSKIRDVT FLFNEEGKNI IVIMSSAGYI VTQLMEEASS AQQGPFYVTN VLEINHEDLK
2101 DSNSQVAGGG VSVYYSHVLQ MLFFSYCQGK SFAATISRTT LEVLQLFPIN IKSSNGGSKT SPALCQWSEV MNHPGLVCCV QQTTGVPLVV MVKPDTFLIQ
2201 EIKTLPAKAK IQDMVAIRHT ACNEQQRTTM ILLCEDGSLR IYMANVENTS YMLQPSLQPS SVISIMKPVR KRKTATITTR TSSQVTFPID FPEHNQQLTD
2301 VEFGGNDLLQ VYNAQIKHR LNSTGMYVAN TKPGGFTIEI SNNNSTMVMT GMRIQIGTQA IERAPSYIEI FGRTMQLNLS RSRMFDFPPT REEALQADKK
2401 LNLFIGASVE PAGVTMIDAV KIYGKTKEQF GWPDEPPEEF PSASVSNICP SNLNQSNGTG DSDSAAPTTT SGTVLERLVV SSLEALESCF AVGPIIEKER
```

```
2501  NKNAAQELAT LLLSLPAPAS VQQQSKSLLA SLKSSEHHS SHKDQALLSK AVQCLNTSSK EGKDLDPEVP QRLVITARSI AIMRPNNLVH FTESKLPQME
2601  TEGMDEGKEP QKQLEGDCCS FITQLVNHFW KLHASFTKEA FLAPACLPGL THIEATVNAL VDIIHGYCTC ELDCINTASK IYMQMLLCPD PAVSFSCKQA
2701  LIRVLRPRNK RRHVTLPSSP RSNTPMGDKD DDDDEDADEK MQSSGIPNGG HIRQESQEQS EVDHGDFEMV SESMVLETAE NVNNGWPSPL EALLAGARGF
2801  PPMLDIPEDA DDETMVELAI ALSLQQDQQG SSSSALGLQS LGLSQAPSS SSLDAGTLSD TTASAPASDD EGSTAATDGS TLRTSPADHG GSVGSESGGS
2901  AVDSVAGEHS VSGRSSAYGD ATAEGHPAGP GSVSSTGAI STTTGHQEGD GSEGEGEGET EGDVHTSNRL HWVRLMLLER LLQTLPQLRN VGGVRAIPYM
3001  QVILMLTTDL DGEDEKDKGA LDNLLSQLIA RLGMDKKDVS KKNERSALNE VHLVVMRLLS VFMSRTVKSGS KSSICESSSL ISSATAAALL SSGAVDYCLH
3101  VLKSLLEYWK SQQWDEEPVA TSQLLKPHTT SSPPDMSPFF LRQYVKGHAA DVGEAYTQLL TEMVLRLPYQ IKKITDTNSR IPPPVFDHSW FYFLSEYLMI
3201  QQTPFVRRQV RKLLLFICGS KEKYRQLRDL HTLDSHVRGI KKLLEEQGIF LRASVVTASS GSALQYDTLI SLMEHLKACA EIAAQRTIWM QKPCIKDDSV
3301  LYFLLQVSFL VDEGVSPVLL QLLSCALCGS KVLAALAASS GSSSASSSSA PVAASSGQAT TQSKSSTKKS KKEEKEKEKD GETSGSQEDQ LCTALVNQLN
3401  KFADKETLIQ FLRCFLLESN SSSVRWQAHC LITLHIYPRNSS KSQQELLLDL MWSIWPELPA YGRKAAQFVD LLGYFSLKTP QTEKKLKEYS QKAVEILRTQ
3501  NHILTMHPNS NIYNTLSGLV EPDGYYLESD PCLVCNNPEV PFCYIKLSSI KVDTRYTTQ QVVKLIGSHT ISKVTVKIGD LKRTKMVRTI NLYNNRTVQ
3601  AIVELKNKPA RWHKAKKVQL TPGQTEVKID LPLPIVASNL MIEFADFYEN YQASTETLQC PRCSASVPAN PGVCGNCGEN VYQCHKCRSI NYDEKDPFLC
3701  NACGFCKYAR FDPMLYAKPC CAVDPIENEE DRKKAVSNIN TLLDQKADRVY HQLMGHRPQL ENLLCKVNEA APEKPQDDSG TAGGISSTSA SVNRYILQLA
3801  QEYCGDCKNS FDELSKIIQK VFASRKELLE YDLAQREAAT KSSRTSVQPT FTASQYRALS VLGCGHTSST KCYGCASAVT BHCITLLRAL ATNPALRHIL
3901  VSQGLIRELF DYNLRRGAAA MREEVRQLMC LLTRDNPEAT QQMNDLIIGK VSTALKSHWA NPDLASSLQY EMLLJTDSIS KEDSCWELRL RCALSLFLMA
4001  VNIKTPVVVE NITLMCLRIL QKLIKPPAPT SKKNKDVPVE ALITVKPYCN EIHAQAQLWL KRDPKASYDA WKKCLPIRGI DGNGKAPSKS ELRHLYLTEK
4101  YVWRNKQFLS RRGKRTSPLD LKLGHNNWLR QVLFTPATQA APQAACTIVE ALATIPSRKQ QVLDLLTSYL DELSIAGECA AEYLALYQKL ITSAHWKVYL
4201  AARGVLPYVG NLITKEIARL LALEEATLST DLQQGYALKS IFEPLGIIT PEENEVTEFF VTLEKDPQQE DFLQGRMPGN PYSSNEPGIG TKLJIDETQDM LLEMLEDMTT
4301  GTESETKAPM AVCIETAKRY NLDDYRTPVF IFERLGIFT TTHEGEPHEL VIPRMRGLLGD ATEEFIESLD STTDEEEDEE EVKMAGVMA QCGGLECMLN CQDCDIVALL
4401  EDDSGMELLV NNKIISLDLP VAEVYKKVWC NRQQLVKLEM NTLNVWLGTL HLALDVAEQES KDSGGAAVAE QVLSIMEIIL DESNAEPLSE DKGNLLLITGD RLAGIRDFKQ
4501  GRHLLTVLLK LFSYCVKVKV NRQQLVKLEM MOILVERFKP YCNFDKYDED HSGDDKVFLD CFCKIAAGIK NMSNGHQLKD LILQKGITQN KDQLVMLLDQ ALDYMKKHIP
4601  INSTFVRSNP SVLQGLLRII PYLSPGEVEK MOILVERFKP YCNFDKYDED HSGDDKVFLD CFCKIAAGIK NMSNGHQLKD LILQKGITQN LREHPDVNKK EKKRNAMAMR
4701  SAKNLDADIW KKFLSRPALP FILRLLRGLA IQBPGTQVLI GTDSIPNLHK LEQVSSDBGI GTLAENLLRA LREHPDVNKK PRKQQGYSTV IDAARREFRA HLAAVRLARG
4801  QKALGTLGMT TRRKGQVVTK TALLKQMEEL IEEPGLTCCI CREGYKFQPT KVLGIYTFTK RVALEEMENK PRKQQGYSTV SHFNIVHYDC GGRESHIHLI PYIIHTVLYV
4901  REEWESAALQ NANTKCNGLL PWWGPHVPES AFATCLARHN TYLQECTGQR EPTYQLNIHD IKLLFLRFPAM EQSFSADTGG DKAVKDYSAY RSSLLFWALV
5001  LNTTRATSRE EKNLQSFLEQ PKEKWVESAF EVDGFYIFTV LALHILPPEQ WRATRVEILR RLLVTSQARA VAPGGATRLT PESFLXDLLN SVP
5101  DLIYNMFKKV PTSNTEGGWS CSLAEYIRHN DMPIYEAADK ALKTFQEEFM PVETFSEFLD VAGLLSEITD
```

FIG. 1B-2

| FIG. 3B-1 |
| FIG. 3B-2 |

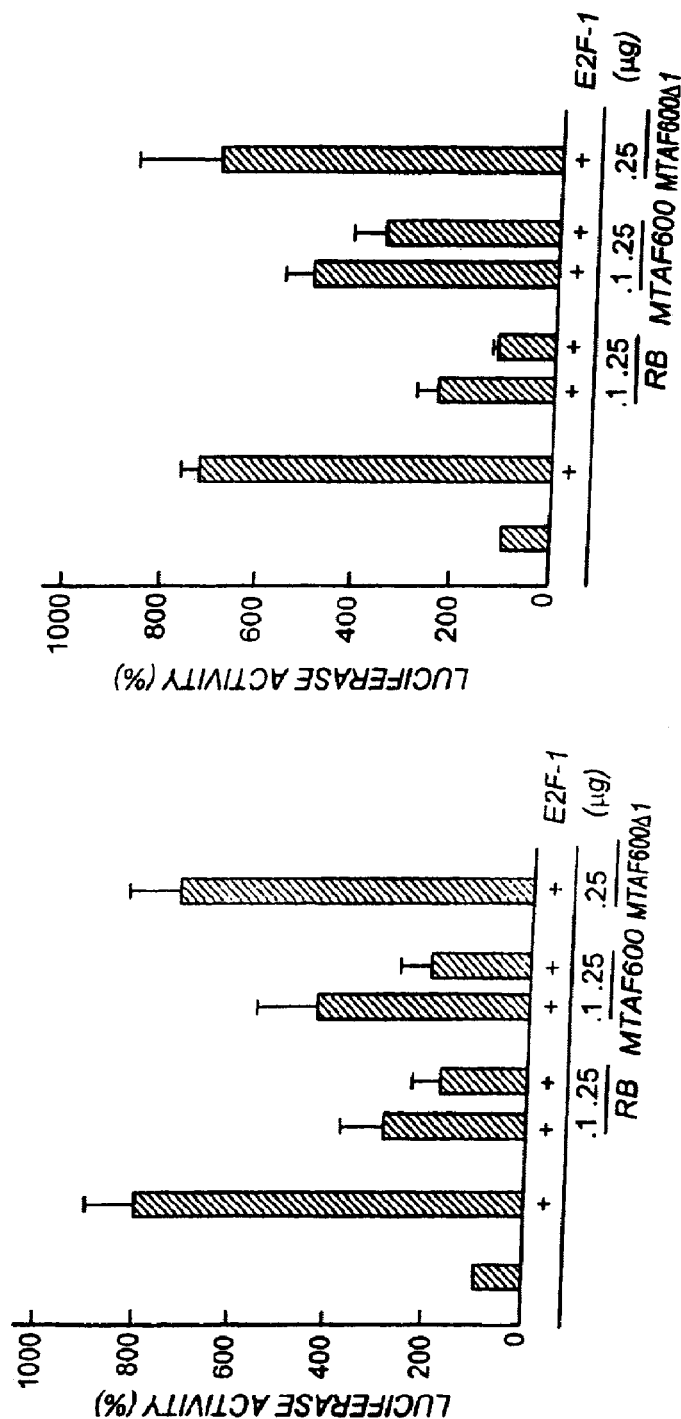

MTAF600 LOCALIZES AT KINETOCHORE
MTAF600 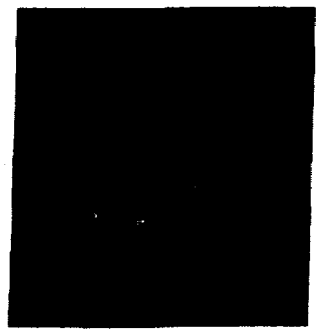     DYNEIN 
FIG. 13
MTAF600 COLOCALIZES WITH MICROTUBULES
MTAF600     α-TUBULIN 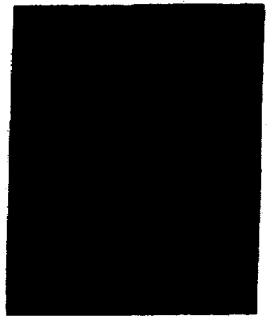    MERGE 
CYTOKINESIS
FIG. 14

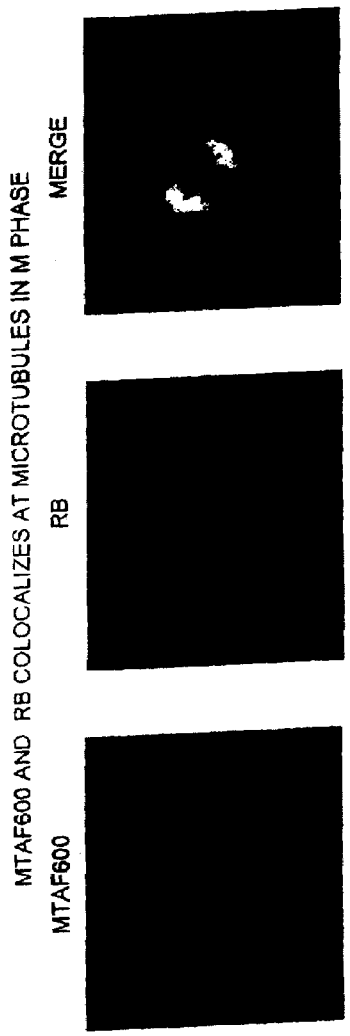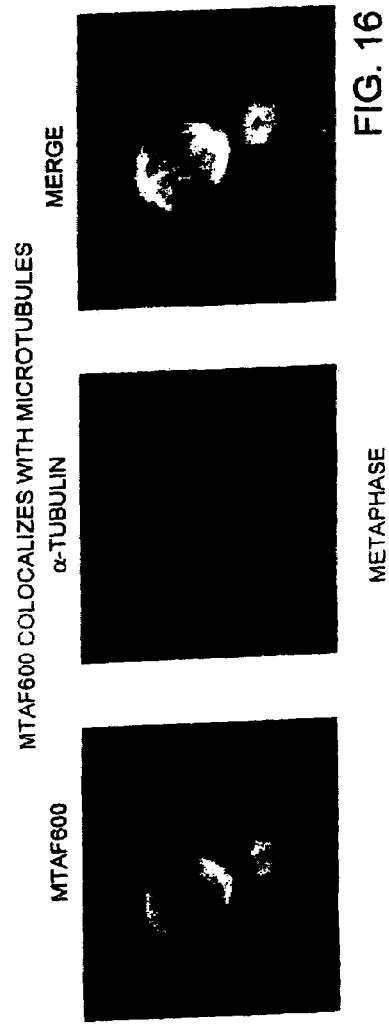

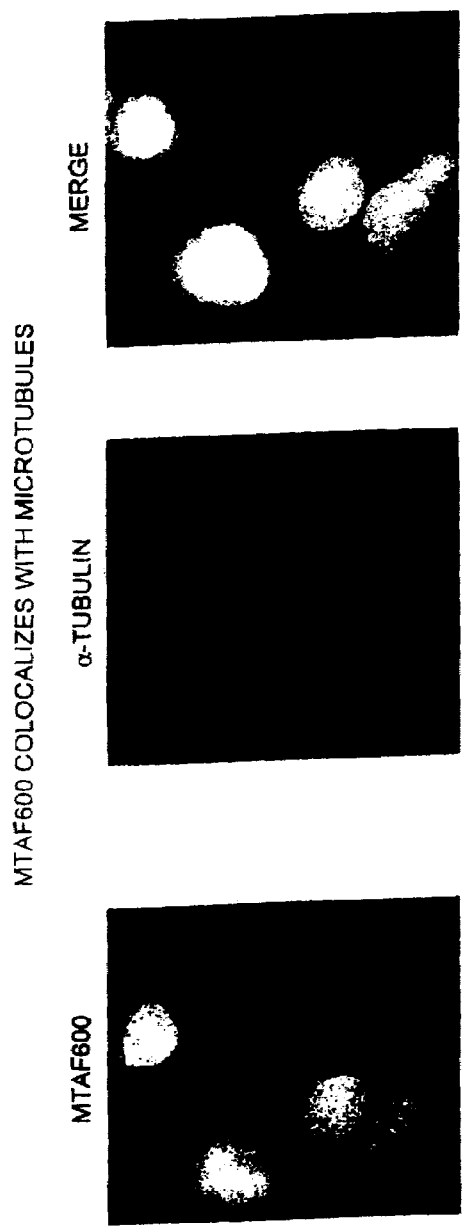
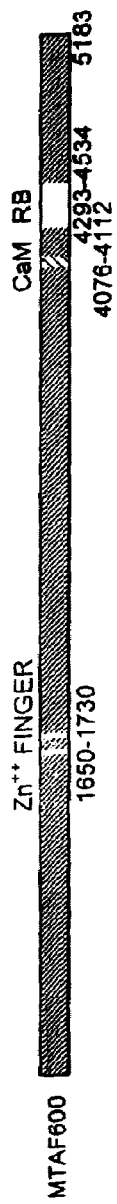
FIG. 17
FIG. 18

METHODS AND COMPOSITIONS FOR MODULATING TUMOR SUPPRESSION

CROSS REFERENCE TO RELATED APPLICATIONS

This application gains priority from provisional application serial No. 60/278,245 and provisional application 60/278,244 both filed on Mar. 23, 2001 and incorporated herein by reference.

TECHNICAL FIELD AND BACKGROUND ART

The present invention relates to reversing inhibition of tumor suppression.

The failure of normal function of the retinoblastoma tumor suppressor gene (RB) has been implicated as a contributing factor in a number of tumor types, including retinoblastomas and osteosarcomas, as well as lung, breast, and bladder carcinomas. (For reviews, see Goodrich et al., Biochim. Biophys. Acta., Vol. 1155, pp. 43–61, 1993; Zacksenhaus et al., Adv. Cancer. Res., Vol. 61, pp. 115–141, 1993; Sellers et al., J. Clin. Oncol., Vol. 15, pp. 3301–3312, 1997; Lohmann, D. R., Hum. Mutat., Vol. 14, pp. 283–288, 1999). A major role of RB is repression of the E2F family of DNA-binding transcriptional activators, which regulate the cell cycle through various genes required for S-phase entry. In resting cells, RB exists in the hypophosphorylated form that binds directly to E2F. (Reviewed in Weinberg, R. A., Cell, Vol. 81, pp. 323–330, 1995; Dyson, N., Genes Dev., Vol. 12, pp. 2245–2262, 1998). Importantly, mutations in E2F-recognition sequences, at least in some promoters, lead to derepression in G0/G1 cells, rather than repression in S-phase. (Neuman et al., Mol. Cell. Biol., Vol. 14, pp. 6607–6615, 1994). Although RB binds to the promoters only through E2F, RB is capable of repressing not only E2F, but also various activators that bind to E2F-responsive promoters. It has been proposed that chromatin modifiers, including histone deacetylases, (Brehm et al, Nature, Vol. 391, pp. 597–601, 1998), ATP-dependent chromatin remodeling factors (Zhang et al., Cell, Vol. 101, pp. 79, 2000), and DNA methyltransferases (Fuks et al., Nat. Genet., Vol. 24, pp. 88–91, 2000; Robertson et al., Nat. Genet., Vol. 25, pp. 338–3342, 2000) are involved in the mechanisms of this active repression. (Harbour et al., Curr. Opin. Cell Biol., Vol. 12, pp. 685–689, 2000).

Once RB becomes hyperphosphorylated, it dissociates from E2F resulting in expression of E2F-responsive genes. This hyperphosphorylation event at the time of the G1/S transition of the cell cycle, (For reviews, see Weinberg, Cell, Vol. 81, pp. 323–330, 1995; Sherr, "Cancer cell cycles", Science, Vol. 274, pp. 1672–1677, 1996; Dyson, Genes Dev., Vol. 12, pp. 2245–2262, 1998; Mittnacht, Vol. 8, pp. 21–27, 1998) is thought to occur through the enzymatic activity of cyclin-dependent kinases (CDK). Accordingly, RB regulates S-phase entry through binding to E2F in a cell cycle-dependent manner. This cell cycle-dependent regulation is disturbed by viral transforming factors, including adenovirus E1A, simian virus 40 large-T antigen, and human papillomavirus (HPV) E7. (For reviews, see Zalvide et al., Mol. Cell. Biol., Vol. 15, pp. 5800–5810, 1995; Flint et al., Annu. Rev. Genet., Vol. 31, pp. 177–212, 1997). These transforming factors bind to the evolutionally conserved C-terminal region of RB, referred to as the pocket domain, and inhibit access of RB to E2F, leading to loss of G1 control.

In mammals, two proteins, namely p107 and p130, are structurally and functionally related to RB (For reviews, see Dyson, N., Genes Dev., Vol. 12, pp. 2245–2262, 1998; Lipinski et al., Oncogene, Vol. 18, pp. 7873–7882, 1999). All family members, namely RB, p107, and p130, bind to E2F and actively inhibit E2F-responsive transcription, leading to G0/G1 arrest. Although the RB family members are similar in these properties, they are differentially expressed during mouse development (Reviewed in Jiang et al., Oncogene, Vol. 14, pp. 1789–1797, 1997; Lipinski et al., Oncogene, Vol. 18, pp. 7873–7882, 1999). While RB nullzygous mutant embryos die at midgestation with multiple defects (Clarke et al., Nature, Vol. 359, pp. 328–330, 1992; Jacks et al., Nature, Vol. 359, pp. 295–300, 1992; Lee et al., Nature, Vol. 359, pp. 288–294, 1992), p107 and p130 nullzygous mice do not have any obvious developmental or tumor phenotype (Cobrinik et al, Genes Dev., Vol. 10, pp. 1633–1644, 1996; Lee et al., Genes Dev., Vol. 10, pp. 1621–1632, 1996). This phenotypic difference may be due to unique roles of RB and/or distinct expression profiles of RB. On the other hand, mouse embryonic fibroblasts carrying inactivating disruptions in all three RB gene family members are viable and proliferate in culture (Dannenberg et al., Genes Dev., Vol 14, pp. 3051–3064, 2000; Sage et al., Genes Dev, Vol. 14, pp. 3037–3050, 2000). Importantly, triple knockout fibroblasts have a shorter cell cycle and are insensitive to G0/G1 arrest signals following contact inhibition or serum starvation. These results support the view that the RB family members play an essential role in growth arrest.

In mammals, the E2F family has six members, namely E2F-1 to -6 (For reviews, see Dyson, N., Genes Dev., Vol. 12, pp. 2245–2262, 1998; Black et al., Gene, Vol. 237, pp. 281–302, 1999). All family members recognize the same DNA sequence as a heterodimer with either DP-1 or DP-2. E2F-6 differs from other E2F family members in that it lacks the transactivation and RB-binding domains, suggesting that it acts antagonistically to other E2F family members by occupying the binding sites on promoters (For reviews, see Cartwright et al., Oncogene, Vol. 17, pp. 611–623, 1998; Gaubatz et al., Proc. Natl. Acad. Sci. U.S.A., Vol. 95, pp. 9190–9195, 1998; Trimarchi et al., Proc. Natl. Acad. Sci. U.S.A., Vol. 95, pp. 2850–2855, 1998). On the other hand, E2F-1 to -5 all have transactivation and RB-binding domains. While their function could be partly redundant, several lines of evidence indicate specific roles for each E2F member (Reviewed in Dyson, N., Genes Dev., Vol. 12, pp. 2245–2262, 1998; Black et al., Gene, Vol. 237, pp. 281–302, 1999). First, each E2F protein preferentially binds to different RB family members: RB binds to E2F-1 to -4; p107 interacts with E2F-4; and p130 interacts with E2F-4 and -5. In addition, E2F-1 to -5 are differently regulated according to cell type and developmental stage. Furthermore, E2F-1 to -3 appear to be exclusively nuclear, whereas a significant portion of E2F-4 and E2F-5 are present in cytoplasm (Allen et al., J. Cell. Sci., Vol. 110, pp. 2819–2831, 1997; Lindeman et al., Proc. Natl. Acad. Sci. U.S.A., Vol. 94, pp. 5095–5100, 1997; Verona et al., Mol. Cell. Biol., Vol. 17, pp. 7268–7282, 1997).

Although RB was identified over a decade ago as the first tumor suppressor (Friend et al., Nature, Vol. 323, pp. 643–646, 1986; Fung et al., Science, Vol. 236, pp. 1657–1661, 1987; Lee et al., Nature, Vol. 329, pp. 642–645, 1987), to our knowledge RB has never been purified to homogeneity. Here, we report its purification in a native form, and we demonstrate that RB is present in a complex. The 600 kDa subunit, referred to as microtubule-associated factor (MTAF) 600, interacts directly with RB and microtubules and plays a role in active repression of E2F-responsive genes, cell cycle arrest, and genomic stability. These findings indicate that RB functions as a complex in vivo.

Because of the importance of RB in tumor suppression and growth arrest, and the demonstrated occurrence of tumors in subjects in which the RB gene has been mutated, there is significant clinical interest in identifying how the process of tumor suppression can be manipulated. In the future, as prognostic tests for a variety of diseases improve, it will be desirable to modulate the expression of key proteins associated with disease.

SUMMARY OF THE INVENTION

In a first embodiment of the invention there is provided a polypeptide comprising an amino acid sequence at least 90% homologous to SEQ ID No 1. In accordance with another embodiment of the invention, a peptide is provided. The peptide comprises an amino acid sequence for MTAF600 such that the amino acid sequence has at least 90% homology with amino acid sequence 3,910–4851 of SEQ ID No 1. Similarly, in accordance with a further embodiment of the invention, a peptide may comprise an amino acid sequence corresponding to amino acid 4293–4534 of SEQ ID: No. 1. In accordance with yet another embodiment of the invention, a small molecule is provided. The molecule has a molecular weight of less than 1500 D and capable of binding at least one of RB (379–928), P107, P130, E2F1–5, or microtubules.

In accordance with another embodiment of the invention, a pharmaceutical composition is provided. The pharmaceutical composition includes an effective dose for treating a hyperproliferative condition of at least one of a polypeptide comprising an amino acid sequence at least 90% homologous to SEQ ID No 1, a peptide having an amino acid sequence for MTAF600 such that the amino acid sequence has at least 90% homology with amino acid sequence 3,910–4851 of SEQ ID No 1, a peptide including an amino acid sequence corresponding to amino acid 4293–4534 of SEQ ID: No. 1, or a small molecule having a molecular weight of less than 1500 D and capable of binding at least one of RB (379–928), P107, P130, E2F1–5 or microtubules.

In accordance with another embodiment of the invention, a method for treating a hyperproliferative disease comprises administering an effective dose of a pharmaceutical composition wherein the pharmaceutical composition includes an effective dose for treating a hyperproliferative condition of at least one of a polypeptide comprising an amino acid sequence at least 90% homologous to SEQ ID No 1, a peptide having an amino acid sequence for MTAF600 such that the amino acid sequence has at least 90% homology with amino acid sequence 3,910–4851 of SEQ ID No 1, a peptide including an amino acid sequence corresponding to amino acid 4293–4534 of SEQ ID: No. 1, or a small molecule having a molecular weight of less than 1500 D and capable of binding at least one of RB (379–928), P107, P130, E2F1–5 or microtubules.

In related embodiments of the invention, the hyperproliferative condition may be a cancer. In further related embodiments, the cancer may be retinoblastoma, osteosarcoma, lung cancer, breast cancer or bladder cancer In accordance with another embodiment of the invention, a vector comprises a nucleic acid sequence encoding SEQ ID No: 1 or a biologically active substituent thereof operably linked to a regulatory sequence for providing transcriptional activity in a host cell. In accordance with related embodiments, the nucleic acid sequence comprises at least 50% of the nucleotides 11,728–14,553 of the gene sequence encoding MTAF600 corresponding to a peptide having amino acids 3,910–4851 or nucleotide 13,611–14,767 of the gene sequence encoding MTAF600 corresponding to a peptide having amino acids 4,293–4,534. In accordance with yet another related embodiment, an in vitro cell culture includes a nucleic acid sequence encoding SEQ ID No: 1 or a biologically active substituent thereof operably linked to a regulatory sequence for providing transcriptional activity in a host cell.

In accordance with another embodiment of the invention, a method of diagnosing a susceptibility to cancer of a subject is provided. The method comprises: (a) obtaining a tissue sample from the subject and (b) screening the tissue sample for mutations in the chromosome 1 p36 relating to expression of MTAF600 protein.

In accordance with a further embodiment of the invention, a reagent for assaying for the presence of normal or mutated MTAF600 is provided. The reagent comprises at least one of a polyclonal antibody, a monoclonal antibodies or a Fab fragments having specificity for epitopes of intact MTAF600 or fragments thereof. In accordance with a related embodiment, a reagent for assaying for the presence of normal or mutated MTAF600 comprises nucleic acid probes and primers for detecting DNA or mRNA encoding MTAF600 or fragments thereof. In accordance with a further related embodiment, a method of diagnosing a susceptibility to a cancer or a type of cancer in a subject comprises obtaining a cell sample from the subject, and subjecting the cell sample to an immunoassay comprising at least one of a polyclonal antibody, a monoclonal antibodies or a Fab fragments having specificity for epitopes of intact MTAF600 or fragments thereof. In accordance with yet another related embodiment, a method of diagnosing a susceptibility to a cancer or a type of cancer in a subject comprises obtaining a cell sample from the subject, and subjecting the cell sample to an immunoassay comprising nucleic acid probes and primers for detecting DNA or mRNA encoding MTAF600 or fragments thereof In accordance with another embodiment of the invention, an animal model is provided. The animal model includes a mouse having a deletion in its genome corresponding to the entire gene or a fragment of a gene at a locus selected from the RB gene and the MTAF600 gene.

In accordance with a further embodiment of the invention, a method of inhibiting E2F-mediated transcription in a cell is provided. The method comprises administering to the cell a polypeptide comprising an amino acid sequence at least 90% homologous to SEQ ID No 1, a peptide having an amino acid sequence for MTAF600 such that the amino acid sequence has at least 90% homology with amino acid sequence 3,910–4851 of SEQ ID No 1, a peptide including an amino acid sequence corresponding to amino acid 4293–4534 of SEQ ID: No. 1, or a small molecule having a molecular weight of less than 1500 D and capable of binding at least one of RB (379–928), P107, P130, E2F1–5 or microtubules that binds to retinoblastoma protein to inhibit the E2F-mediated transcription.

In accordance with another embodiment of the invention, a method of treating a subject that has a heterozygous or homozygous mutation in the RB gene is provided. The method comprises administering to the subject an effective amount of a polypeptide comprising an amino acid sequence at least 90% homologous to SEQ ID No 1, a peptide having an amino acid sequence for MTAF600 such that the amino acid sequence has at least 90% homology with amino acid sequence 3,910–4851 of SEQ ID No 1, a peptide including an amino acid sequence corresponding to amino acid 4293–4534 of SEQ ID: No. 1, or a small molecule having a molecular weight of less than 1500 D and capable of binding at least one of RB (379–928), P107, P130, E2F1–5 or microtubules.

In accordance with a further embodiment of the invention, a method of treating a subject that has a heterozygous or homozygous mutation in the RB gene is provided. The method comprises administering to the subject an effective amount of a peptide or small molecule that interacts with a polypeptide comprising an amino acid sequence at least 90% homologous to SEQ ID No 1, a peptide having an amino acid sequence for MTAF600 such that the amino acid sequence has at least 90% homology with amino acid sequence 3,910–4851 of SEQ ID No 1, a peptide including an amino acid sequence corresponding to amino acid 4293–4534 of SEQ ID: No. 1, or a small molecule having a molecular weight of less than 1500 D and capable of binding at least one of RB (379–928), P107, P130, E2F1–5 or microtubules.

In accordance with another embodiment of the invention, a screening assay for identifying molecules with binding affinity to RB includes (a) selecting a protein having a large pocket corresponding to amino acids 379–928, (b) subjecting the protein to a library of small molecules so as to identify small molecules capable of binding the large pocket, and (c) testing the small molecule for competitive inhibition of binding of MTAF600 with RB.

BRIEF DESCRIPTION OF THE DRAWINGS

The foregoing features of the invention will be more readily understood by reference to the following detailed description, taken with reference to the accompanying drawings, in which:

FIG. 3 shows that RB sites are required for MTAF600 interaction.

FIG. 4 shows that MTAF interacts with all RB family members.

FIG. 5 shows MTAF600 sites required for RB binding.

FIG. 6 shows that MTAF600 is involved in repression of E2F-responsive genes by the RB family members.

FIG. 6(c) shows that MTAF600 (3910–4851) represses E2F-responsive promoter activity in both RB+/+ 3T3 fibroblasts.

FIG. 6(d) shows that MTAF600 (3910–4851) represses E2F-responsive promoter activity in both RB−/− 3T3 fibroblasts.

FIG. 13 shows how MTAF600 localizes at the Kinetochore of the nucleus.

FIG. 14 shows the co-localization of MTAF600 with alpha tubulin along the spindle during telophase.

FIG. 15 shows co-localization of MTAF600 and RB with microtubules in Metaphase.

FIG. 16 shows co-localization of MTAF600 with alpha tubulin along the spindle in metaphase FIG. 17 shows MTAF600 associated with microtubules in interphase.

FIG. 18 shows the protein binding domains in MTAF600 amino acid sequence.

DETAILED DESCRIPTION OF SPECIFIC EMBODIMENTS

Figure 1A:
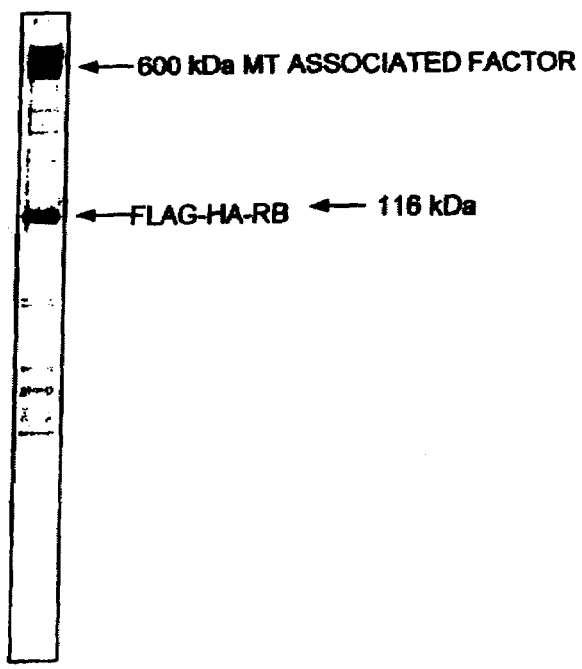
FIG. 1a shows a characterization of the purified RB Complex from Hela cells resolved by SDS-PAGE and stained with Coomassie brilliant blue R250 showing the results obtained from Hela cells expressing RB with the FLAG epitope tag at the N-terminus (f: RB) by immunoprecipitation with anti-FLAG antibody.

Definitions. As used in this description and the accompanying claims, the following terms shall have the meanings indicated, unless the context otherwise requires:

The term "substantially similar" or "substantially homologous" refers to MTAF600, means a protein, peptide or small molecule having MTAF600 sequence.

A "high degree of homology" refers to at least approximately 70% amino acid homology.

A "retinoblastoma complex" refers to a complex that contains proteins and/or other factors necessary for tumor suppressor activity to occur. The complex may include for example any or all of MTAF600, RB, P107, P130, E2F1–5, DP1 or 2, calmodulin or calcium ions. The proteins and/or factors in the complex are characterized by their role in modulating tumor suppressor activity associated with RB. The retinoblastoma complex of proteins does not exclude other proteins or non-protein factors than those recited above provided that it can be shown using any of the assays provided herein (see FIGS. 1 through 7) or using other assays known in the art that the protein or non-protein factor play a role in tumor suppression associated with RB.

"Retinoblastoma" is a malignant tumor of the eye. Mutations that affect both alleles of the retinoblastoma susceptibility gene are a prerequisite for the development of this tumor. The retinoblastoma susceptibility gene (RB gene) consists of 27 exons scattered over 180 kb at chromosome 13q14 (Lohmann, Hum. Mutat., Vol. 14, pp. 283–288; 1999). Retinoblastoma protein appears to inhibit G1-S transition by inhibiting E2F activity and to affect genome stability.

The term "administration to a subject" encompasses any of the methods of drug delivery known in the art. For example, gene therapy is one form of delivery in which the gene encoding the agent is expressed in the subject either because it is introduced or because regulatory sequences are manipulated by an exogenous promotor, enhancer or operator to alter the endogenous expression. Various methods of transferring or delivering DNA to cells for expression of the gene product protein, otherwise referred to as gene therapy. (Yang, Crit. Rev. Biotechnol. 12(4): 335–356; 1992 which is hereby incorporated by reference). A more detailed description of a variety of approaches to gene therapy can be found in U.S. Pat. No. 5,854,221 herein incorporated by reference.

The term "vector" refers to a carrier that can contain or associate with specific nucleic acid sequences, which functions to transport the specific nucleic acid sequences into a cell. Examples of vectors include plasmids and infective microorganisms such as viruses, or non-viral vectors such as ligand-DNA conjugates, liposomes, lipid-DNA complexes. It may be desirable that a recombinant DNA molecule comprising a tumor suppressor activating factor DNA sequence is operatively linked to an expression control sequence to form an expression vector capable of expressing the inhibitor. The transfected cells may be cells derived from the patient's normal tissue, the patient's diseased tissue, or may be non-patient cells.

For example, mammalian expression vectors which bind to the RB family proteins and suppress cell growth can be prepared by inserting the MTAF600 nucleotides 11,728–14,553 (encode amino acids 3,910–4,851) or MTAF600 nucleotides 14,767–13,611 (encode amino acids 4,293–4,534) for MTAF600 into the vector pFLAG-CMV2 (Sigma-Aldrich). (Ogryzko et al., Cell, Vol. 94, pp. 35–44, 1998). Alternatively MTAF600 cDNA can be obtained using overlapping cDNA clones that encoded an assembled open reading frame with the potential to encode a 5,183 amino acid polypeptide were isolated from a human fetal liver cDNA library (CLONTECH Laboratories Inc.). The insert fragments encoding MTAF600 are excised from λ phage by digesting with endonuclease NotI, and then subcloned into pBluescript SK+ vector (Stratagene). MTAF600 DNA may then be recloned into appropriated vectors as required.

Mouse models of knockout mice for MTAF600 are provided herein as research tools for studying the mechanism of tumor suppression during development and in the adult. These mouse models further serve as an in vivo screen for therapeutic agents or vectors that are directed to correcting defects in tumor suppression.

Active agents described herein can be administered to the subject by any of the methods known in the art. Routes of administration of agents include oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural), dermal, transdermal, or mucosal routes of administration. Other delivery approaches also contemplated include sustained release formulations contained within a biodegradable matrix. Treatments may include a combination of procedures and compositions.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described. Alternatively, the agent can be formulated by means of sustained-release biodegradable polymers similar to those described in U.S. Pat. No. 5,854,221 herein incorporated by reference.

Formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product. Dosage units include those that contain a daily dose or unit, daily sub-dose, or an appropriate fraction thereof, of the administered ingredient.

Reagents for detecting target molecules, assaying their concentration and determining their binding kinetics may include antiserum, polyclonal antibodies, monoclonal antibodies or fragments of monoclonal antibodies that have binding specificity for MTAF600, peptide fragments of MTAF600 or analogs of the same or compete with MTAF600 for binding with other molecules in the RB complex (including RB, P107, P130, E2F1–5 and DP 1 or 2).

Methods for making antisera, polyclonal antibodies and monoclonal antibodies or Fab fragments are well established in the art (see for example, the description of techniques in U.S. Pat. No. 5,854,221).

For example, antigens for polyclonal and monoclonal antibodies against MTAF600 nucleotides 9,028–10,110 (encoding amino acids 3,010–3,370) were prepared using bacterial expression vector pET28a(+), information for which can be found on the internet at "www.novagen.com". Recombinant MTAF600 (amino acid residues 3,010–3,370) were expressed in *E. coli* BL21(DE3) as an N-terminal His-tagged protein and purified by Ni-NTA agarose (QIAGEN) according to the manufacturers's protocol. The resulting protein will be used to raise polyclonal and monoclonal antibodies. Kits for measurement of the active agent that provide rapid, reliable, sensitive, and specific measurement and localization of molecules include competitive and non-competitive assays, radioimmunoassay, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry. For each kit the range, sensitivity, precision, reliability, specificity and reproducibility of the assay are established. The kit is useful for the measurement of MTAF600 in animals and humans with and without tumors.

Another kit useful for both research and clinical analysis uses immunohistochemistry or laser scanning cytometry techniques, which are well known to those skilled in the art. These techniques permit localization of MTAF600 in tissues and cells using both light and electron microscopy. For example, tumors are biopsied or collected and tissue sections cut with a microtome to examine sites of inhibitor production. Such information is useful for diagnostic and possibly therapeutic purposes in the detection and treatment of cancer.

Assays may utilize extracts of various tissues, including but not limited to primary and secondary tumors, including retinoblastoma, osteosarcoma and cancers of the lung, breast and bladder.

Here, we report the purification of RB in its native form and we demonstrate that RB is present in the complex with P107 and P130. The 600 kDa subunit, referred to as MT-associated factor (MTAF) 600, interacts directly with RB and microtubules and plays a role in active repression of E2F-responsive genes, cell cycle arrest, and genomic stability.

Loss of RB binding to the E2(1–5) complex for an RB mutant can give rise to the tumor phenotype. Correction of that defect either by repair of the RB lesion or by substituting an E2(105) binding molecule that can reconstitute a normal phenotype for the abnormal one has therapeutic value. The interaction between MTAF600 and the RB complex as well as the interaction between the RB complex and the E2(1–5) complex provides the basis for an assay that may be used to identify small molecules that can be used to manipulate the cell cycle. For example, small molecules may be identified that disrupt the association of MTAF600 with the RB complex (RB, P107 and P130) and hence disrupt E2F-dependent transcription.

The RB Complex

It is here demonstrated for the first time that RB forms a stoichiometric (or nearly stoichiometric) complex with MTAF600. Immunoprecipitation experiments indicate that MTAF600 binds to RB regardless of the phosphorylation status of RB. Moreover, MTAF600 binds to RB without disrupting the interaction between RB and E2F. While not wishing to be limited by theory, it is proposed here that it is likely that the hypophosphorylated form of RB gains access to E2F as a complex with MTAF600, rather than as free RB. In support of this view, E2F and DP proteins, in addition to MTAF600, are copurified with RB when the FLAG-epitope tag is attached at the protein's C-terminal end. Further, MTAF600 appears to be required for repression of E2F-mediated transcription by RB. In all, we conclude that the RB complex, containing RB and MTAF600, is a natural and functional form of RB.

While there might be other RB-containing complexes, the MTAF600-containing complex represented here could be the dominant form, given that we purified RB by immunoprecipitation from nuclear extracts without fractionation and then identified MTAF600 as a major component in immunoprecipitated materials. Our purified complex does not include RB-binding proteins that have been previously reported, except for E2F and DP, which copurified with C-terminally tagged RB. However, previously identified RB-binding proteins are not excluded. (Reviewed in Mulligan et al., Trends Genet., Vol. 14, pp. 223–229, 1998; Lipinski et al., Oncogene, Vol. 18, pp. 7873–7882, , 1999; and Dick et al., Mol. Cell. Biol., Vol. 20, pp. 3715–3727, 2000). We believe that the RB complex, rather than RB alone, is a minimum functional unit and that previously identified RB-binding proteins interact with the RB complex to regulate functions.

Drosophila Homolog of MTAF600

The protein push, whose gene encodes the Drosophila homolog of MTAF600, has been isolated as a gene that is involved in neuronal excitability. (Richards et al., Genetics, Vol. 142, pp. 1215–1223, 1996). Mutations in push cause increased release of transmitter at the neuromuscular junction, which might be caused by altered microtubule function. Moreover, push has been independently identified as a gene that affects meiosis and male sterility. (Sekelsky et al., Genetics, Vol. 152, pp. 529–542, 1999). Mutants of push are defective in meiotic chromosome segregation and spindle formation. These results suggest that MTAF600 plays a role not only in retardation of S-phase entry but also regulation of chromosomal segregation in meiosis and mitosis.

Further, push has been independently identified as the calmodulin-binding protein calo. (Xu et al., J. Biol. Chem., Vol. 273, pp. 31297–31307, 1998). Consistent with this report, we have found calmodulin as a third subunit of the RB-complex, although calmodulin cannot be detected in the gel shown in FIG. 1A due to its small molecular weight. Calmodulin directly interacts with MTAF600.

Plant Homolog of MTAF600

A protein of exceptional size that is associated with auxin transport has been named BIG. BIG has been associated with positioning of auxin efflux carrier at the plasma membrane via control of vehicle transport or fusion. It appears to have significant identity with Drosophila protein Calossin/Pushover. (Gil et al., Genes and Development, Vol. 15, pp. 1985–1997). We determine here that BIG is related to MTAF600 and that where BIG provides vehicle transport relating to auxins, MTAF600 functions in microtubule mediated transport. Interestingly, Drosophila Pushover is also associated with transport in particular synaptic trnasmission at the neuromuscular junction The MTAF600-binding Sites on RB The RB region (residues 379–772; see FIG. 3A), which contains the evolutionarily conserved domains A and B, is referred to as the "small pocket" domain. Crystal structure of the small pocket demonstrates that the A and B boxes each contain a helical structural motif, which is referred to as the "cyclin-fold". (Lee et al., Nature, Vol. 391, pp. 859–865, 1998) Although RB, cyclin A, and transcription initiation factor TFIIB have quite distinct biological functions, each has 2 cyclin motifs and interacts with target proteins in a similar fashion. (Bagby et al., Cell, Vol. 82, pp. 857–867, 1995; Jeffrey et al., Nature, Vol. 376, pp. 313–320, 1995; Nikolov et al., Nature, Vol. 377, pp. 119–128, 1995). While the first cyclin fold of cyclin A and TFIIB respectively interact with CDK2 and TBP, the second cyclin fold of RB (B domain) interacts with the LXCXE motif of E7 The LXCXE-binding domain of RB is highly conserved among species as well as among RB family members, (Lee et al., Nature, Vol. 391, pp. 859–865, 1998) and thus is considered to be a target for various cellular factors. The following cellular RB-binding proteins possess LXCXE or a related sequence that may be involved in RB-binding: histone deacetylase 1 (HDAC1); HDAC2; BRG1; hBrm; retinoblastoma binding protein 1 (RBP1); RBP2; AhR; Bog; CtIP; cyclin D1; cyclin D2; cyclin D3; Elf-1; HBP1; HEC1; hsp75; Rim; RIZ; and UBF. (Reviewed in Dick et al., Mol. Cell. Biol., Vol. 20, pp. 3715–3727, 2000). Some of these proteins contribute to active repression of E2F-mediated transcription by RB (discussed below).

While the LXCXE-binding domain of RB is a potential target for various cellular proteins, binding of E2F is independent of the LXCXE-binding domain of RB. Moreover, E2F does not bind to the small pocket but to the large pocket (residues 379–928), (Huang et al., DNA Cell Biol., Vol. 11, pp. 539–548, 1992; Shan et al., Proc. Natl. Acad. Sci. U.S.A., Vol. 93, pp. 679–684, 1996) suggesting that E2F may interact with both the small pocket and the C domain. Alternatively, E2F may bind to only C-domain, but the small pocket might be required for proper folding of the C domain or vice versa. Interestingly, binding properties of MTAF600 to RB appear to be similar to those of E2F, namely, independence of the LXCXE-binding domain and dependence on the large pocket. However, given that MTAF600 and E2F do not compete for binding to RB, the RB surface for MTAF600-binding could be distinct from that for E2F-binding. Active repression of E2F-responsive transcription by RB In the early days of research on inhibitory mechanisms by RB, it was thought that RB simply neutralizes the activator function of E2F. However, deletion of the E2F-binding sites in some promoters leads to up-regulation of transcription activity in G0/1 rather than down-regulation in S-phase. (Neuman et al., Mol. Cell. Biol., Vol. 14, pp. 6607–6615, 1994). We propose here that E2F functions as a repressor of transcription in G0/G1 that is mediated through the RB family members. Support for the link between RB and chromatin modifications include the following:

First, histone acetylases (HDAC1, 2 and 3) have been shown to interact directly with RB. (Brehm et al., Nature, Vol. 391, pp. 597–601, 1998; Ferreira et al., Proc. Natl. Acad. Sci. U.S.A., Vol. 95, pp. 10493–10498, 1998; Luo et al., Cell, Vol. 92, pp. 463–473, 1998; Magnaghi-Jaulin et al., Nature, Vol. 391, pp. 601–605, 1998). Acetylation of core histone tails plays an important role in transcriptional activation in chromatin contexts. Recruitment of histone deacetylases to promoters via E2F and RB could allow them to alter acetylation status and maintain chromatin in a hypoacetylated state. Moreover, RB and DNA methyltransferase appear to be functionally related. (Fuks et al., Nat. Genet., Vol. 24, pp. 88–91, 2000; Robertson et al., Nat. Genet., Vol. 25, pp. 338–3342, 2000). Although the molecular mechanisms are unclear, methylation of the CpG island is associated with transcriptional silencing and the formation of high-ordered chromatin structures enriched in hypoacetylated histones. The finding that the DNA methyltransferase DNMT1 copurifies with HDAC1, RB, and E2F (Robertson et al., Nat. Genet., Vol. 25, pp. 338–3342, 2000) suggests that targeted methylation as well as deacetylation in E2F-responsive promoters may contribute to active repression.

Another model of active repression involves chromatin remodeling. ATP-dependent chromatin remodeling factors regulate transcription in both positive and negative ways by changing the positioning of nucleosomes to transcription-competent and -incompetent states, respectively. (Kingston et al., Genes Dev., Vol. 13, pp. 2339–2352, 1999) The BRG1 subunit (a human homolog of SWI2/SNF2) of the chromatin-remodeling complex has been shown to interact with RB and contribute to active repression. (Zhang et al., Cell, Vol. 101, pp. 79, 2000). In addition to these chromatin modifiers, RBP1, HBP1, RIZ, and RBP2 have shown to contribute to active repression by interacting with RB. (Reviewed in Dick et al., Mol. Cell. Biol., Vol. 20, pp. 3715–3727, 2000).

FIGS. 10–17 illustrate the colocalization of MTAF600 with microtubules and alpha-tubulin, its association with spindles and centrosomes and the role of MTAF600 in cytokinesis. MTAF600 plays various roles in events mediated by microtubules for example, chromatin segregation, nuclear division, cytokinesis and microtubule mediated transport.

We have shown for the first time that MTAF600 is responsible for active repression in an RB-interaction-dependent manner. While we believe that this repressive activity in the RB-binding domain of MTAF600 reflects a role in the full-length protein, it is highly possible that this activity is regulated, for instance, by an allosteric effect in the full-length MTAF600. Further, interaction between MTAF600 and RB is a potential regulatory point. As we demonstrated, viral transforming factor E7, by interacting with RB, inhibits not only access of E2F, but also that of MTAF600 to RB. Likewise, cellular factors may regulate the MTAF600-RB interaction by a mechanism distinct from regulation of the RB-E2F interaction.

RB mutants lacking LXCXE-binding activity were constructed and were found not to bind to LXCXE-containing viral transforming factors. However, importantly, they still retain the ability to arrest the cell cycle at G1 (Chen and Wang, Mol. Cell. Biol., Vol. 20, pp. 5571–5580, 2000; Dahiya et al., Mol. Cell. Biol., Vol. 20, pp. 6799–6805, 2000; Dick et al., Mol. Cell. Biol., Vol. 20, pp. 3715–3727, 2000) and to actively repress E2F-mediated transcription.

(Dahiya et al., Mol. Cell. Biol., Vol. 20, pp. 6799–6805, 2000). Thus, LXCXE-binding sites of RB are not essential for active repression and cell cycle arrest. However, this does not necessarily mean that LXCXE-binding factors are not functional or significant. While LXCXE-binding factors appear to be nonessential for active repression, it is highly possible that LXCXE-binding factors cooperatively function with other factors for active repression. In addition, LXCXE-binding factors may play crucial roles in other biological functions, such as establishment of irreversible growth arrest in myogenic differentiation. (Chen et al., Mol. Cell. Biol., Vol. 20, pp. 5571–5580, 2000).

While HDAC1, HDAC2, RGB1, RBP1, HBP1, RIZ, and RBP2 have LXCXE motifs, (reviewed in Dick et al., Mol. Cell. Biol., Vol. 20, pp. 3715–3727, 2000) this does not necessarily mean that of these factors bind to RB in a LXCXE-binding site-dependent manner because LXCXE motifs of these factors may not be interaction sites or may not be sole binding sites. Indeed, RGB1 interacts with RB mutants lacking LXCXE-binding activity. (Dahiya et al., Mol. Cell. Biol., Vol. 20, pp. 6799–6805, 2000)

Our findings provide new insights into the mechanisms by which the RB family members function as tumor suppressors and the interaction between RB and MTAF600 to give rise to tumor suppression. The chromosomal location of MTAF600 on chromosome 1p36, which is a hot spot for genes associated with tumors (P73 and P53), further implicates this protein in its mutated form with cancer susceptibility. This is illustrated further in FIGS. 8 and 9 in which cells which have been subjected to loss of MTAF600 expression in the presence of RNAsi transform NIH 3T3 fibroblasts to form foci which are a marker of tumor formation.

Like the E2F-RB interaction, the RB-MTAF600 interaction could be regulated by cellular and viral factors. Moreover, evidence that MTAF600 is a calmodulin-binding protein strongly suggests that MTAF600 is involved in signaling.

The examples provided below are to illustrate embodiments of the invention but are not intended to be limiting. All references cited herein are incorporated by reference.

EXAMPLES

Example 1

Purification and Characterization of the RB Complex

HeLa cells were transduced with a recombinant retrovirus expressing a bicistronic mRNA that encoded FLAG-epitope tagged RB at the N-terminus linked to the ILR2α-subunit surface marker, a construct that was driven by the internal ribosome entry site, and the transduced subpopulation was purified by repeated cycles of affinity cell sorting (Ogryzko et al Cell, Vol. 94, pp. 35–44, 1998). The RB complex was purified from nuclear extracts prepared from the resulting cells by immunoprecipitated with M2 anti-FLAG agarose as described (Ogryzko et al., Cell, Vol. 94, pp. 35–44, 1998). Specific protein bands were excised from Coomassie brilliant blue R250-stained SDS-PAGE gels, digested with trypsin in the presence of 50% [$^{18}$O]-water to label the C-termini of the tryptic peptides, extracted and sequenced by tandem mass spectrometry (MS/MS) as described previously (Ogryzko et al., Cell, Vol. 94, pp. 35–44, 1998 and therein).

Overlapping cDNA clones that encoded an assembled open reading frame with the potential to encode a 5,183 amino acid polypeptide were isolated from a human fetal liver cDNA library (CLONTECH Laboratories Inc.). MTCTM Panels (CLONTECH Laboratories Inc.) were used to amplify mRNA for MTAF600 with the following primers correspond to the nucleotide positions 15153–15179 and 15403–15403, respectively 5' GAGAGCCACACGTGTG-GAAATCTTGCG-3' (SEQ ID No:7); and 5'-TCAGGGCTTTGTCGGCAGCTTCGTA-3' (SEQ ID No:8).

Protein Expression in E. coli

Various regions of RB as well as the large pocket domain of p107 and p130 were amplified by PCR and subcloned into pGEX6P-1 (Amersham Pharmacia Biotech Inc.) to express as GST fusions in E. coli. Tumor-derived point mutations were introduced into the large pocket domain of RB in pGEX6P-1 by PCR-based mutagenesis, whereas the large pocket domain of the RB9 construct was amplified by PCR to subclone into pGEX6P-1. The MTAF600 fragments and HPV-16 E7 were amplified by PCR and subcloned into pET28c (Novagen Inc.) to express as His-tagged proteins. Internal deletions of MTAF600 were introduced by PCR-based mutagenesis. GST- and His-fusion proteins were expressed and purified with glutathione-Sepharose (Amersham Pharmacia Biotech Inc.) and Ni-NTA agarose (QUIAGEN), respectively, according to the manufacturers' protocols.

Protein Expression in Mammalian Cells

Various fragments of MTAF600 and HPV-16 E7 were subcloned into pFLAG-CMV2 (Sigma-Aldrich). For stable expression, MTAF600 fragments were subcloned into pCMV-Tag2 (Stratagene). The full-length RB was subcloned into pTB701, which contains the SV40 promoter linked to an HA epitope tag (Ono et al., 1988).

Plasmids were transfected into mammalian cells with TransIT®-HeLaMONSTER™ (PanVera Corp.) or LipofectAMINE® (Life Technologies Inc.), except that COS-7 cells were transfected by electroporation using the Gene-Pulsar (Bio-Rad Laboratories).

Binding Assays

Interaction experiments were carried out in Buffer B (20 mM Tris-HCl buffer [pH 8.0]; 5 mM $MgCl_2$; 10% glycerol; 100 mM KCl; 1 mM PMSF; 10 mM 2-mercaptoethanol; 0.1% Tween 20) containing 1% Triton X-100 and 0.1 M KCl in a total volume of 20 µl. For GST-pull down experiments, ~5 pmol of GST-RB derivatives were incubated with ~1 mg of cell extracts or ~50 pmol of His-tagged MTAF600 derivatives for 30 min at 4° C. Samples were further incubated with 10 µl of glutathione-Sepharose (50% slurry) with rotation, washed 4 times, and eluted with 10 µl of SDS-PAGE sample buffer.

For immunoprecipitation experiments, cell extracts were incubated with 1 µg of antibody for 1 hr. Samples were further incubated with 10 µl of protein G-Sepharose (50% slurry) (Amersham Pharmacia Biotech Inc.) with rotation, washed 4 times, and eluted with 10 µl of SDS-sample buffer.

To test binding of MTAF600 to E2F-1 (FIG. 2B), MTAF600 was immunoprecipitated from a HeLa nuclear extract so that ~1 pmol of MTAF600 was immobilized per 5 µl of protein G-Sepharose (packed volume). The matrix was extensively washed with Buffer B containing 1% Triton X-100 and 0.3 M KCl extensively until RB was completely removed from the matrix. GST-RB (379–928) was also immobilized through anti-RB antibody at ~1 pmol per 5 µl of protein G-Sepharose (packed volume). 5 µl of the resulting beads (packed volume) were incubated with ~1 pmol of E2F-1/DP for 30 min at 4° C., washed 4 times with Buffer B containing 1% Triton X-100 and 0.1 M KCl, and eluted with 10 µl of SDS-PAGE sample buffer.

Antibodies

Rabbit polyclonal antibody against MTAF600 was raised against a fragment containing residues 3,010–3,370. For anti-human RB antibodies, clone XZ-77 (Upstate Biotechnology Inc.) was used for immunoprecipitation, whereas clone G3-245 (BD Sciences-PharMingen) and RB C-15 (Santa Cruz Biotechnology Inc.) were used for immunoblotting. Anti-FLAG M2 antibody-conjugated agarose (Sigma-Aldrich) was used for immunoaffinity purification, whereas anti-FLAG M5 antibody was used for immunoblotting. Suppliers for the other antibodies are as follows: HA 12CA5 (Roche Molecular Biochemicals); 6xHis (CLONTECH Laboratories Inc.); GST (Amersham Pharmacia Biotech Inc.); p107 C-18 (Santa Cruz Biotechnology Inc.); p130 C-20 (Santa Cruz Biotechnology Inc.); and E2F-1 KH20/KH95 (Upstate Biotechnology Inc.).

Reporter Experiments

Cells were transfected with various effector and reporter plasmids as indicated in the Legend to FIG. 5. The cells were harvested after 48 hr of transfection, and luciferase activity was measured by using Enhanced Luciferase Assay Kit (BD Sciences-PharMingen) according to the manufacturers' protocols. Luciferase activity was normalized against that of β-galactosidase and expressed as a relative activity.

Cell Cycle Analysis

Stably transfected U2OS cells were grown in DMEM containing 10% fetal bovine serum and kept for 36 hr at confluency to enrich G0/G1 cells. Cells were replated at $5 \times 10^4/cm^2$ and were further incubated. Cells were harvested at the indicated periods, analyzed by fluorescence-activated cell sorter (FACScan, BD Biosciences), and the data were analyzed using the ModFitLT program.

RNA Interference (RNAsi)

Double stranded RNA is used to target specific mRNA (MTAF600 mRNA) for degradation thereby silencing its expression. This technique has been described by Zamore, Nature, Vol. 8, pp. 746–750, 2001.

Example 2

Purification of the RB Complex

To purify RB we first established cells that stably express FLAG-epitope-tagged RB (f:RB). Although HPV-18 E7 expressed in HeLa cells is believed to inactivate RB family proteins, we risked employing HeLa cells for the following reasons: first, exogenous expression of RB in HeLa cells suppresses cell growth, indicating that RB is functional, at least in part, when exogenously expressed. Moreover, among different kinds of cells we have tested, we were only able to grow HeLa cells on a large scale when RB was exogenously expressed.

To establish HeLa cells expressing f:RB, we transduced recombinant retrovirus expressing a bicistronic mRNA that encoded f:RB linked to the ILR2 α-subunit surface marker (Ogryzko et al., Cell, Vol. 94, pp. 35–44, 1998) driven by the internal ribosome entry site. The transduced subpopulation was purified by repeated cycles of affinity cell sorting (Ogryzko et al., Cell, Vol. 94, pp. 35–44, 1998) with anti-ILR2 antibody-conjugated magnetic beads. (Ogryzko et al., Cell, Vol. 94, pp. 35–44, 1998) Using anti-FLAG antibody-conjugated agarose, f:RB was purified from nuclear extracts of the resulting cells (FIG. 1A, lane 2). As a control, mock purification was performed from non-transduced HeLa cells (lane 1). Immunoprecipitated materials were eluted with FLAG peptide and analyzed by SDS-PAGE. In addition to f:RB, the 600 kDa protein MT-associated factor (MTAF) 600 was specifically purified (lane 2).

In the course of this study, we found that most precipitated RB is hyperphosphorylated when the FLAG-tag is attached at the N-terminus, whereas most precipitated RB is hypophosphorylated when the tag is attached at the C-terminus (data not shown). Since the N-terminally and C-terminally tagged RB are both present as hyperphosphorylated and hypophosphorylated forms in HeLa cells, accessible surfaces of the protein could be drastically different between hyperphosphorylated and hypophosphorylated forms of RB, perhaps due to conformational alterations. In support of this notion, we observed that, when RB was tagged at its N-terminus, E2F and DP family members were not detected, whereas when RB was tagged at its C-terminus, DP-1 and E2F-1 were copurified with MTAF600.

Example 3

Identification of the Novel RB-associated Factor MTAF600

Figure 1B:
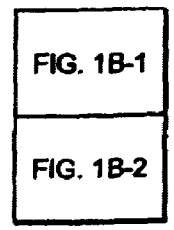
FIG. 1b shows the polypeptide sequence of MTAF600 (SEQ ID No: 1).
Figure 1C:
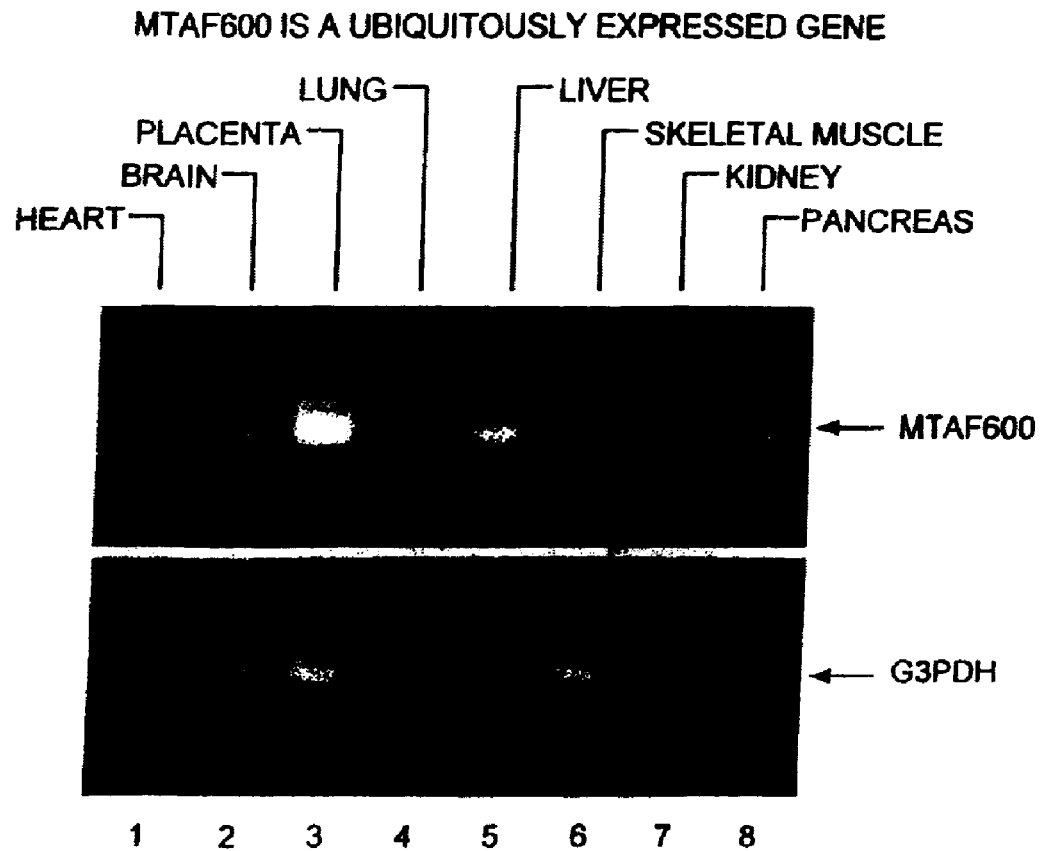
FIG. 1c shows agarose gel electrophoresis stained with ethidium bromide where MTAF600 is widely expressed in various tissues. Expression in heart, brain, placenta, lung, liver, skeletal muscle, kidney and pancreas are shown here. Messenger RNA-encoding MTAF600 was amplified by RT-PCR from poly-A+ RNA that had been isolated from various tissues. mRNA for a house-keeping gene and glycerol-3-phosphate dehydrogenase (G3PDH), was amplified as a positive control.

Using an analysis of tryptic fragments of MTAF600 by tandem mass spectrometry (MS/MS), several EST clones that encode uncharacterized polypeptides were identified. A human liver cDNA library was screened with one of the EST clones (GenBank accession number T66125) as a probe. By "cDNA walking," we isolated overlapping clones that enabled us to compose an open reading frame with the potential to encode a protein (5183 residues) with an estimated molecular mass of 573,536 Da (FIG. 1B). RT PCR analysis of RNA isolated from various human tissues indicated that MTAF600 is ubiquitously expressed (FIG. 1C).

A database search with PSI BLAST program (Altschul et al., Nucleic. Acids. Res., Vol. 25, pp. 3389–3402, 1997) identified proteins homologous to ones found in *Drosophila melanogaster*, *Arabidopsis thaliana*, and *Caenorhabditis elegans*. While the *C. elegans* sequence is incomplete, the predicted peptides of the *Drosophila* and *Arabidopsis* counterparts appear to be complete, consisting of 5322 and 5079 residues, respectively. While all of them were reported by genome projects, the *Drosophila* clone was independently isolated by genetic screening known as pushover. (Richards et al., Genetics, Vol. 142, pp. 1215–1223, 1996; Sekelsky et al., Genetics, Vol. 152, pp. 529–542, 1999). Moreover, it has also been isolated as a calmodulin binding protein, calo (Xu et al., J. Biol. Chem., Vol. 273, pp. 31297–31307, 1998) (see Discussion) where calmodulin is an abundant cell protein that is activated in the presence of calcium.

Example 4

MTAF600 Interacts with Hypophosphorylated and Hyperphosphorylated RB

The hypophosphorylated form of RB, which is abundant in quiescent or differentiating cells, inhibits E2F-dependent transcription through direct interaction with E2F proteins. In contrast, the hyperphosphorylated form of RB, which is abundant in proliferating cells, does not possess the ability to interact with E2F proteins, thus allowing the activation of E2F-dependent genes that are required for S-phase entry (Weinberg, Cell, Vol. 81, pp. 323–330, 1995; Dyson, Genes Dev., Vol. 12, pp. 2245–2262, 1998).

To elucidate the mechanism whereby MTAF600 participates in the RB-E2F pathway, we determined which form of RB, whether hyperphosphorylated or hyperphosphorylated, binds to MTAF600. Further, we examined whether MTAF600 affects the RB-E2F interaction.

Figure 2A:
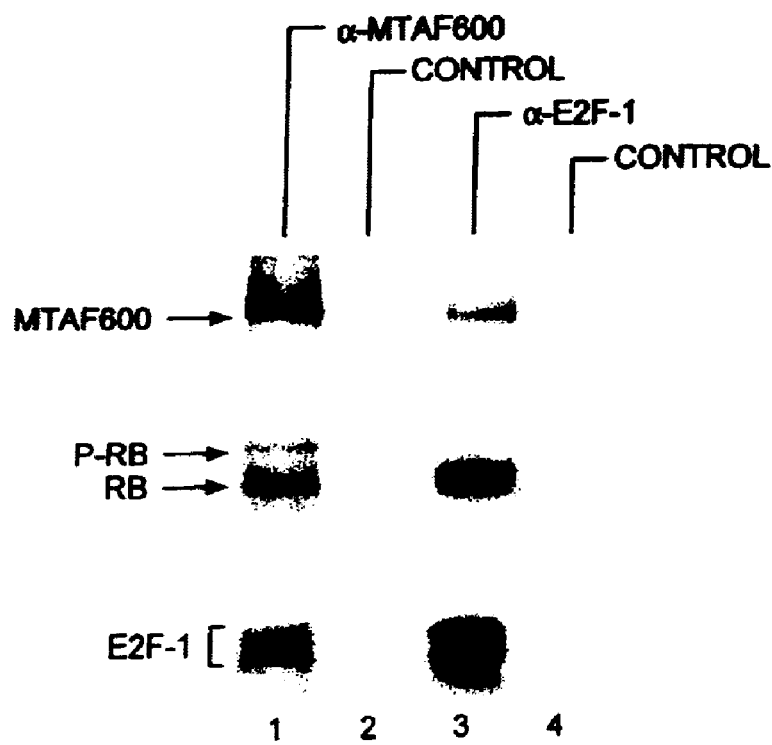
FIG. 2a shows that MTAF600 binds to both RB and E2F-1. HeLa nuclear extracts were immunoprecipitated with rabbit anti-MTAF600 polyclonal antibody and mouse anti-E2F-1 monoclonal antibody, respectively and MTAF600, RB, and E2F-1 in the immunoprecipitates were detected by immunoblotting. The positions of MTAF600, hyper- (P-RB) and hypo- (RB) phosphorylated RB, and E2F-1 are indicated. MTAF600 (lane 1) and E2F-1 (lane 3) Control rabbit IgG (lane 2) and Control mouse IgG (lane 4).

When MTAF600 was immunoprecipitated from a HeLa extract, both hypophosphorylated and hyperphosphorylated RB were copurified (FIG. 2A, lane 1). Moreover, E2F-1 was also immunoprecipitated along with MTAF600. We next performed reciprocal immunoprecipitation with anti-E2F-1 antibody (lane 3). As expected, only hypophosphorylated RB coprecipitated with E2F-1. Consistent with the reciprocal experiments, MTAF600 coprecipitated with E2F-1.

Figure 2B:
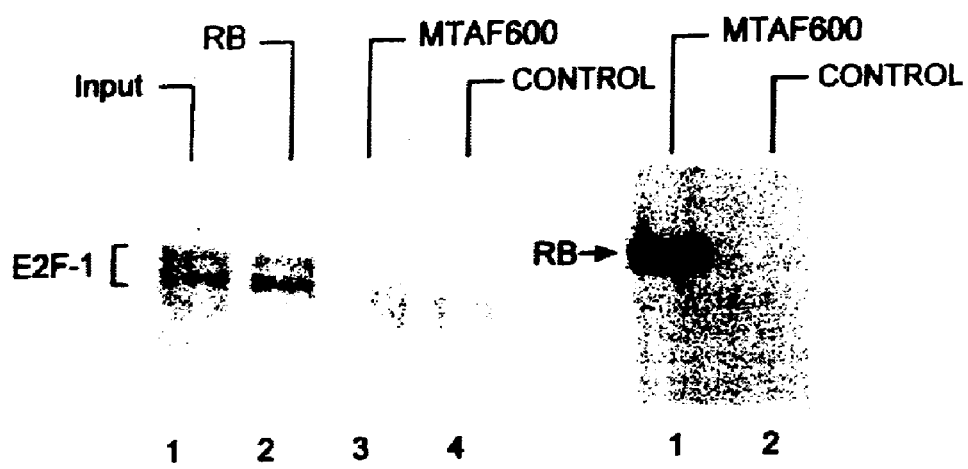
FIG. 2b shows that MTAF600 does not interact directly with E2F- 1. Left, GST-RB- (lane 2) and MTAF600- (lane 3) immobilized matrixes as well as control matrix (lane 4) were incubated with the E2F-1/DP complex. After washing, bound E2F-1 was detected by immunoblotting. 10% of the E2F-1/DP complex used for immunoprecipitation was also analyzed (lane 1). Right Panel, as a positive control for experiments shown in the left panel, MTAF600-immobilized (lane 1) and control matrixes were incubated with GST-RB. After washing, bound GST-RB was detected by immunoblotting.

Given that MTAF600 interacts with E2F-1, we tested whether the interaction of these factors is direct or indirect. GST-RB and MTAF600 immobilized on matrix were incubated with the purified E2F-1/DP complex to determine interaction (FIG. 2B, left). No detectable E2F-1 was retained on MTAF600 agarose (lane 3), while a considerable amount of E2F-1 was retained on GST-RB agarose. The control experiments showing that GST-RB binds to MTAF600 agarose demonstrate that the immobilized MTAF600 employed for these experiments is functional (FIG. 2B, right). Thus, these results exclude the direct interaction of MTAF600 with E2F-1. In all, we conclude that MTAF600 interacts with both hypophosphorylated and hyperphosphorylated RB, and further that MTAF600 interacts with RB without interfering RB binding to E2F-1.

Example 5

The Large Pocket Domain of RB is Responsible for Interaction with MTAF600

Figure 3A:
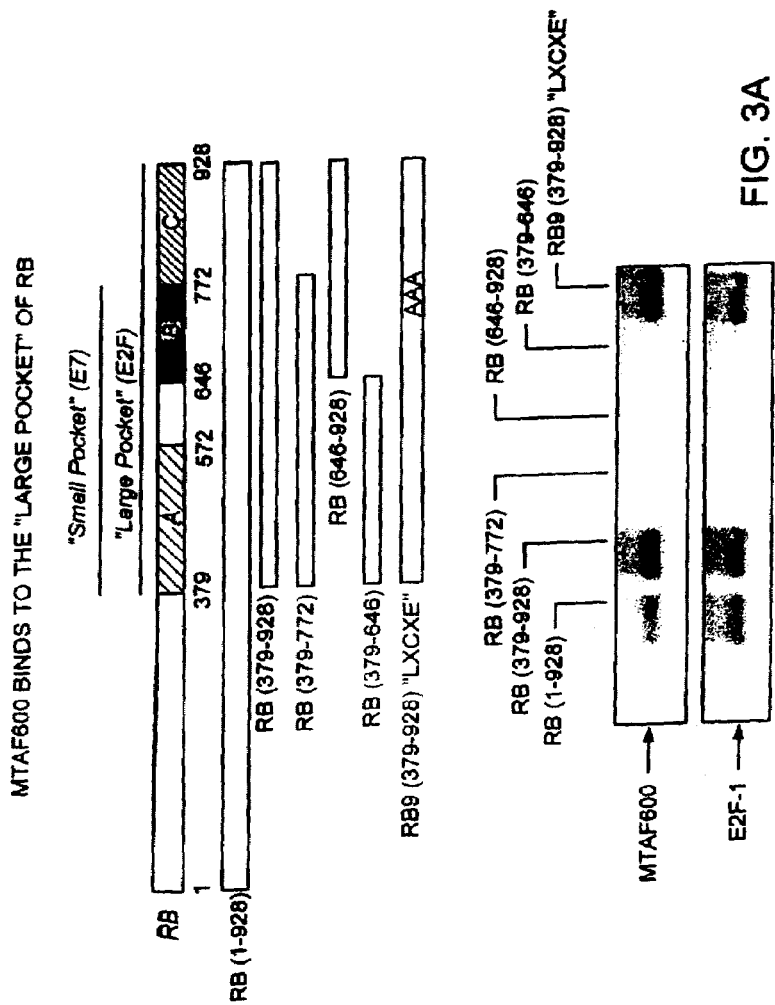
FIG. 3a is a schematic of RB constructs used for measuring interaction with MTAF600 and E2F-1. Positions of RB domains A, B, and C are indicated. The constructs that interact with MTAF600 are shaded. Numbers indicate amino acid position of RB from the N-terminus. RB9 is the triple alanine-substituted mutant (I753A, N757A, M761A) lacking LXCXE-binding activity (Dick et al., "Mutagenesis of the pRB pocket reveals that cell cycle arrest functions are separable from binding to viral oncoproteins", Mol. Cell. Biol., Vol. 20, pp. 3715–3727, 2000), whereas, R661W, C706F, and S567L are single substitution mutants derived from tumor (Kaye et al., "A single amino acid substitution results in a retinoblastoma protein defective in phosphorylation and oncoprotein binding", Proc. Natl. Acad. Sci. U.S.A., Vol. 87, pp. 6922–6926, 1990; Kratzke et al., "Functional analysis at the Cys706 residue of the retinoblastoma protein", J. Biol. Chem., Vol. 267, pp. 25998–26003, 1992; Yilmaz et al., "Twelve novel RB1 gene mutations in patients with hereditary retinoblastoma", Mutations in brief no. 206, Online. Hum. Mutat., Vol. 12, pp. 434, 1998).

To map RB sites required for MTAF600 binding, various RB constructs shown in FIG. 3A were expressed as GST fusions in *E. coli*.

Figures 1, 3B:
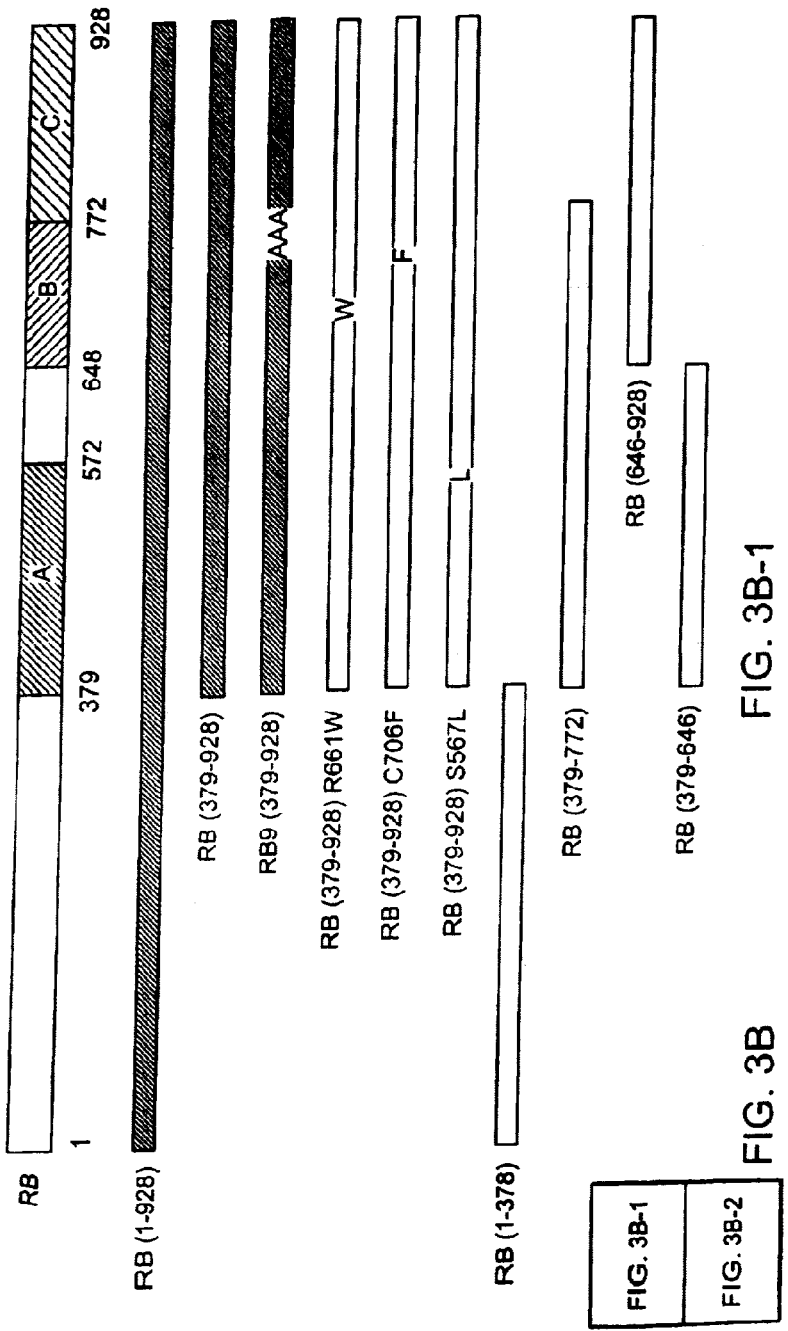
FIG. 3b shows the interaction of RB mutants with MTAF600. GST alone (lane 1) and RB-GST fusions (lanes 2–11) expressed in *E. coli* were incubated with a cell extract. After GST-pull down, bound MTAF600 and E2F-1 were detected by immunoblotting.
Figures 2, 3B:
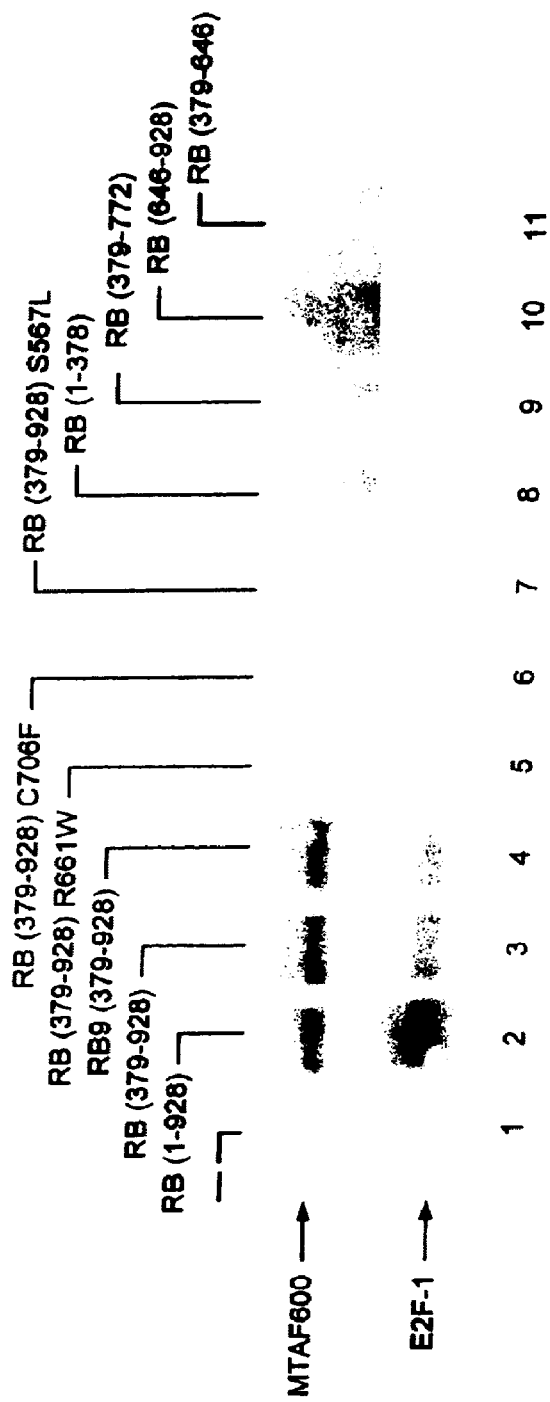
FIG. 2 shows the interaction of MTAF600 with RB and E2F-1.

The GST-RB fusions were incubated with HeLa nuclear extracts, and then bound MTAF600 and E2E-1 were analyzed by Western blotting after GST precipitation (FIG. 3B). The RB residues 379~928, referred to as RB (379~928), which encompass the large pocket domain, interacted with both MTAF600 and E2F-1. However, further deletions (379~772, 646~928, and 379~646, lanes 9~11) led to loss of interactions with MTAF600 and E2F-1, indicating that the large pocket domain of RB is required for interaction with both MTAF600 and E2F-1.

Viral transforming factors such as HPV E7, adenovirus E1A, and simian virus 40 large T antigen bind to RB through the conserved LXCXE motifs that are critical for transforming properties. (Reviewed in Zalvide et al., Mol. Cell. Biol., Vol. 15, pp. 5800–5810, 1995; Flint et al., Annu. Rev. Genet., Vol. 31, pp. 177–212, 1997). The LXCXE-binding sites are located within the B region (see FIG. 3A) and are well conserved among the RB family proteins. However, RB mutants lacking LXCXE-binding activity are still able to bind to E2F and repress transcriptional activity, indicating that binding of E2F to RB is independent of the LXCXE-binding sites. (Chen et al, Mol. Cell. Biol., Vol. 20, pp. 5571–5580, 2000; Dahiya et al., Mol. Cell. Biol., Vol. 20, pp. 6799–6805, 2000; Dick et al., Mol. Cell. Biol., Vol. 20, pp. 3715–3727, 2000). To test the requirement of the LXCXE-binding sites for MTAF600 interaction, we employed the RB mutant, RB9, (Dick et al., Mol. Cell. Biol., Vol. 20, pp. 3715–3727, 2000) which possesses 3 amino acid substitutions in the LXCXE contact surface and thus lacks the ability to bind to E7 or E1A. The large pocket domain of RB9 was expressed as a GST-fusion protein and tested for its ability to bind to MTAF600. Consistent to the previous report, (Dick et al., "Mutagenesis of the pRB pocket reveals that cell cycle arrest functions are separable from binding to viral oncoproteins", Mol. Cell. Biol., Vol. 20, pp. 3715–3727, 2000) RB9 interacted with E2F-1 as does wild-type RB. Likewise, RB9 also interacted with MTAF600 (FIG. 3B, lane 4). Almost equimolar amounts of GST proteins were recovered after GST pull-down.

In all, we conclude that both MTAF600 and E2F bind to the large pocket of RB independently of the LXCXE-binding sites. However, given that MTAF600 and E2F can simultaneously bind to RB (FIG. 2), these factors could target distinct surfaces of the large pocket of RB.

We next tested whether tumor-derived RB mutants (R661W, C706F, and S567L) (Kaye et al., Proc. Natl. Acad. Sci. U.S.A., Vol. 87, pp. 6922–6926, 1990; Kratzke et al., J. Biol. Chem., Vol. 267, pp. 25998–26003, 1992; Yilmaz et al, Mutations in brief no. 206, Online. Hum. Mutat., Vol. 12, pp. 434, 1998) bind to MTAF600 (FIG. 3B, lanes 5~7). Consistent with the previous reports, these mutants did not interact with E2F-1. (Kratzke et al., Oncogene , Vol. 9, pp. 1321–1326, 1994; Sellers et al., Genes Dev., Vol. 12, pp. 95–106, 1998) Importantly, none of these mutants showed interaction activity with MTAF600, suggesting that these mutations cause conformational alterations of RB, which lead to loss of interaction with MTAF600 and E2F-1.

We further tested whether the other RB family proteins p107 and p130 interact with MTAF600. The large pocket domain of RB, p107, and p130 were expressed as GST fusions and tested for interactions. As expected from sequence and functional conservations of the large pocket domain among RB family proteins, RB, p107, and p130 all interacted with MTAF600 in vitro (FIG. 3C).

Example 6

RB Binds to the MTAF600 Fragment with E7-like Sequence

Figure 5A:
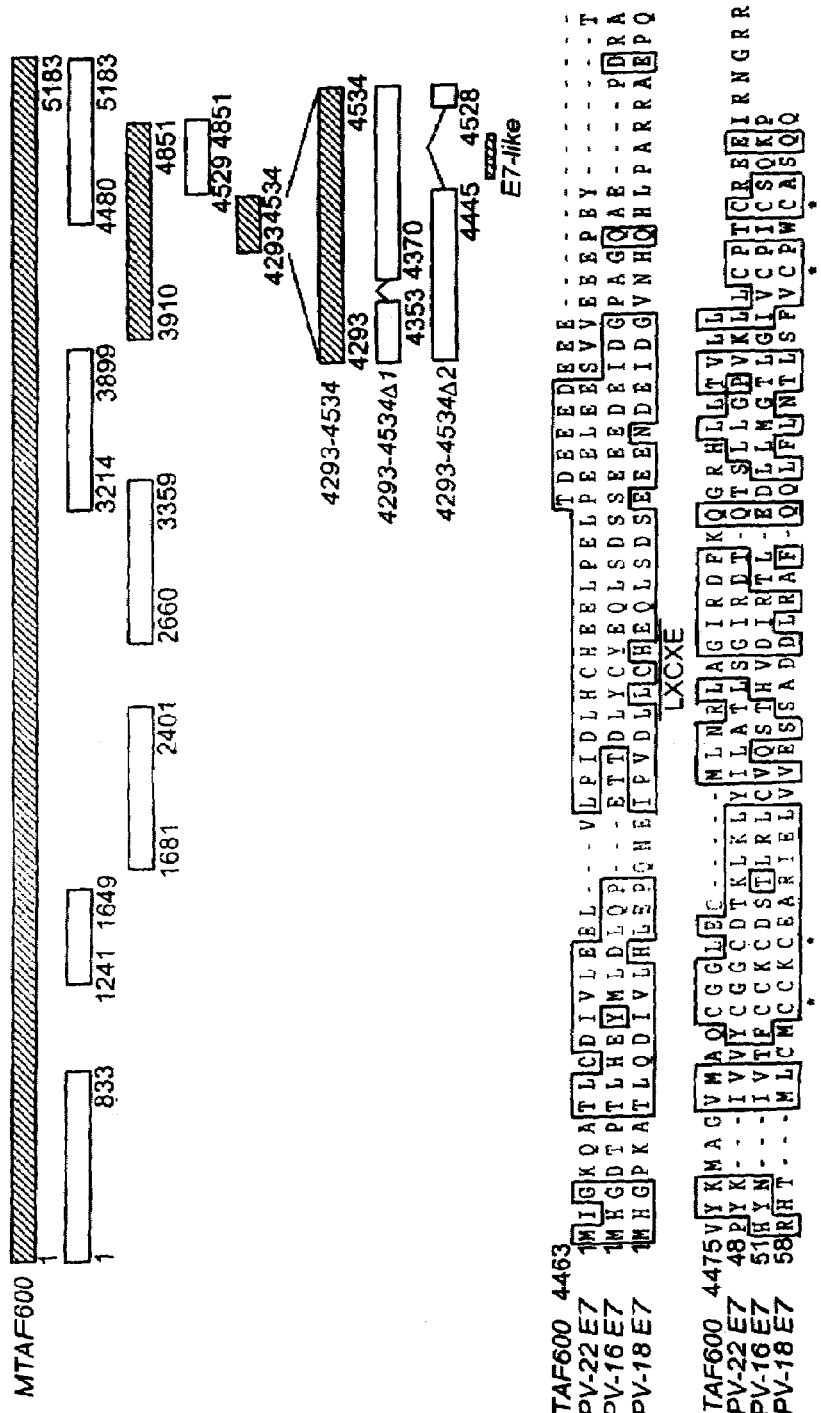
FIG. 5a provides a schematic of MTAF600 constructs used for interaction experiments. Top, the constructs that interact with RB are shaded. Numbers indicate the amino acid position of MTAF600 from the N-terminus. The region (residues 4463–4512) that possesses sequence similarity to human papillomavirus is indicated (top sequence; SEQ ID NO:2). Bottom, sequence alignment of MTAF600 with human papillomavirus E7 (types 16, 18, and 22), SEQ ID NOs 3–5, respectively. Conserved residues are shaded. The LXCXE motif and putative zinc finger domain (asterisks) of E7 are shown. Note that MTAF600 has no LXCXE motif.
Figure 5B:
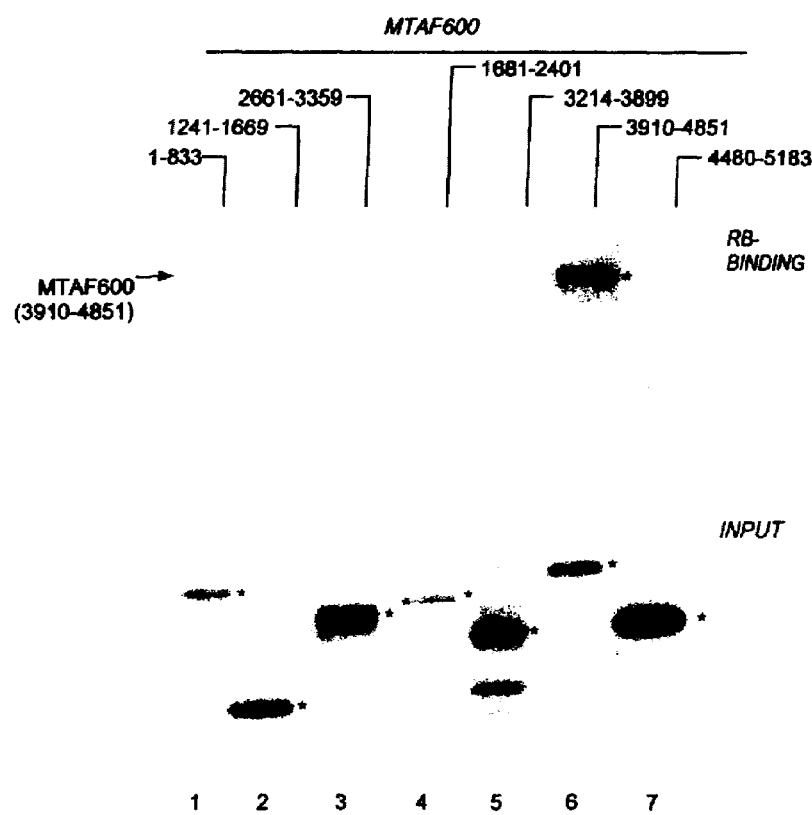
FIG. 5b shows the interaction of GST-RB with various MTAF600 fragments expressed in COS-7 cells. Various MTAF600 fragments indicated in the Figure were expressed as FLAG-tagged proteins by transfecting into COS-7 cells. Extracts prepared from transfected cells were incubated with recombinant GST-RB (379–928). MTAF600 fragments were analyzed by immunoblotting with anti-FLAG antibody before (bottom) and after (top) GST-pull down. Immunoreactive bands that correspond to estimated molecular weights are indicated by asterisks.

To determine MTAF600 sites that are responsible for RB interaction, various MTAF600 fragments (1~833, 1241~1649, 1681~2401, 2660~3359, 3214~3899, 3910~4851, and 4480~5183; FIG. 5A) were expressed as FLAG-tagged proteins by transfecting into COS-7 cells. Extracts containing recombinant MTAF600 fragments were prepared from resulting cells and tested for GST interaction. As shown in FIG. 5B, only MTAF600 (3910~4851) interacted with RB in vitro. This interaction was confirmed in COS-7 cells by immunoprecipitation of exogenously expressed MTAF600 (3910~4851) and RB.

Figure 5C:
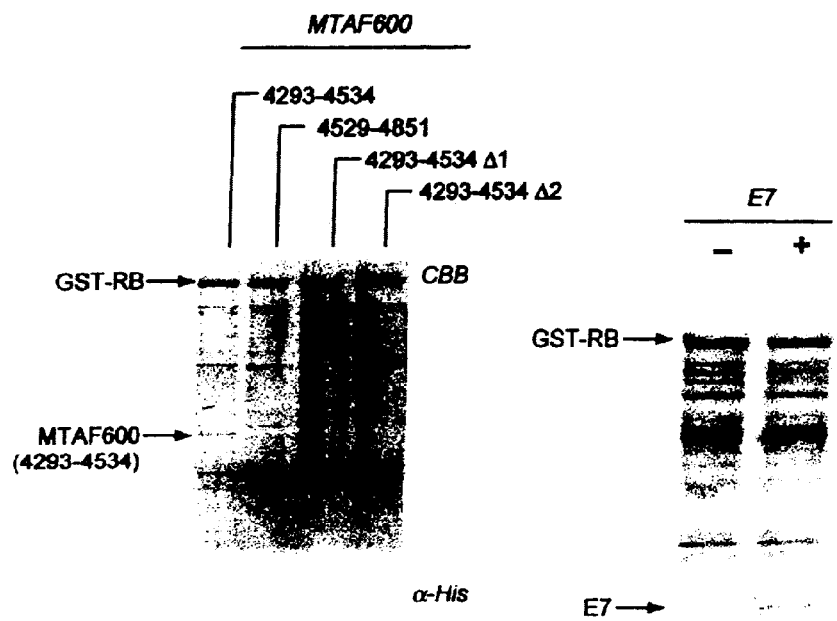
FIG. 5c shows the fine mapping of the RB-binding sites with bacterially expressed MTAF600 fragments. The MTAF fragments were expressed as His-tagged proteins in *E. coli* and incubated with recombinant GST-RB (379–928). After GST pull-down, proteins were detected by Coomassie brilliant blue R250 staining (top) or immunoblotting with anti-His antibody (middle). His-tagged proteins before GST pull-down were also analyzed by immunoblotting. Immunoreactive bands that correspond to estimated molecular weights are indicated by asterisks.
Figure 5D:
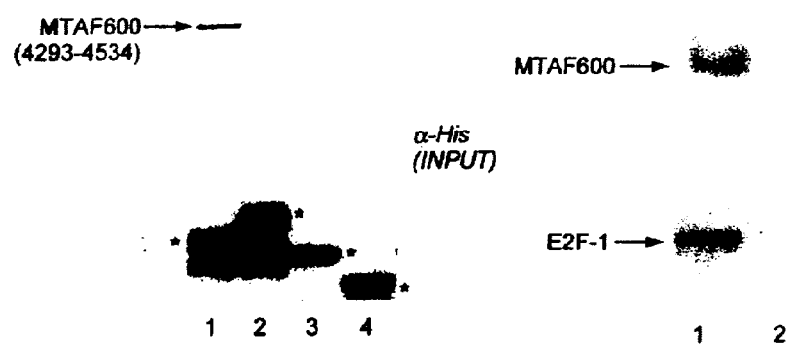
FIG. 5d shows that E7 inhibits binding of RB with MTAF600 as does E2F-1. GST-RB (379–928) was pre-incubated with (lane 2) and without (lane 1) recombinant HPV-16 E7. After GST pull-down, samples were resolved by SDS-PAGE and stained with Coomassie brilliant blue R250, confirming that the interaction between RB and E7 is stoichiometric (top). GST-RB (379–928) on matrix with and without pre-binding of E7 was incubated with a cell extract prepared from NIH3T3 cells. After washing, bound proteins were detected by immunoblotting with anti-MTAF600 (middle) and anti-E2F-1 antibodies (bottom).

For more precise mapping of the MTAF600 sites required for RB-binding, further deletions were introduced in the MTAF600 residues 3910~4851 and were expressed as His-tagged proteins in E. coli (FIG. 5C). The MTAF600 (4293~4534) interacted with RB (lane 1), while MTAF600 (4529~4851) did not (lane 2). Importantly, binding of the MTAF600 (4293~4534) with RB is almost stoichiometric judging from the Coomassie brilliant blue-stained SDS-PAGE gel. On the other hand, the internal deletions (Δ1 and Δ2; FIG. 5A) within MTAF600 (4293~4534) resulted in loss of interaction (FIG. 5C, lanes 3 and 4).

A BLAST database search with the RB-binding domain of MTAF600 as query revealed that the MTAF600 residues, located within the essential region for RB-binding, possess sequence similarity to HPV E7 (FIG. 5A). While HPV-22 (type 22) E7 shows the best conservation, E7 of HPV-16 and -18, high-risk types which link to subset of malignant tumors, (For reviews, see Flint et al., "Viral transactivating proteins", Annu. Rev. Genet., Vol. 31, pp. 177–212, 1997) also display significant conservations. The conservation is observed in E7 residues 27–77 (based on the HPV-22 E7 sequence) adjacent to the LXCXE motif. While the LXCXE motif of E7 is sufficient for specific binding to RB, (Lee et al., Nature, Vol. 391, pp. 859–865, 1998 and therein) the contiguous C-terminal region is responsible for stable binding to RB and transforming activity. (For review, see Flint et al., Annu. Rev. Genet., Vol. 31, pp. 177–212, 1997) (see Discussion). The sequence similarity between E7 and the RB binding domain of MTAF600 suggests that E7 and MTAF600 bind competitively to RB. GST-RB was pre-incubated with E7 (FIG. 5D) and then tested for interaction with MTAF600. As predicted, pre-incubation of RB with E7 significantly reduced binding of both MTAF600 and E2F-1, suggesting that not only E2F-1 but also MTAF600 are targeted by E7.

Example 7

MTAF600 Functions as a Corepressor of RB

An important role of RB is negative regulation of E2F-dependent transcription, allowing repression of various genes required for S-phase entry. (For reviews, see Weinberg, "The retinoblastoma protein and cell cycle control", Cell, Vol. 81, pp. 323–330, 1995, Dyson, "The regulation of E2F by pRB-family proteins", Genes Dev., Vol. 12, pp. 2245–2262, 1998) Recent studies have shown that RB does not simply neutralize the function of E2F activation domain; instead, RB functions as an active repressor when RB in recruited on E2F-dependent promoters via interaction with E2F, and thus, deletion of E2F-binding sites results in gene activation in some promoters. (Neuman et al., "Transcription of the E2F-1 gene is rendered cell cycle dependent by E2F DNA-binding sites within its promoter", Mol. Cell. Biol., Vol. 14, pp. 6607–6615, 1994). Because formation of the stoichiometric complex between RB and MTAF600 suggest that functions of RB, at least in part, could be contributed by MTAF600, we tested whether MTAF600 contributes to transcriptional repression by RB.

Figures 6A, 6B:
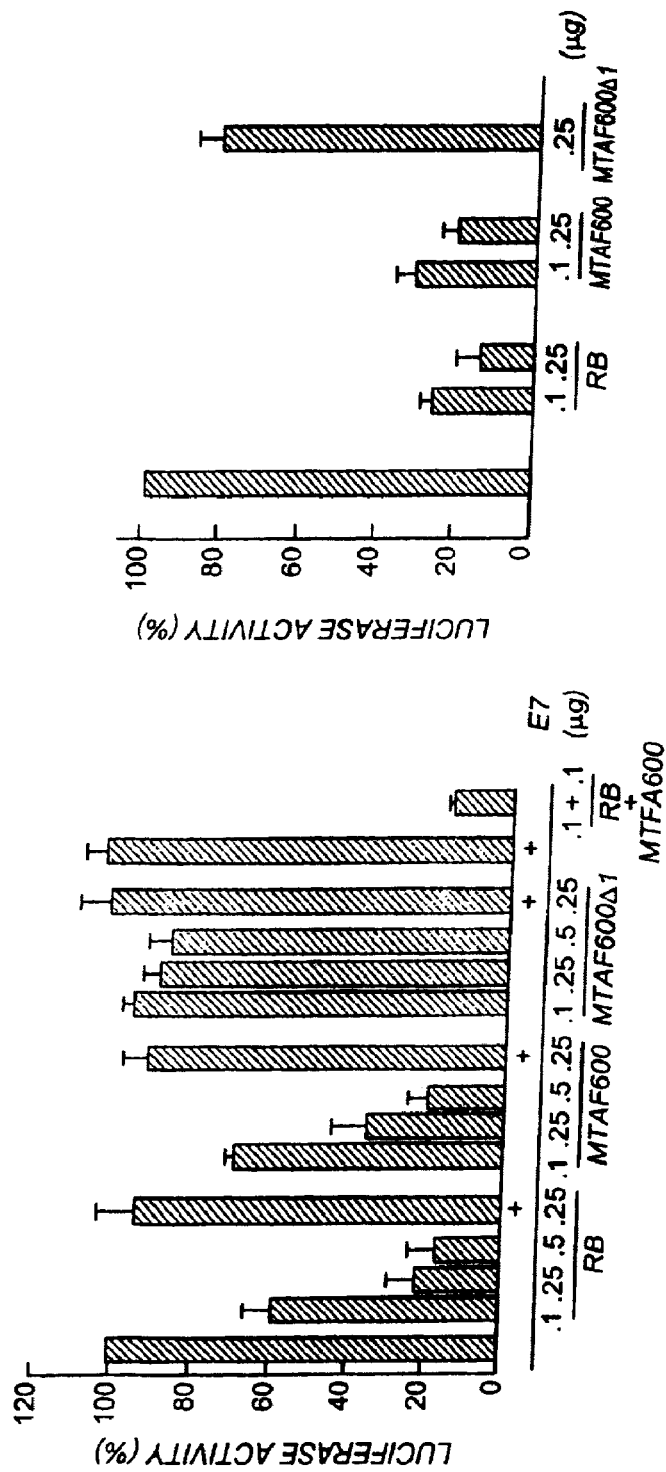
FIG. 6(a) shows that MTAF600 (3910–4851) represses E2F-responsive promoter activity in U2OS osteosarcoma cells.
FIG. 6(b) MTAF600 (3910–4851) actively represses E2F-1 promoter activity.

We first tested a luciferase reporter gene driven by three E2F-binding sites linked to the TK core promoter. (Magnaghi-Jaulin et al., Nature, Vol. 391, pp. 601–605, 1998). In FIG. 6A, U2OS cells were transiently transfected with the 3×E2F-TK-luciferase reporter (0.5 mg) (Magnaghi-Jaulin et al., Nature, Vol. 391, pp. 601–605, 1998) and expression vectors for RB, MTAF600 (3910–4851), MTAF600 (3910–4851)D1, and HPV-16 E7 (0.1 mg) as indicated. All transfection mixtures include 0.1 mg of CMV-β-galactosidase reporter, which is not under regulation of E2F, for normalization of transfection efficiency. After 48 hr of transfection, cells were harvested and processed for reporter assays. Luciferase activity is plotted as relative activity±standard division after normalizing against b-galactosidase activity. The control reporter construct lacking E2F-binding sites displayed <5% of the activity displayed by the 3×E2F-TK-luciferase reporter.

Strong transactivation from this reporter was observed by endogenous E2F in U2OS cells in an E2F-binding site-dependent manner (FIG. 6A). This activation was inhibited by co-transfecting RB in a dose-dependent manner. Likewise, co-transfection of MTAF600 (3910~4851) significantly inhibited E2F-dependent transcription. In addition to MTAF600 (3910–4851), MTAF600 (4300–4534) similarly inhibited E2F-dependent transcription. Inhibition of E2F-dependent transcription by MTAF600 (3910–4851) appears to be dependent on endogenous RB family proteins, since the MTAF600 mutant lacking RB-binding activity, MTAF600 (3910–4851)Δ1, did not inhibit E2F-dependent transcription. Moreover, HPV E7 counteracted inhibitory activity by MTAF600 (3910–4851). This shows that a likely pathway for the role of MTAF600 in E2F-dependent transcription is through interaction with RB.

To explore the role of MTAF600 in active repression, we employed the E2F-1 promoter linked to a luciferase reporter gene (FIG. 6B). Experiments were performed as described above except that a luciferase reporter under regulation of the E2F-1 promoter was employed.

The E2F-1 promoter has putative binding sites for E2F, Sp-1, ATF, E4F, and NF-κB (Neuman et al., Mol. Cell. Biol., Vol. 14, pp. 6607–6615, 1994). Given that mutation in the E2F-binding sites leads to derepression of the promoter activity during G1In the E2F-1 promoter, the E2F-binding sites must play a role in active repression of transcription. The E2F-1-luciferase gene was strongly expressed by endogenous transcription factors in U2OS cells. Importantly, this activation was efficiently repressed by transfecting either RB or MTAF600 (3910–4851). However, the activity was not inhibited by the MTAF600 mutant lacking RB binding activity, MTAF600 (3910–4851)Δ1. These results indicate that MTAF600 (3910–4851) contributes to active repression of the E2F-1 promoter in conjunction with endogenous RB family proteins.

To explore whether MTAF600 inhibits E2F-mediated transcription in RB-deficient cells, we employed wild type and RB-deficient NIH3T3 fibroblasts. (Classon et al., Proc. Natl. Acad. Sci. U.S.A., Vol. 97, pp. 10820–10825, 2000). FIGS. 6c and 6d show results obtained when experiments were performed as described for FIG. 6a except that RB+/+ (FIG. 6C) and RB−/− (FIG. 6D) 3T3 fibroblasts were employed (Classon et al, Proc. Natl. Acad. Sci. U.S.A., Vol. 97, pp. 10820–10825, 2000).

Figure 4A:
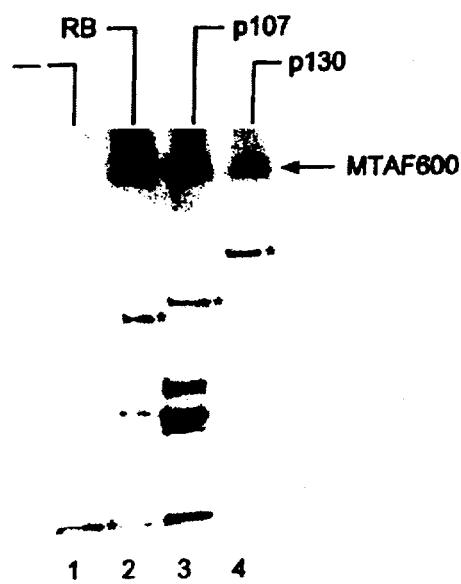
FIG. 4a shows that MTAF600 interacts with all RB family members in vitro. The large pocket domains of RB (lane 2), p107 (lane 3), and p130 (lane 3) were expressed as GST-fusions. These fusions as well as GST control (lane 1) were incubated with a HeLa nuclear extract and purified by GST pull-down. Bound MTAF600 (top) and GST proteins (bottom) were analyzed by immunoblotting with anti-MTAF600 and anti-GST antibodies, respectively.
Figure 4B:
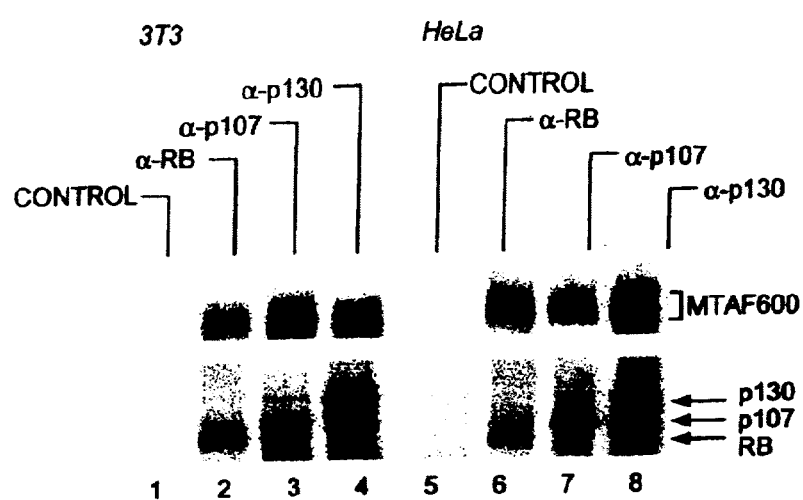
FIG. 4b shows that MTAF600 interacts with all RB family members in vivo. Immunoprecipitation experiments were carried out from 3T3 (lanes 1~4) and HeLa (lanes 5~8) extracts with control (lanes 1 and 5), RB (lanes 2 and 6), p107 (lanes 3 and 7), and p130 (lanes 4 and 8) antibodies. Immunoprecipitated materials were analyzed by immunoblotting with anti-MTAF600 antibody (top) and a mixture of anti-RB, anti-p107, and anti-p130 antibodies (bottom).

Given that only weak transactivation from this reporter was observed by endogenous E2F in NIH3T3 fibroblasts, we cotransfected E2F-1 expression vector to study the repressive effect (FIGS. 6C and D). In both wild type and RB-deficient NIH3T3 fibroblasts, MTAF600 (3910–4851) repressed E2F-mediated transcription, although repression is less effective in the RB-deficient fibroblasts. Whereas, MTAF600 mutant lacking RB binding activity did not, suggesting that MTAF600 silences E2F-mediated transcription in collaboration with p107 and/or p130 in the RB-deficient fibroblasts. These results support the data showing binding of MTAF600 to all RB family members (FIG. 4).

Example 8

MTAF600 Inhibits Cell Proliferation

We examined whether expression of MTAF600 (3910–4851) leads to inhibition of S-entry of the cell cycle. Stably transfected U2OS cells were synchronized at G0/G1 by contact inhibition. In the control cells, 64% of the cells were in S-phase at 24 hr after induction of cell growth by replating. In contrast, in the cells expressing MTAF600 (3910–4851), G0/G1 cells were predominant and only 37% of the cells were found in S-phase after 24 hr. On the other hand, no significant delay in entering S-phase was observed in cells expressing the mutant form of MTAF600 (3910–4851), although expression level of the mutant protein was comparable to that of the wild-type MTAF600 (3910–4851) (data not shown). From these results, we conclude that exogenous expression of MTAF600 (3910–4851) inhibits progression of cells into S-phase in collaboration with endogenous RB family proteins.

Figure 7A:
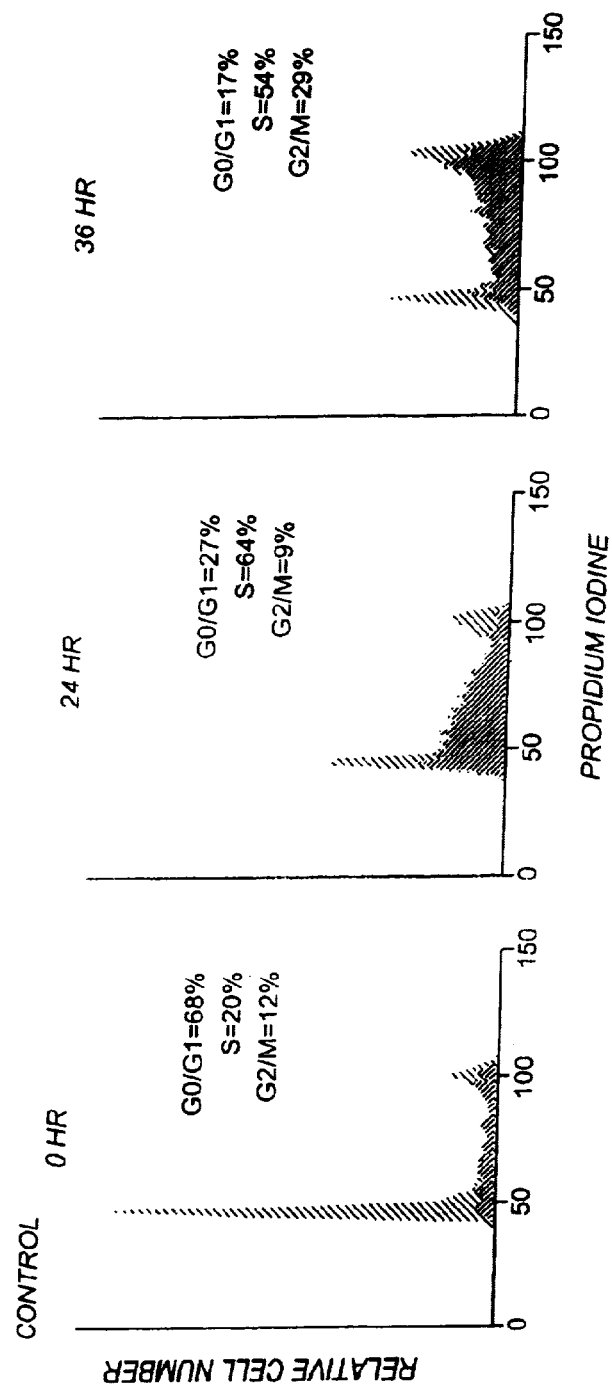
FIG. 7 shows that MTAF600 is involved in cell cycle arrest mediated by RB family members.
Figure 7B:
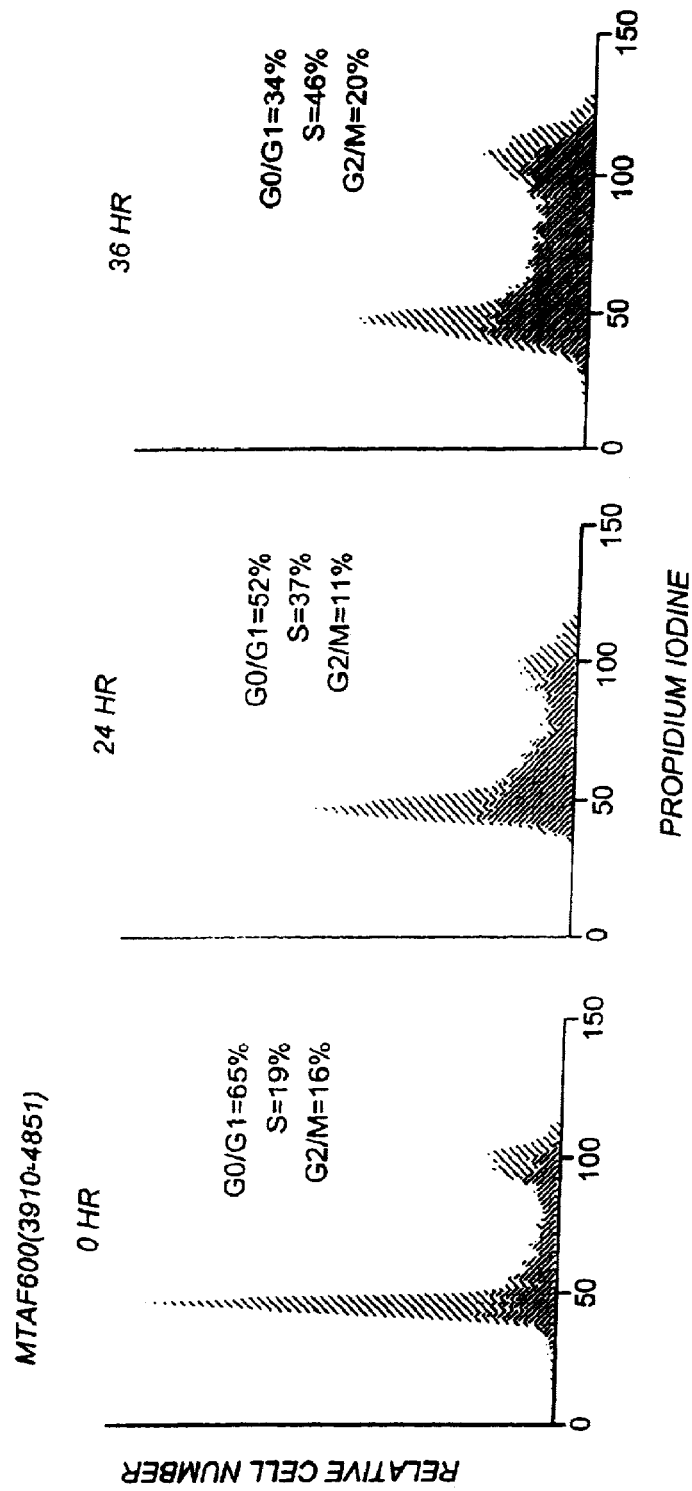
Figure 7C:
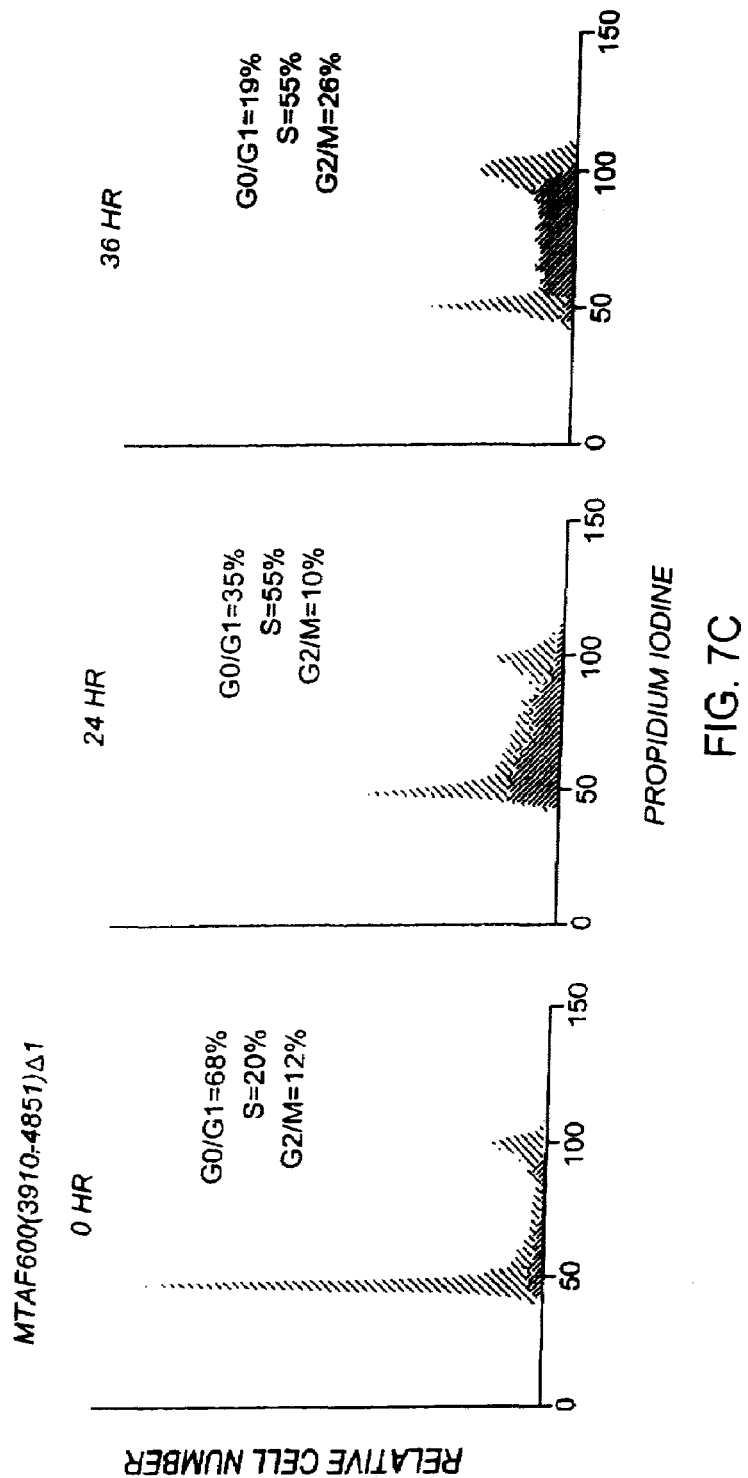

In other experiments, U2OS cells were stably transfected with the expression vectors for MTAF600 (3910–4851) and MTAF600 (3910–4851) D1, as well as the control vector, and were synchronized at G0/G1 by contact inhibition. Cells were replated and harvested at 0, 24, and 36 hrs. Cell cycle stage was analyzed by FACS, as indicated in FIG. 7, which shows that MTAF600 is involved in cell cycle arrest mediated by RB family members.

Figure 8:
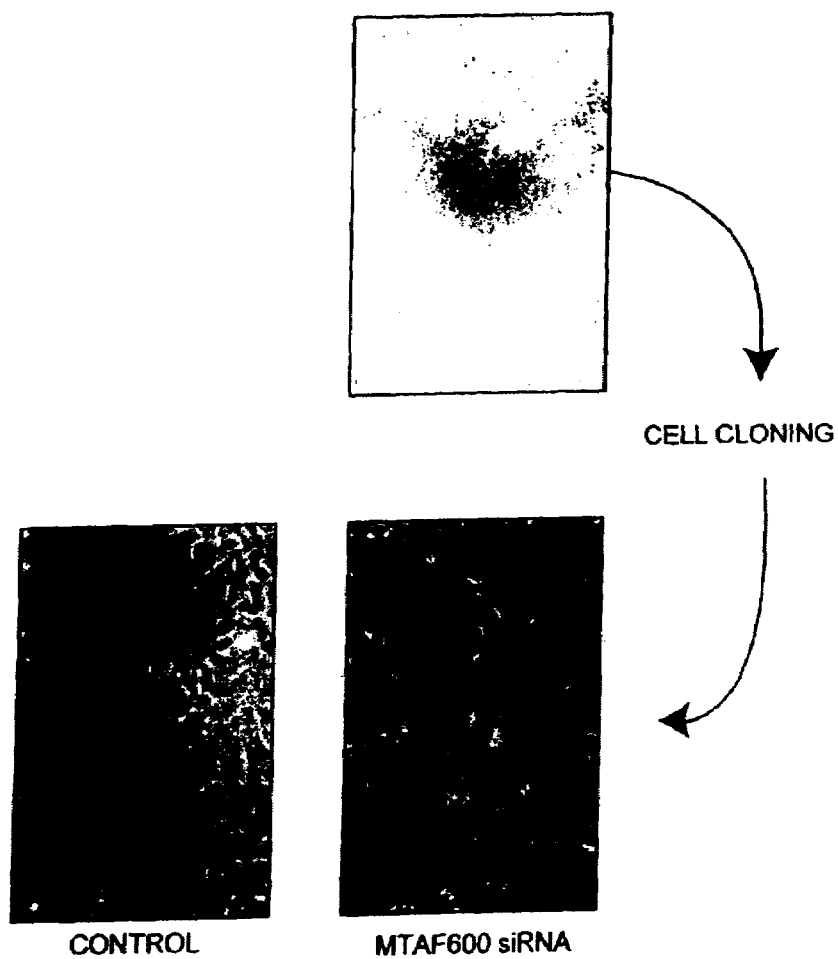
FIG. 8 shows how loss of MTAF600 induces transformation in NIH 3T3 fibroblasts using MTAF600 siRNA to knock out the expression of MTAF600 as determined by observation of the cell culture by microscopy.

Using MTAF600 siRNA to knock out the expression of MTAF600, FIG. 8 shows how loss of MTAF600 induces transformation in NIH 3T3 fibroblasts, as determined by observation of the cell culture by microscopy.

Figure 9:
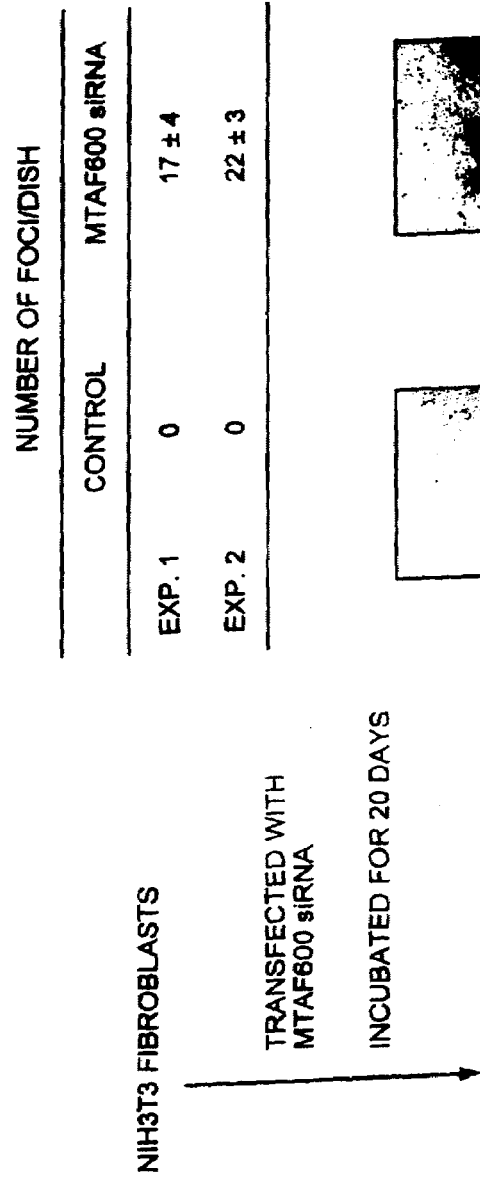
FIG. 9 shows how down-regulation of MTAF600 induces formation of "micro-foci" in NIH 3T3 fibroblasts, as determined by foci/dish.

Using foci/dish analysis, down-regulation of MTAF600 was found to induce formation of "micro-foci" in NIH 3T3 fibroblasts, as shown in FIG. 9.

Figure 10:
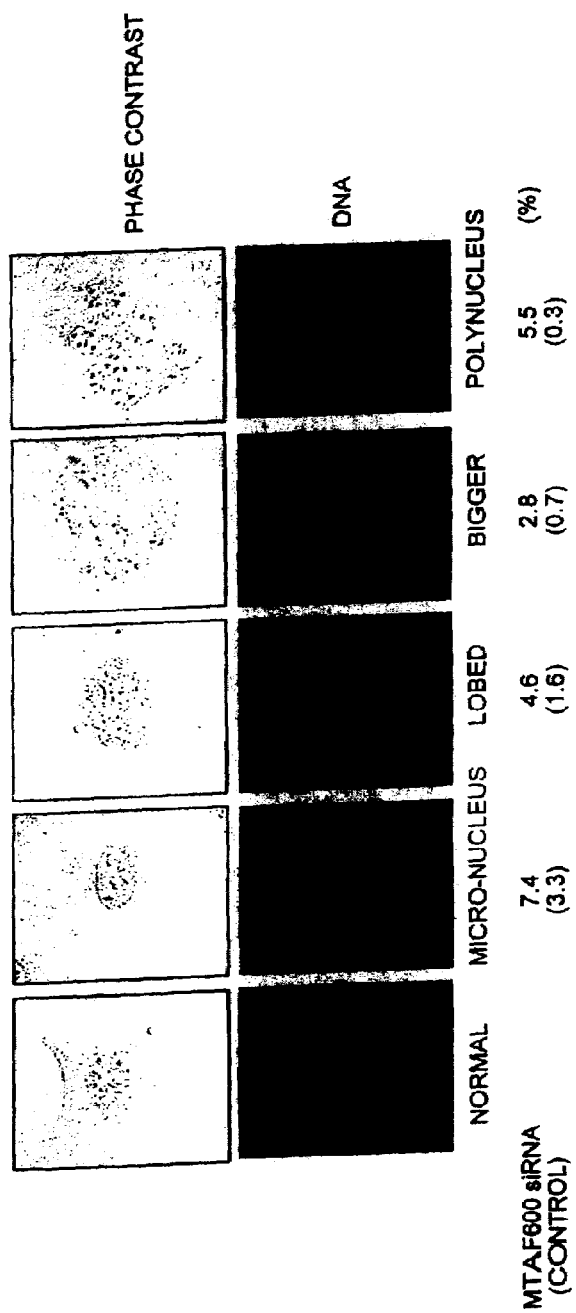
FIG. 10 shows how loss of MTAF600 results in formation of polynucleated cells resulting from inhibition of cytokinesis using phase microscopy and fluorescent microscopy.

Phase microscopy and fluorescent microscopy was used to examine the effect of loss of MTAF600 on cytokinesis. As seen in FIG. 10, the loss of MTAF600 results in inhibition of cytokinesis and formation of polynucleated cells, when compared to normal cells.

Figure 11:
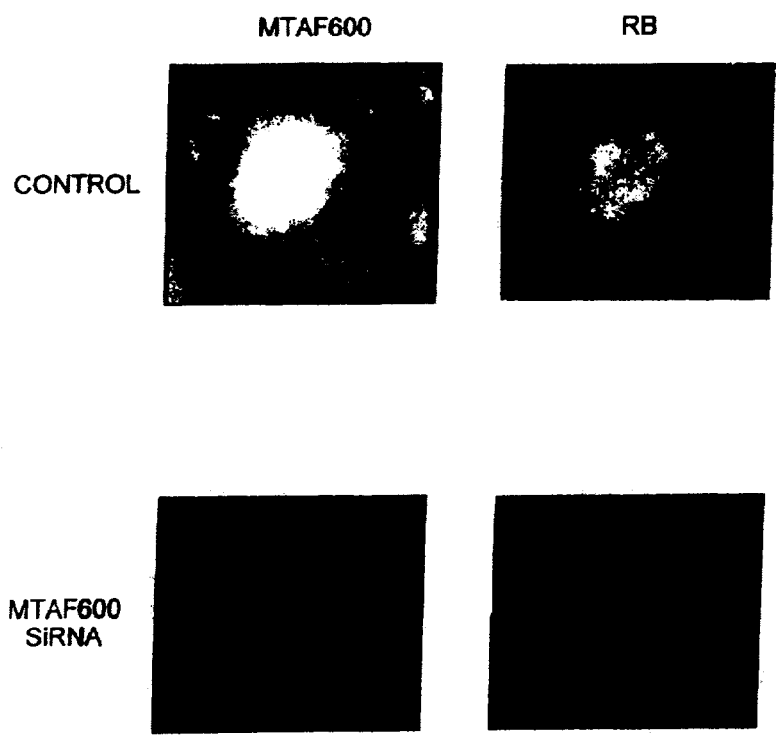
FIG. 11 shows the effect of loss of MTAF600 on alignment of chromosomes along the spindle in replicating cells.

Determination of the effect of loss of MTAF600 on alignment of chromosomes along the spindle in replicating cells is shown in FIG. 11. Green represents MTAF600 protein which is present in the control cells and absent in MTAF600 SiRNA cells. In the control cells, RB is organized in the nucleus whereas in the MTAF600 SiRNA treated cells, RB is dispersed. Red is RB protein, Blue is DNA.

Figure 12:
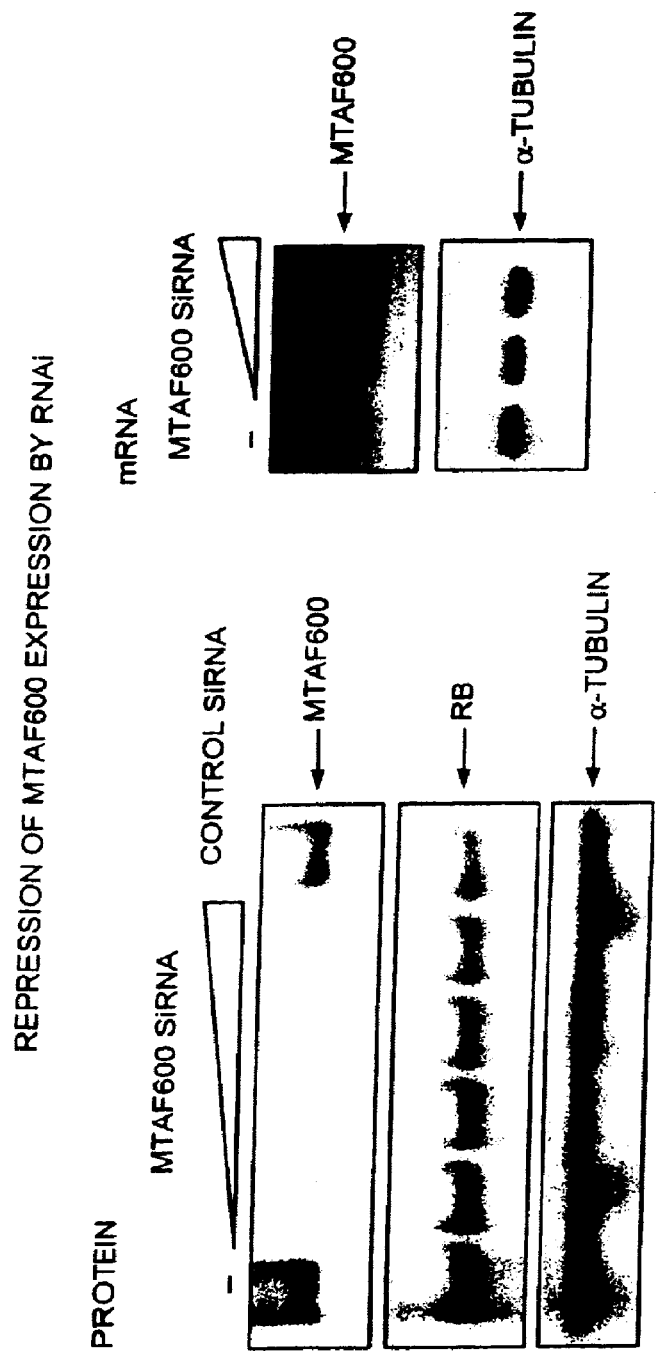
FIG. 12 shows a gel in which increased amounts of MTAF600 siRNA associated with decreased MTAF600 protein does not alter amounts of RB protein or alpha tubulin in cells. This correlates with levels of MTAF600 RNA and alpha tubulin RNA.

As seen in FIG. 12, increased amounts of MTAF600 siRNA associated with decreased MTAF600 protein does not alter amounts of RB protein or alpha tubulin in cells, as determined by PAGE analysis. This correlates with levels of MTAF600 RNA and alpha tubulin RNA.

Localization of MTAF600 at the Kinetochore of the nucleus is shown in FIG. 13. Dynein, shown in red, binds to the microtubule and uses the energy in ATP molecules to move from the positive (+) end of the microtubule (where new tubulin dimers are adding to the microtubule) toward the minus (−) end of the microtubule. Each small step requires the hydrolysis of one ATP molecule. Dynein pulls subcellular materials toward the center of the cell, or in the case of mitosis, toward the poles of the spindle and thus toward the centers of the two new daughter cells. Fluorescent staining reveals the colocalization of MTAF600 with Dynein.

Telephase colocalization of MTAF600 with alpha tubulin along the spindle is seen in FIG. 14. Localization of MTAF600 is enhanced in the green/blue image, compared to α-tubulin enhancement in the red/blue image, followed with the merged image (yellow/red/blue/green).

Co-localization of MTAF600 and RB with microtubules during Metaphase is shown in FIG. 15. MTAF600 enhancement is shown in the green/blue image; RB enhancement is shown in the red/blue image; and the merge image is seen with yellow.

Co-localization of MTAF600 with alpha tubulin along the spindle in metaphase is shown in FIG. 16. MTAF600 enhancement is shown in green, α-tubulin enhancement is shown in red, and the merged image is shown in yellow.

Association of MTAF600 with microtubules, specifically α-tubulin, during interphase, is shown in Figure. MTAF600 enhancement is shown in green; α-tubulin enhancement is shown in red; and the merged image is shown in yellow.

FIG. 18 shows Protein binding domains in the MTAF600 amino acid sequence are shown in FIG. 18. A zinc finger domain is found in the 1650–1730 region of the sequence, in yellow; a calmodulin (CaM) binding domain is found at region 4076–4122, in green; and a retinoblastoma (RB) binding domain is found at the 4293–4534 region of the sequence, in red.

Figure 19:
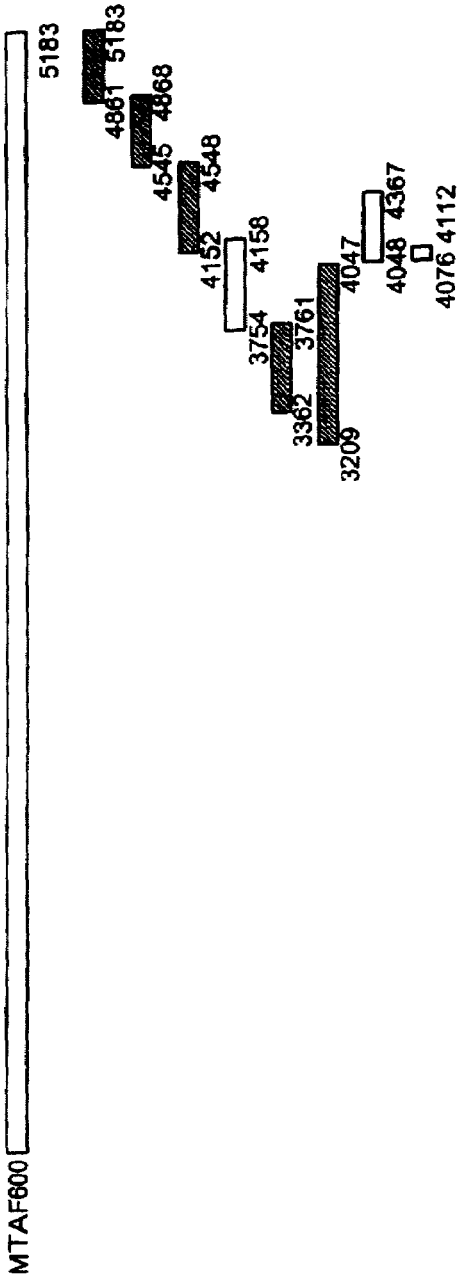
FIG. 19 shows calmodulin binding sites mapped on the MTAF600 amino acid Sequence (SEQ ID NO:6).

Calmodulin (CaM) binding sites are mapped on the MTAF600 amino acid sequence in FIG. 19. The 4089 to 4112 region is expanded, to show the actual amino acid sequence in that region.

Figure 20:
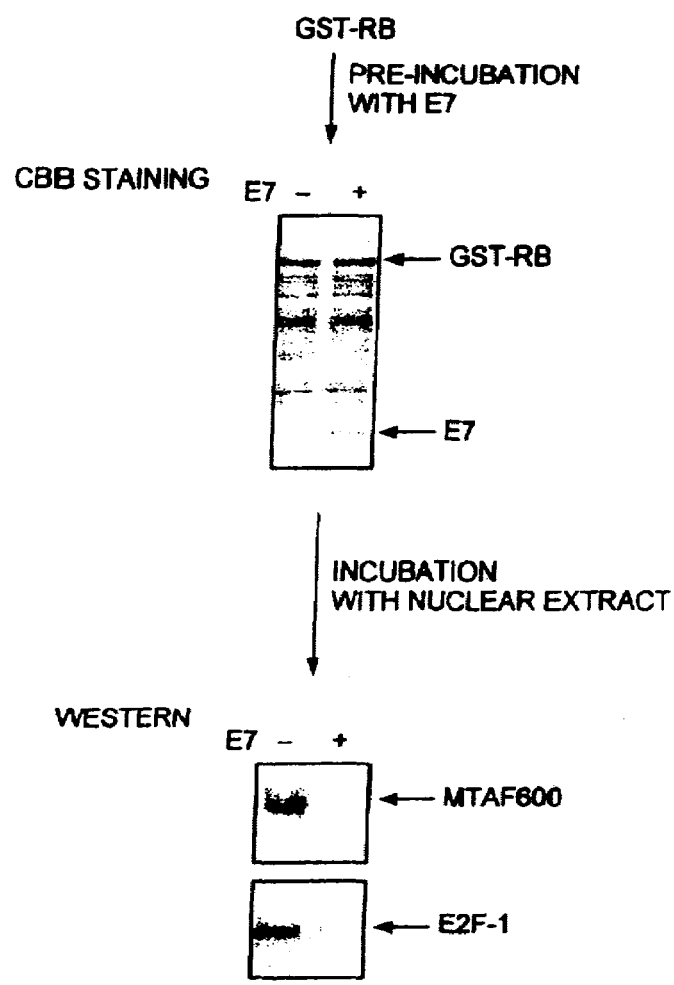
FIG. 20 shows how E7 inhibits binding of MTAF600 to RB.

E7 inhibition of MTAF600 binding to RB is shown in FIG. 20. Coomasie brillian blue staining indicates the presence of a GST-RB fusion protein band in the presence and absence of E7, as well as a band for E7 in the E7 lane, and Western blot analysis shows the complete absence of an MTAF600 band or an E2F-1 band in the presence of E7 after incubation with nuclear extracts.

Figure 21:
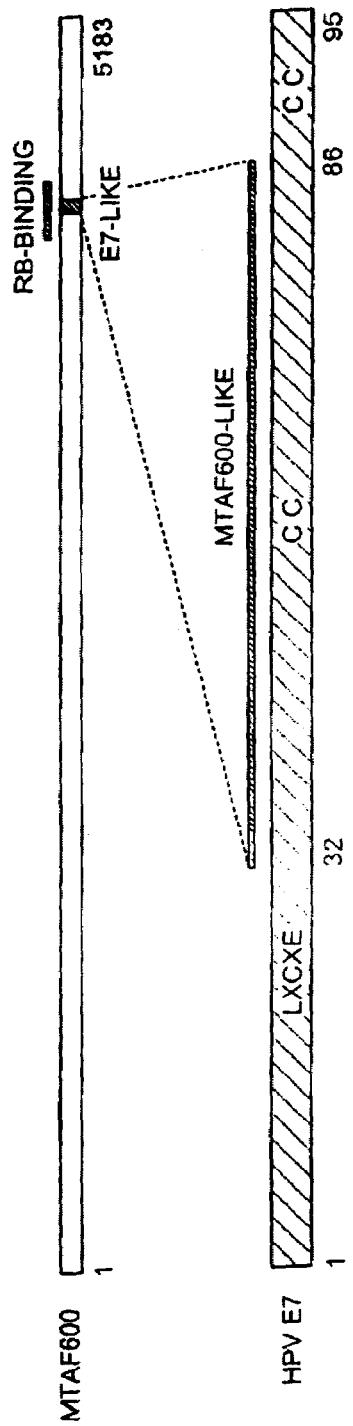
FIG. 21 shows how the RB-binding domain (SEQ ID NO:2) of MTAF600 has sequence similarity to E7 (SEQ ID NO:4) comparing amino acid sequences.

Similarity of the RB-binding domain of MTAF600 with E7 is shown in FIG. 21, where the amino acid sequences of the two proteins are compared. MTAF600 is shown in red, and E7 is shown in blue. The E7-like and MTAF600-like similar sequences are indicated generally in yellow, and the specific sequences for the MTAF600 E7-like region and the relevant E7 segment are shown below with specific amino acid matches highlighted in red.

Figure 22:
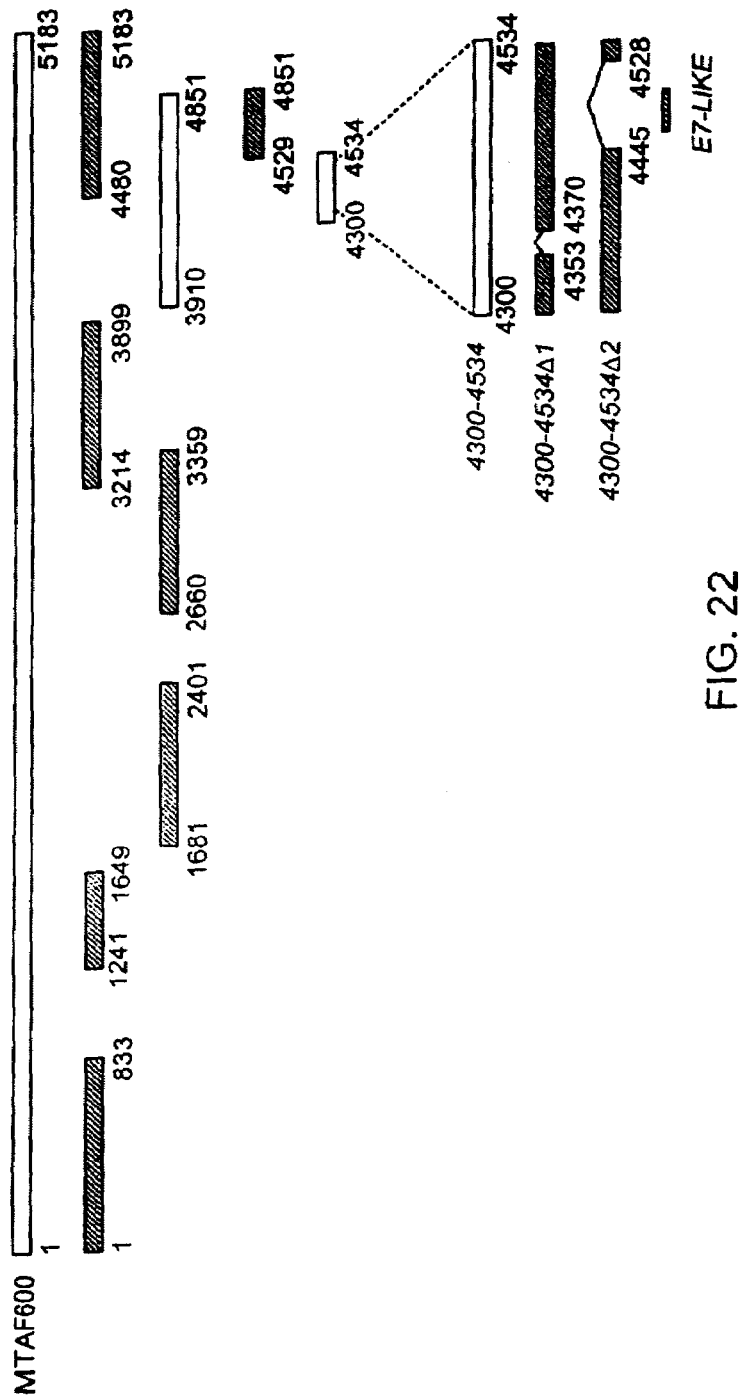
FIG. 22 shows how the RB-binding domain of MTAF600 has sequence similarity to E7.

The RB-binding domain of MTAF600, and its sequence similarity to E7, is shown generally in FIG. 22, with the E7-like region highlighted in yellow.

Figure 23:
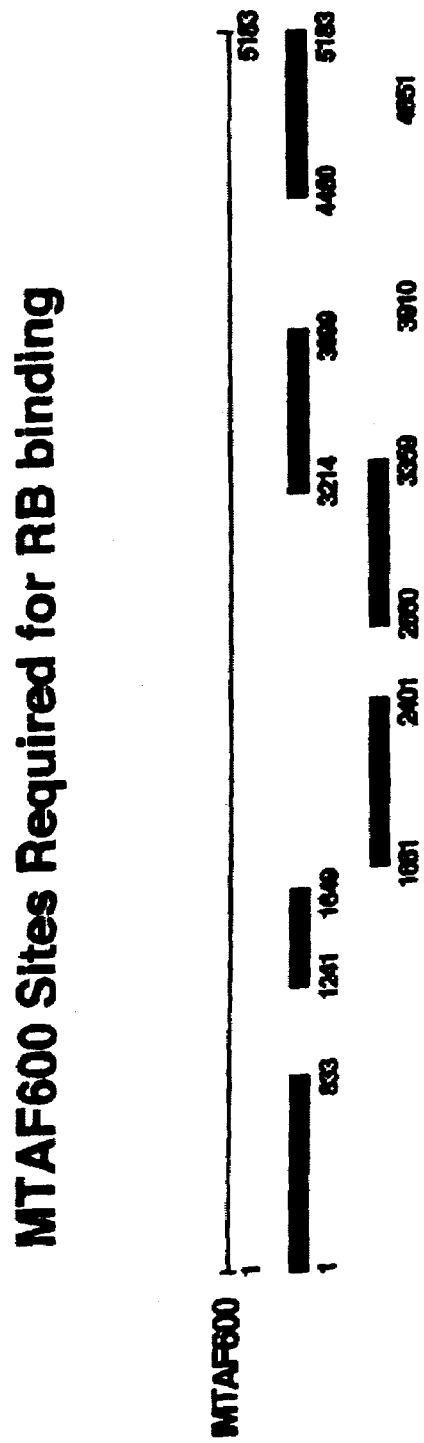
FIG. 23 shows how MTAF600 sites are required for RB binding.

MTAF600 sites required for RB binding are shown in FIG. 23.

What is claimed is:

1. An isolated nucleic acid molecule comprising a nucleotide sequence encoding a polypeptide comprising SEQ ID NO:1.

2. The isolated nucleic acid molecule of claim 1 wherein the polypeptide consists of SEQ ID NO:1.

3. A vector comprising any of the isolated nucleic acid molecules of claims 1 and 2.

4. An expression vector comprising any of the isolated nucleic acid molecules of claims 1 and 2.

5. A cultured cell containing any of the isolated nucleic acid molecules of claims 1 and 2.

6. An isolated nucleic acid molecule comprising a nucleotide sequence encoding a polypeptide wherein the amino acid sequence of the polypeptide is at least 90% identical to SEQ ID NO: 1, wherein the polypeptide binds to R13.

7. The isolated nucleic acid molecule of claim 6, wherein the amino acid sequence comprises 5,183 residues.

* * * * *

UNITED STATES PATENT AND TRADEMARK OFFICE
CERTIFICATE OF CORRECTION

PATENT NO. : 7,067,646 B2 Page 1 of 1
APPLICATION NO. : 10/107521
DATED : June 27, 2006
INVENTOR(S) : Yoshihiro Nakatani It is certified that error appears in the above-identified patent and that said Letters Patent is hereby corrected as shown below:

Column 47, Claim 2, Line 56:

Delete "polp eptide" and Insert --polypeptide--

Signed and Sealed this

Seventeenth Day of March, 2009

JOHN DOLL
*Acting Director of the United States Patent and Trademark Office*

SEQUENCE LISTING

```
<160> NUMBER OF SEQ ID NOS: 1

<210> SEQ ID NO 1
<211> LENGTH: 5183
<212> TYPE: PRT
<213> ORGANISM: Homo sapien

<400> SEQUENCE: 1

Met Ala Thr Ser Gly Gly Glu Glu Ala Ala Ala Ala Ala Pro Ala Pro
1               5                   10                  15

Gly Thr Pro Ala Thr Gly Ala Asp Thr Thr Pro Gly Trp Glu Val Ala
                20                  25                  30

Val Arg Pro Leu Leu Ser Ala Ser Tyr Ser Ala Phe Glu Met Lys Glu
            35                  40                  45

Leu Pro Gln Leu Val Ala Ser Val Ile Glu Ser Glu Ser Glu Ile Leu
        50                  55                  60

His His Glu Lys Gln Tyr Glu Pro Phe Tyr Ser Ser Phe Val Ala Leu
65                  70                  75                  80

Ser Thr His Tyr Ile Thr Thr Val Cys Ser Leu Ile Pro Arg Asn Gln
                85                  90                  95

Leu Gln Ser Val Ala Ala Cys Lys Val Leu Ile Glu Phe Ser Leu
            100                 105                 110

Leu Arg Leu Glu Asn Pro Asp Glu Ala Cys Ala Val Ser Gln Lys His
        115                 120                 125

Leu Ile Leu Leu Ile Lys Gly Leu Cys Thr Gly Cys Ser Arg Leu Asp
130                 135                 140

Arg Thr Glu Ile Ile Thr Phe Thr Ala Met Met Lys Ser Ala Lys Leu
145                 150                 155                 160

Pro Gln Thr Val Lys Thr Leu Ser Asp Val Glu Asp Gln Lys Glu Leu
                165                 170                 175

Ala Ser Pro Val Ser Pro Glu Leu Arg Gln Lys Glu Val Gln Met Asn
            180                 185                 190

Phe Leu Asn Gln Leu Thr Ser Val Phe Asn Pro Arg Thr Val Ala Ser
        195                 200                 205

Gln Pro Ile Ser Thr Gln Thr Leu Val Glu Gly Glu Asn Asp Glu Gln
    210                 215                 220

Ser Ser Thr Asp Gln Ala Ser Ala Ile Lys Thr Lys Asn Val Phe Ile
225                 230                 235                 240
```

```
Ala Gln Asn Val Ala Ser Leu Gln Glu Leu Gly Gly Ser Glu Lys Leu
            245                 250                 255
Leu Arg Val Cys Leu Asn Leu Pro Tyr Phe Leu Arg Tyr Ile Asn Arg
                260                 265                 270
Phe Gln Asp Ala Val Leu Ala Asn Ser Phe Phe Ile Met Pro Ala Thr
            275                 280                 285
Val Ala Asp Ala Thr Ala Val Arg Asn Gly Phe His Ser Leu Val Ile
        290                 295                 300
Asp Val Thr Met Ala Leu Asp Thr Leu Ser Leu Pro Val Leu Glu Pro
305                 310                 315                 320
Leu Asn Pro Ser Arg Leu Gln Asp Val Thr Val Leu Ser Leu Ser Cys
                325                 330                 335
Leu Tyr Ala Gly Val Ser Val Ala Thr Cys Met Ala Ile Leu His Val
            340                 345                 350
Gly Ser Ala Gln Gln Val Thr Arg Gly Ser Thr Ser Ser Lys Glu Asp
            355                 360                 365
Asp Tyr Glu Ser Asp Ala Ala Thr Ile Val Gln Lys Cys Leu Glu Ile
        370                 375                 380
Tyr Asp Met Ile Gly Gln Ala Ile Ser Ser Arg Arg Ala Gly Gly
385                 390                 395                 400
Glu His Tyr Gln Asn Phe Gln Leu Leu Gly Ala Trp Cys Leu Leu Asn
                405                 410                 415
Ser Leu Phe Leu Ile Leu Asn Leu Ser Pro Thr Ala Leu Ala Asp Lys
            420                 425                 430
Gly Lys Glu Lys Asp Pro Leu Ala Ala Leu Arg Val Arg Asp Ile Leu
        435                 440                 445
Ser Arg Thr Lys Glu Gly Val Gly Ser Pro Lys Leu Gly Pro Gly Lys
        450                 455                 460
Gly His Gln Gly Phe Gly Val Leu Ser Val Ile Leu Ala Asn His Ala
465                 470                 475                 480
Ile Lys Leu Leu Thr Ser Leu Phe Gln Asp Leu Gln Val Glu Ala Leu
                485                 490                 495
His Lys Gly Trp Glu Thr Asp Gly Pro Pro Ala Ala Leu Ser Ile Met
            500                 505                 510
Ala Gln Ser Thr Ser Ile Gln Arg Ile Gln Arg Leu Ile Asp Ser Val
            515                 520                 525
Pro Leu Met Asn Leu Leu Leu Thr Leu Leu Ser Thr Ser Tyr Arg Lys
        530                 535                 540
Ala Cys Val Leu Gln Arg Gln Arg Lys Gly Ser Met Ser Ser Asp Ala
545                 550                 555                 560
Ser Ala Ser Thr Asp Ser Asn Thr Tyr Tyr Glu Asp Asp Phe Ser Ser
                565                 570                 575
Thr Glu Glu Asp Ser Ser Gln Asp Asp Asp Ser Glu Pro Ile Leu Gly
            580                 585                 590
Gln Trp Phe Glu Glu Thr Ile Ser Pro Ser Lys Glu Lys Ala Ala Pro
        595                 600                 605
Pro Pro Pro Pro Pro Pro Leu Glu Ser Ser Pro Arg Val Lys
        610                 615                 620
Ser Pro Ser Lys Gln Ala Pro Glu Lys Gly Asn Ile Leu Ala Ser
625                 630                 635                 640
Arg Lys Asp Pro Glu Leu Phe Leu Gly Leu Ala Ser Asn Ile Leu Asn
                645                 650                 655
Phe Ile Thr Ser Ser Met Leu Asn Ser Arg Asn Asn Phe Ile Arg Asn
```

-continued

```
            660                 665                 670
Tyr Leu Ser Val Ser Leu Ser Glu His His Met Ala Thr Leu Ala Ser
                675                 680                 685
Ile Ile Lys Glu Val Asp Lys Asp Gly Leu Lys Gly Ser Ser Asp Glu
                690                 695                 700
Glu Phe Ala Ala Ala Leu Tyr His Phe Asn His Ser Leu Val Thr Ser
705                 710                 715                 720
Asp Leu Gln Ser Pro Asn Leu Gln Asn Thr Leu Leu Gln Gln Leu Gly
                725                 730                 735
Val Ala Pro Phe Ser Glu Gly Pro Trp Pro Leu Tyr Ile His Pro Gln
                740                 745                 750
Ser Leu Ser Val Leu Ser Arg Leu Leu Leu Ile Trp Gln His Lys Ala
                755                 760                 765
Ser Ala Gln Gly Asp Pro Asp Val Pro Glu Cys Leu Lys Val Trp Asp
                770                 775                 780
Arg Phe Leu Ser Thr Met Lys Gln Asn Ala Leu Gln Gly Val Val Pro
785                 790                 795                 800
Ser Glu Thr Glu Asp Leu Asn Val Glu His Leu Gln Met Leu Leu Leu
                805                 810                 815
Ile Phe His Asn Phe Thr Glu Thr Gly Arg Arg Ala Ile Leu Ser Leu
                820                 825                 830
Phe Val Gln Ile Ile Gln Glu Leu Ser Val Asn Met Asp Ala Gln Met
                835                 840                 845
Arg Phe Val Pro Leu Ile Leu Ala Arg Leu Leu Leu Ile Phe Asp Tyr
                850                 855                 860
Leu Leu His Gln Tyr Ser Lys Ala Pro Val Tyr Leu Phe Glu Gln Val
865                 870                 875                 880
Gln His Asn Leu Leu Ser Pro Pro Phe Gly Trp Ala Ser Gly Ser Gln
                885                 890                 895
Asp Ser Asn Ser Arg Arg Ala Thr Thr Pro Leu Tyr His Gly Phe Lys
                900                 905                 910
Glu Val Glu Glu Asn Trp Ser Lys His Phe Ser Ser Asp Ala Val Pro
                915                 920                 925
His Pro Arg Phe Tyr Cys Val Leu Ser Pro Glu Ala Ser Glu Asp Asp
                930                 935                 940
Leu Asn Arg Leu Asp Ser Val Ala Cys Asp Val Leu Phe Ser Lys Leu
945                 950                 955                 960
Val Lys Tyr Asp Glu Leu Tyr Ala Ala Leu Thr Ala Leu Leu Ala Ala
                965                 970                 975
Gly Ser Gln Leu Asp Thr Val Arg Arg Lys Glu Asn Lys Asn Val Thr
                980                 985                 990
Ala Leu Glu Ala Cys Ala Leu Gln Tyr Tyr Phe Leu Ile Leu Trp Arg
                995                 1000                1005
Ile Leu Gly Ile Leu Pro Pro Ser Lys Thr Tyr Ile Asn Gln Leu Ser
                1010                1015                1020
Met Asn Ser Pro Glu Met Ser Glu Cys Asp Ile Leu His Thr Leu Arg
1025                1030                1035                1040
Trp Ser Ser Arg Leu Arg Ile Ser Ser Tyr Val Asn Trp Ile Lys Asp
                1045                1050                1055
His Leu Ile Lys Gln Gly Met Lys Ala Glu His Ala Ser Ser Leu Leu
                1060                1065                1070
Glu Leu Ala Ser Thr Thr Lys Cys Ser Ser Val Lys Tyr Asp Val Glu
                1075                1080                1085
```

```
Ile Val Glu Glu Tyr Phe Ala Arg Gln Ile Ser Ser Phe Cys Ser Ile
    1090                1095                1100

Asp Cys Thr Thr Ile Leu Gln Leu His Glu Ile Pro Ser Leu Gln Ser
1105                1110                1115                1120

Ile Tyr Thr Leu Asp Ala Ala Ile Ser Lys Val Gln Val Ser Leu Asp
                1125                1130                1135

Glu His Phe Ser Lys Met Ala Ala Glu Thr Asp Pro His Lys Ser Ser
                1140                1145                1150

Glu Ile Thr Lys Asn Leu Leu Pro Ala Thr Leu Gln Leu Ile Asp Thr
                1155                1160                1165

Tyr Ala Ser Phe Thr Arg Ala Tyr Leu Leu Gln Asn Phe Asn Glu Glu
    1170                1175                1180

Gly Thr Thr Glu Lys Pro Ser Lys Glu Lys Leu Gln Gly Phe Ala Ala
1185                1190                1195                1200

Val Leu Ala Ile Gly Ser Ser Arg Cys Lys Ala Asn Thr Leu Gly Pro
                1205                1210                1215

Thr Leu Val Gln Asn Leu Pro Ser Ser Val Gln Thr Val Cys Glu Ser
                1220                1225                1230

Trp Asn Asn Ile Asn Thr Asn Glu Phe Pro Asn Ile Gly Ser Trp Arg
                1235                1240                1245

Asn Ala Phe Ala Asn Asp Thr Ile Pro Ser Glu Ser Tyr Ile Ser Ala
    1250                1255                1260

Val Gln Ala Ala His Leu Gly Thr Leu Cys Ser Gln Ser Leu Pro Leu
1265                1270                1275                1280

Ala Ala Ser Leu Lys His Thr Leu Leu Ser Leu Val Arg Leu Thr Gly
                1285                1290                1295

Asp Leu Ile Val Trp Ser Asp Glu Met Asn Pro Gln Val Ile Arg
                1300                1305                1310

Thr Leu Leu Pro Leu Leu Leu Glu Ser Ser Thr Glu Ser Val Ala Glu
                1315                1320                1325

Ile Ser Ser Asn Ser Leu Glu Arg Ile Leu Gly Pro Ala Glu Ser Asp
    1330                1335                1340

Glu Phe Leu Ala Arg Val Tyr Glu Lys Leu Ile Thr Gly Cys Tyr Asn
1345                1350                1355                1360

Ile Leu Ala Asn His Ala Asp Pro Asn Ser Gly Leu Asp Glu Ser Ile
                1365                1370                1375

Leu Glu Glu Cys Leu Gln Tyr Leu Glu Lys Gln Leu Glu Ser Ser Gln
                1380                1385                1390

Ala Arg Lys Ala Met Glu Glu Phe Phe Ser Asp Ser Gly Glu Leu Val
    1395                1400                1405

Gln Ile Met Met Ala Thr Ala Asn Glu Asn Leu Ser Ala Lys Phe Cys
    1410                1415                1420

Asn Arg Val Leu Lys Phe Phe Thr Lys Leu Phe Gln Leu Thr Glu Lys
1425                1430                1435                1440

Ser Pro Asn Pro Ser Leu Leu His Leu Cys Gly Ser Leu Ala Gln Leu
                1445                1450                1455

Ala Cys Val Glu Pro Val Arg Leu Gln Ala Trp Leu Thr Arg Met Thr
                1460                1465                1470

Thr Ser Pro Pro Lys Asp Ser Asp Gln Leu Asp Val Ile Gln Glu Asn
                1475                1480                1485

Arg Gln Leu Leu Gln Leu Leu Thr Thr Tyr Ile Val Arg Glu Asn Ser
    1490                1495                1500
```

```
Gln Val Gly Glu Gly Val Cys Ala Val Leu Leu Gly Thr Leu Thr Pro
1505                1510                1515                1520

Met Ala Thr Glu Met Leu Ala Asn Gly Asp Gly Thr Gly Phe Pro Glu
            1525                1530                1535

Leu Met Val Val Met Ala Thr Leu Ala Ser Ala Gly Gln Gly Ala Gly
        1540                1545                1550

His Leu Gln Leu His Asn Ala Ala Val Asp Trp Leu Ser Arg Cys Lys
    1555                1560                1565

Lys Tyr Leu Ser Gln Lys Asn Val Val Glu Lys Leu Asn Ala Asn Val
1570                1575                1580

Met His Gly Lys His Val Met Ile Leu Glu Cys Thr Cys His Ile Met
1585                1590                1595                1600

Ser Tyr Leu Ala Asp Val Thr Asn Ala Leu Ser Gln Ser Asn Gly Gln
            1605                1610                1615

Gly Pro Ser His Leu Ser Val Asp Gly Glu Glu Arg Ala Ile Glu Val
        1620                1625                1630

Asp Ser Asp Trp Val Glu Glu Leu Ala Val Glu Glu Asp Ser Gln
    1635                1640                1645

Ala Glu Asp Ser Asp Glu Asp Ser Leu Cys Asn Lys Leu Cys Thr Phe
    1650                1655                1660

Thr Ile Thr Gln Lys Glu Phe Met Asn Gln His Trp Tyr His Cys His
1665                1670                1675                1680

Thr Cys Lys Met Val Asp Gly Val Gly Val Cys Thr Val Cys Ala Lys
            1685                1690                1695

Val Cys His Lys Asp His Glu Ile Ser Tyr Ala Lys Tyr Gly Ser Phe
        1700                1705                1710

Phe Cys Asp Cys Gly Ala Lys Glu Asp Gly Ser Cys Leu Ala Leu Val
    1715                1720                1725

Lys Arg Thr Pro Ser Ser Gly Met Ser Ser Thr Met Lys Glu Ser Ala
    1730                1735                1740

Phe Gln Ser Glu Pro Arg Ile Ser Glu Ser Leu Val Arg His Ala Ser
1745                1750                1755                1760

Thr Ser Ser Pro Ala Asp Lys Ala Lys Val Thr Ile Ser Asp Gly Lys
            1765                1770                1775

Val Ala Asp Glu Glu Lys Pro Lys Lys Ser Ser Leu Cys Arg Thr Val
        1780                1785                1790

Glu Gly Cys Arg Glu Glu Leu Gln Asn Gln Ala Asn Phe Ser Phe Ala
    1795                1800                1805

Pro Leu Val Leu Asp Met Leu Asn Phe Leu Met Asp Ala Ile Gln Thr
    1810                1815                1820

Asn Phe Gln Gln Ala Ser Ala Val Gly Ser Ser Arg Ala Gln Gln
1825                1830                1835                1840

Ala Leu Ser Glu Leu His Thr Val Glu Lys Ala Val Glu Met Thr Asp
            1845                1850                1855

Gln Leu Met Val Pro Thr Leu Gly Ser Gln Glu Gly Ala Phe Glu Asn
        1860                1865                1870

Val Arg Met Asn Tyr Ser Gly Asp Gln Gly Gln Thr Ile Arg Gln Leu
    1875                1880                1885

Ile Ser Ala His Val Leu Arg Arg Val Ala Met Cys Val Leu Ser Ser
    1890                1895                1900

Pro His Gly Arg Arg Gln His Leu Ala Val Ser His Glu Lys Gly Lys
1905                1910                1915                1920

Ile Thr Val Leu Gln Leu Ser Ala Leu Leu Lys Gln Ala Asp Ser Ser
```

-continued

```
                    1925                1930                1935
Lys Arg Lys Leu Thr Leu Thr Arg Leu Ala Ser Ala Pro Val Pro Phe
                1940                1945                1950

Thr Val Leu Ser Leu Thr Gly Asn Pro Cys Lys Glu Asp Tyr Leu Ala
                1955                1960                1965

Val Cys Gly Leu Lys Asp Cys His Val Leu Thr Phe Ser Ser Ser Gly
                1970                1975                1980

Ser Val Ser Asp His Leu Val Leu His Pro Gln Leu Ala Thr Gly Asn
1985                1990                1995                2000

Phe Ile Ile Lys Ala Val Trp Leu Pro Gly Ser Gln Thr Glu Leu Ser
                2005                2010                2015

Ile Val Thr Ala Asp Phe Val Lys Ile Tyr Asp Leu Cys Val Asp Ala
                2020                2025                2030

Leu Ser Pro Thr Phe Tyr Phe Leu Pro Ser Ser Lys Ile Arg Asp
                2035                2040                2045

Val Thr Phe Leu Phe Asn Glu Glu Gly Lys Asn Ile Ile Val Ile Met
                2050                2055                2060

Ser Ser Ala Gly Tyr Ile Tyr Thr Gln Leu Met Glu Glu Ala Ser Ser
2065                2070                2075                2080

Ala Gln Gln Gly Pro Phe Tyr Val Thr Asn Val Leu Glu Ile Asn His
                2085                2090                2095

Glu Asp Leu Lys Asp Ser Asn Ser Gln Val Ala Gly Gly Val Ser
                2100                2105                2110

Val Tyr Tyr Ser His Val Leu Gln Met Leu Phe Phe Ser Tyr Cys Gln
                2115                2120                2125

Gly Lys Ser Phe Ala Ala Thr Ile Ser Arg Thr Thr Leu Glu Val Leu
                2130                2135                2140

Gln Leu Phe Pro Ile Asn Ile Lys Ser Ser Asn Gly Gly Ser Lys Thr
2145                2150                2155                2160

Ser Pro Ala Leu Cys Gln Trp Ser Glu Val Met Asn His Pro Gly Leu
                2165                2170                2175

Val Cys Cys Val Gln Gln Thr Thr Gly Val Pro Leu Val Val Met Val
                2180                2185                2190

Lys Pro Asp Thr Phe Leu Ile Gln Glu Ile Lys Thr Leu Pro Ala Lys
                2195                2200                2205

Ala Lys Ile Gln Asp Met Val Ala Ile Arg His Thr Ala Cys Asn Glu
                2210                2215                2220

Gln Gln Arg Thr Thr Met Ile Leu Leu Cys Glu Asp Gly Ser Leu Arg
2225                2230                2235                2240

Ile Tyr Met Ala Asn Val Glu Asn Thr Ser Tyr Trp Leu Gln Pro Ser
                2245                2250                2255

Leu Gln Pro Ser Ser Val Ile Ser Ile Met Lys Pro Val Arg Lys Arg
                2260                2265                2270

Lys Thr Ala Thr Ile Thr Thr Arg Thr Ser Ser Gln Val Thr Phe Pro
                2275                2280                2285

Ile Asp Phe Phe Glu His Asn Gln Gln Leu Thr Asp Val Glu Phe Gly
                2290                2295                2300

Gly Asn Asp Leu Leu Gln Val Tyr Asn Ala Gln Gln Ile Lys His Arg
2305                2310                2315                2320

Leu Asn Ser Thr Gly Met Tyr Val Ala Asn Thr Lys Pro Gly Gly Phe
                2325                2330                2335

Thr Ile Glu Ile Ser Asn Asn Asn Ser Thr Met Val Met Thr Gly Met
                2340                2345                2350
```

-continued

```
Arg Ile Gln Ile Gly Thr Gln Ala Ile Glu Arg Ala Pro Ser Tyr Ile
        2355                2360                2365
Glu Ile Phe Gly Arg Thr Met Gln Leu Asn Leu Ser Arg Ser Arg Trp
    2370                2375                2380
Phe Asp Phe Pro Phe Thr Arg Glu Glu Ala Leu Gln Ala Asp Lys Lys
2385                2390                2395                2400
Leu Asn Leu Phe Ile Gly Ala Ser Val Glu Pro Ala Gly Val Thr Met
            2405                2410                2415
Ile Asp Ala Val Lys Ile Tyr Gly Lys Thr Lys Glu Gln Phe Gly Trp
        2420                2425                2430
Pro Asp Glu Pro Pro Glu Glu Phe Pro Ser Ala Ser Val Ser Asn Ile
    2435                2440                2445
Cys Pro Ser Asn Leu Asn Gln Ser Asn Gly Thr Gly Asp Ser Asp Ser
        2450                2455                2460
Ala Ala Pro Thr Thr Thr Ser Gly Thr Val Leu Glu Arg Leu Val Val
2465                2470                2475                2480
Ser Ser Leu Glu Ala Leu Glu Ser Cys Phe Ala Val Gly Pro Ile Ile
            2485                2490                2495
Glu Lys Glu Arg Asn Lys Asn Ala Ala Gln Glu Leu Ala Thr Leu Leu
        2500                2505                2510
Leu Ser Leu Pro Ala Pro Ala Ser Val Gln Gln Gln Ser Lys Ser Leu
    2515                2520                2525
Leu Ala Ser Leu His Thr Ser Arg Ser Ala Tyr His Ser His Lys Asp
        2530                2535                2540
Gln Ala Leu Leu Ser Lys Ala Val Gln Cys Leu Asn Thr Ser Ser Lys
2545                2550                2555                2560
Glu Gly Lys Asp Leu Asp Pro Glu Val Phe Gln Arg Leu Val Ile Thr
            2565                2570                2575
Ala Arg Ser Ile Ala Ile Met Arg Pro Asn Asn Leu Val His Phe Thr
        2580                2585                2590
Glu Ser Lys Leu Pro Gln Met Glu Thr Glu Gly Met Asp Glu Gly Lys
    2595                2600                2605
Glu Pro Gln Lys Gln Leu Glu Gly Asp Cys Cys Ser Phe Ile Thr Gln
        2610                2615                2620
Leu Val Asn His Phe Trp Lys Leu His Ala Ser Lys Pro Lys Asn Ala
2625                2630                2635                2640
Phe Leu Ala Pro Ala Cys Leu Pro Gly Leu Thr His Ile Glu Ala Thr
            2645                2650                2655
Val Asn Ala Leu Val Asp Ile Ile His Gly Tyr Cys Thr Cys Glu Leu
        2660                2665                2670
Asp Cys Ile Asn Thr Ala Ser Lys Ile Tyr Met Gln Met Leu Leu Cys
        2675                2680                2685
Pro Asp Pro Ala Val Ser Phe Ser Cys Lys Gln Ala Leu Ile Arg Val
    2690                2695                2700
Leu Arg Pro Arg Asn Lys Arg His Val Thr Leu Pro Ser Ser Pro
2705                2710                2715                2720
Arg Ser Asn Thr Pro Met Gly Asp Lys Asp Asp Asp Asp Asp Asp
            2725                2730                2735
Ala Asp Glu Lys Met Gln Ser Ser Gly Ile Pro Asn Gly Gly His Ile
        2740                2745                2750
Arg Gln Glu Ser Gln Glu Gln Ser Glu Val Asp His Gly Asp Phe Glu
        2755                2760                2765
```

```
Met Val Ser Glu Ser Met Val Leu Glu Thr Ala Glu Asn Val Asn Asn
    2770            2775            2780

Gly Asn Pro Ser Pro Leu Glu Ala Leu Leu Ala Gly Ala Glu Gly Phe
2785            2790            2795            2800

Pro Pro Met Leu Asp Ile Pro Pro Asp Ala Asp Asp Glu Thr Met Val
        2805            2810            2815

Glu Leu Ala Ile Ala Leu Ser Leu Gln Gln Asp Gln Gln Gly Ser Ser
        2820            2825            2830

Ser Ser Ala Leu Gly Leu Gln Ser Leu Gly Leu Ser Gly Gln Ala Pro
        2835            2840            2845

Ser Ser Ser Ser Leu Asp Ala Gly Thr Leu Ser Asp Thr Thr Ala Ser
    2850            2855            2860

Ala Pro Ala Ser Asp Asp Glu Gly Ser Thr Ala Ala Thr Asp Gly Ser
2865            2870            2875            2880

Thr Leu Arg Thr Ser Pro Ala Asp His Gly Gly Ser Val Gly Ser Glu
            2885            2890            2895

Ser Gly Gly Ser Ala Val Asp Ser Val Ala Gly Glu His Ser Val Ser
            2900            2905            2910

Gly Arg Ser Ser Ala Tyr Gly Asp Ala Thr Ala Glu Gly His Pro Ala
    2915            2920            2925

Gly Pro Gly Ser Val Ser Ser Ser Thr Gly Ala Ile Ser Thr Thr Thr
    2930            2935            2940

Gly His Gln Glu Gly Asp Gly Ser Glu Gly Glu Gly Glu Gly Glu Thr
2945            2950            2955            2960

Glu Gly Asp Val His Thr Ser Asn Arg Leu His Met Val Arg Leu Met
            2965            2970            2975

Leu Leu Glu Arg Leu Leu Gln Thr Leu Pro Gln Leu Arg Asn Val Gly
        2980            2985            2990

Gly Val Arg Ala Ile Pro Tyr Met Gln Val Ile Leu Met Leu Thr Thr
        2995            3000            3005

Asp Leu Asp Gly Glu Asp Glu Lys Asp Lys Gly Ala Leu Asp Asn Leu
    3010            3015            3020

Leu Ser Gln Leu Ile Ala Glu Leu Gly Met Asp Lys Lys Asp Val Ser
3025            3030            3035            3040

Lys Lys Asn Glu Arg Ser Ala Leu Asn Glu Val His Leu Val Val Met
            3045            3050            3055

Arg Leu Leu Ser Val Phe Met Ser Arg Thr Lys Ser Gly Ser Lys Ser
            3060            3065            3070

Ser Ile Cys Glu Ser Ser Ser Leu Ile Ser Ser Ala Thr Ala Ala Ala
            3075            3080            3085

Leu Leu Ser Ser Gly Ala Val Asp Tyr Cys Leu His Val Leu Lys Ser
        3090            3095            3100

Leu Leu Glu Tyr Trp Lys Ser Gln Gln Asn Asp Glu Glu Pro Val Ala
3105            3110            3115            3120

Thr Ser Gln Leu Leu Lys Pro His Thr Thr Ser Ser Pro Pro Asp Met
            3125            3130            3135

Ser Pro Phe Phe Leu Arg Gln Tyr Val Lys Gly His Ala Ala Asp Val
        3140            3145            3150

Phe Glu Ala Tyr Thr Gln Leu Leu Thr Glu Met Val Leu Arg Leu Pro
        3155            3160            3165

Tyr Gln Ile Lys Lys Ile Thr Asp Thr Asn Ser Arg Ile Pro Pro Pro
    3170            3175            3180

Val Phe Asp His Ser Trp Phe Tyr Phe Leu Ser Glu Tyr Leu Met Ile
```

-continued

```
              3185                3190                3195                3200
Gln Gln Thr Pro Phe Val Arg Arg Gln Val Arg Lys Leu Leu Leu Phe
              3205                3210                3215
Ile Cys Gly Ser Lys Glu Lys Tyr Arg Gln Leu Arg Asp Leu His Thr
              3220                3225                3230
Leu Asp Ser His Val Arg Gly Ile Lys Lys Leu Leu Glu Glu Gln Gly
              3235                3240                3245
Ile Phe Leu Arg Ala Ser Val Val Thr Ala Ser Ser Gly Ser Ala Leu
              3250                3255                3260
Gln Tyr Asp Thr Leu Ile Ser Leu Met Glu His Leu Lys Ala Cys Ala
3265                3270                3275                3280
Glu Ile Ala Ala Gln Arg Thr Ile Asn Trp Gln Lys Phe Cys Ile Lys
              3285                3290                3295
Asp Asp Ser Val Leu Tyr Phe Leu Leu Gln Val Ser Phe Leu Val Asp
              3300                3305                3310
Glu Gly Val Ser Pro Val Leu Leu Gln Leu Leu Ser Cys Ala Leu Cys
              3315                3320                3325
Gly Ser Lys Val Leu Ala Ala Leu Ala Ala Ser Ser Gly Ser Ser Ser
              3330                3335                3340
Ala Ser Ser Ser Ala Pro Val Ala Ala Ser Ser Gly Gln Ala Thr
3345                3350                3355                3360
Thr Gln Ser Lys Ser Ser Thr Lys Lys Ser Lys Lys Glu Glu Lys Glu
              3365                3370                3375
Lys Glu Lys Asp Gly Glu Thr Ser Gly Ser Gln Glu Asp Gln Leu Cys
              3380                3385                3390
Thr Ala Leu Val Asn Gln Leu Asn Lys Phe Ala Asp Lys Glu Thr Leu
              3395                3400                3405
Ile Gln Phe Leu Arg Cys Phe Leu Leu Glu Ser Asn Ser Ser Ser Val
              3410                3415                3420
Arg Trp Gln Ala His Cys Leu Thr Leu His Ile Tyr Arg Asn Ser Ser
3425                3430                3435                3440
Lys Ser Gln Gln Glu Leu Leu Leu Asp Leu Met Trp Ser Ile Trp Pro
              3445                3450                3455
Glu Leu Pro Ala Tyr Gly Arg Lys Ala Ala Gln Phe Val Asp Leu Leu
              3460                3465                3470
Gly Tyr Phe Ser Leu Lys Thr Pro Gln Thr Glu Lys Lys Leu Lys Glu
              3475                3480                3485
Tyr Ser Gln Lys Ala Val Glu Ile Leu Arg Thr Gln Asn His Ile Leu
              3490                3495                3500
Thr Asn His Pro Asn Ser Asn Ile Tyr Asn Thr Leu Ser Gly Leu Val
3505                3510                3515                3520
Glu Phe Asp Gly Tyr Tyr Leu Glu Ser Asp Pro Cys Leu Val Cys Asn
              3525                3530                3535
Asn Pro Glu Val Pro Phe Cys Tyr Ile Lys Leu Ser Ser Ile Lys Val
              3540                3545                3550
Asp Thr Arg Tyr Thr Thr Thr Gln Gln Val Val Lys Leu Ile Gly Ser
              3555                3560                3565
His Thr Ile Ser Lys Val Thr Val Lys Ile Gly Asp Leu Lys Arg Thr
              3570                3575                3580
Lys Met Val Arg Thr Ile Asn Leu Tyr Tyr Asn Asn Arg Thr Val Gln
3585                3590                3595                3600
Ala Ile Val Glu Leu Lys Asn Lys Pro Ala Arg Trp His Lys Ala Lys
              3605                3610                3615
```

```
Lys Val Gln Leu Thr Pro Gly Gln Thr Glu Val Lys Ile Asp Leu Pro
            3620                3625                3630

Leu Pro Ile Val Ala Ser Asn Leu Met Ile Glu Phe Ala Asp Phe Tyr
            3635                3640                3645

Glu Asn Tyr Gln Ala Ser Thr Glu Thr Leu Gln Cys Pro Arg Cys Ser
            3650                3655                3660

Ala Ser Val Pro Ala Asn Pro Gly Val Cys Gly Asn Cys Gly Glu Asn
3665                3670                3675                3680

Val Tyr Gln Cys His Lys Cys Arg Ser Ile Asn Tyr Asp Glu Lys Asp
            3685                3690                3695

Pro Phe Leu Cys Asn Ala Cys Gly Phe Cys Lys Tyr Ala Arg Phe Asp
            3700                3705                3710

Phe Met Leu Tyr Ala Lys Pro Cys Cys Ala Val Asp Pro Ile Glu Asn
            3715                3720                3725

Glu Glu Asp Arg Lys Lys Ala Val Ser Asn Ile Asn Thr Leu Leu Asp
            3730                3735                3740

Lys Ala Asp Arg Val Tyr His Gln Leu Met Gly His Arg Pro Gln Leu
3745                3750                3755                3760

Glu Asn Leu Leu Cys Lys Val Asn Glu Ala Ala Pro Glu Lys Pro Gln
            3765                3770                3775

Asp Asp Ser Gly Thr Ala Gly Gly Ile Ser Ser Thr Ala Ser Val
            3780                3785                3790

Asn Arg Tyr Ile Leu Gln Leu Ala Gln Glu Tyr Cys Gly Asp Cys Lys
            3795                3800                3805

Asn Ser Phe Asp Glu Leu Ser Lys Ile Ile Gln Lys Val Phe Ala Ser
            3810                3815                3820

Arg Lys Glu Leu Leu Glu Tyr Asp Leu Gln Gln Arg Glu Ala Ala Thr
3825                3830                3835                3840

Lys Ser Ser Arg Thr Ser Val Gln Pro Thr Phe Thr Ala Ser Gln Tyr
            3845                3850                3855

Arg Ala Leu Ser Val Leu Gly Cys Gly His Thr Ser Ser Thr Lys Cys
            3860                3865                3870

Tyr Gly Cys Ala Ser Ala Val Thr Glu His Cys Ile Thr Leu Leu Arg
            3875                3880                3885

Ala Leu Ala Thr Asn Pro Ala Leu Arg His Ile Leu Val Ser Gln Gly
            3890                3895                3900

Leu Ile Arg Glu Leu Phe Asp Tyr Asn Leu Arg Arg Gly Ala Ala Ala
3905                3910                3915                3920

Met Arg Glu Glu Val Arg Gln Leu Met Cys Leu Leu Thr Arg Asp Asn
            3925                3930                3935

Pro Glu Ala Thr Gln Gln Met Asn Asp Leu Ile Ile Gly Lys Val Ser
            3940                3945                3950

Thr Ala Leu Lys Ser His Trp Ala Asn Pro Asp Leu Ala Ser Ser Leu
            3955                3960                3965

Gln Tyr Glu Met Leu Leu Thr Asp Ser Ile Ser Lys Glu Asp Ser
            3970                3975                3980

Cys Trp Glu Leu Arg Leu Arg Cys Ala Leu Ser Leu Phe Leu Met Ala
3985                3990                3995                4000

Val Asn Ile Lys Thr Pro Val Val Glu Asn Ile Thr Leu Met Cys
            4005                4010                4015

Leu Arg Ile Leu Gln Lys Leu Ile Lys Pro Pro Ala Pro Thr Ser Lys
            4020                4025                4030
```

-continued

Lys Asn Lys Asp Val Pro Val Glu Ala Leu Thr Thr Val Lys Pro Tyr
    4035                4040                4045

Cys Asn Glu Ile His Ala Gln Ala Gln Leu Trp Leu Lys Arg Asp Pro
    4050                4055                4060

Lys Ala Ser Tyr Asp Ala Trp Lys Lys Cys Leu Pro Ile Arg Gly Ile
4065                4070                4075                4080

Asp Gly Asn Gly Lys Ala Pro Ser Lys Ser Glu Leu Arg His Leu Tyr
                4085                4090                4095

Leu Thr Glu Lys Tyr Val Trp Arg Trp Lys Gln Phe Leu Ser Arg Arg
            4100                4105                4110

Gly Lys Arg Thr Ser Pro Leu Asp Leu Lys Leu Gly His Asn Asn Trp
        4115                4120                4125

Leu Arg Gln Val Leu Phe Thr Pro Ala Thr Gln Ala Ala Arg Gln Ala
    4130                4135                4140

Ala Cys Thr Ile Val Glu Ala Leu Ala Thr Ile Pro Ser Arg Lys Gln
4145                4150                4155                4160

Gln Val Leu Asp Leu Leu Thr Ser Tyr Leu Asp Glu Leu Ser Ile Ala
                4165                4170                4175

Gly Glu Cys Ala Ala Glu Tyr Leu Ala Leu Tyr Gln Lys Leu Ile Thr
            4180                4185                4190

Ser Ala His Trp Lys Val Tyr Leu Ala Ala Arg Gly Val Leu Pro Tyr
        4195                4200                4205

Val Gly Asn Leu Ile Thr Lys Glu Ile Ala Arg Leu Leu Ala Leu Glu
    4210                4215                4220

Glu Ala Thr Leu Ser Thr Asp Leu Gln Gln Gly Tyr Ala Leu Lys Ser
4225                4230                4235                4240

Leu Thr Gly Leu Leu Ser Ser Phe Val Glu Val Glu Ser Ile Lys Arg
                4245                4250                4255

His Phe Lys Ser Arg Leu Val Gly Thr Val Leu Asn Gly Tyr Leu Cys
            4260                4265                4270

Leu Arg Lys Leu Val Val Gln Arg Thr Lys Leu Ile Asp Glu Thr Gln
        4275                4280                4285

Asp Met Leu Leu Glu Met Leu Glu Asp Met Thr Thr Gly Thr Glu Ser
    4290                4295                4300

Glu Thr Lys Ala Phe Met Ala Val Cys Ile Glu Thr Ala Lys Arg Tyr
4305                4310                4315                4320

Asn Leu Asp Asp Tyr Arg Thr Pro Val Phe Ile Phe Glu Arg Leu Cys
                4325                4330                4335

Ser Ile Ile Tyr Pro Glu Glu Asn Glu Val Thr Glu Phe Phe Val Thr
            4340                4345                4350

Leu Glu Lys Asp Pro Gln Gln Glu Asp Phe Leu Gln Gly Arg Met Pro
        4355                4360                4365

Gly Asn Pro Tyr Ser Ser Asn Glu Pro Gly Ile Gly Pro Leu Met Arg
    4370                4375                4380

Asp Ile Lys Asn Lys Ile Cys Gln Asp Cys Asp Leu Val Ala Leu Leu
4385                4390                4395                4400

Glu Asp Asp Ser Gly Met Glu Leu Leu Val Asn Asn Lys Ile Ile Ser
                4405                4410                4415

Leu Asp Leu Pro Val Ala Glu Val Tyr Lys Lys Val Trp Cys Thr Thr
            4420                4425                4430

Asn Glu Gly Glu Pro Met Arg Ile Val Tyr Arg Met Arg Gly Leu Leu
        4435                4440                4445

Gly Asp Ala Thr Glu Glu Phe Ile Glu Ser Leu Asp Ser Thr Thr Asp

-continued

```
        4450                4455                4460
Glu Glu Glu Asp Glu Glu Val Tyr Lys Met Ala Gly Val Met Ala
4465                4470                4475                4480

Gln Cys Gly Gly Leu Glu Cys Met Leu Asn Arg Leu Ala Gly Ile Arg
            4485                4490                4495

Asp Phe Lys Gln Gly Arg His Leu Leu Thr Val Leu Lys Leu Phe
        4500                4505                4510

Ser Tyr Cys Val Lys Val Lys Val Asn Arg Gln Gln Leu Val Lys Leu
        4515                4520                4525

Glu Met Asn Thr Leu Asn Val Met Leu Gly Thr Leu Asn Leu Ala Leu
        4530                4535                4540

Val Ala Glu Gln Glu Ser Lys Asp Ser Gly Ala Ala Val Ala Glu
4545                4550                4555                4560

Gln Val Leu Ser Ile Met Glu Ile Ile Leu Asp Glu Ser Asn Ala Glu
            4565                4570                4575

Pro Leu Ser Glu Asp Lys Gly Asn Leu Leu Thr Gly Asp Lys Asp
        4580                4585                4590

Gln Leu Val Met Leu Leu Asp Gln Ile Asn Ser Thr Phe Val Arg Ser
        4595                4600                4605

Asn Pro Ser Val Leu Gln Gly Leu Leu Arg Ile Ile Pro Tyr Leu Ser
4610                4615                4620

Phe Gly Glu Val Glu Lys Met Gln Ile Leu Val Glu Arg Phe Lys Pro
4625                4630                4635                4640

Tyr Cys Asn Phe Asp Lys Tyr Asp Glu Asp His Ser Gly Asp Lys
            4645                4650                4655

Val Phe Leu Asp Cys Phe Cys Lys Ile Ala Ala Gly Ile Lys Asn Asn
        4660                4665                4670

Ser Asn Gly His Gln Leu Lys Asp Leu Ile Leu Gln Lys Gly Ile Thr
            4675                4680                4685

Gln Asn Ala Leu Asp Tyr Met Lys Lys His Ile Pro Ser Ala Lys Asn
        4690                4695                4700

Leu Asp Ala Asp Ile Trp Lys Lys Phe Leu Ser Arg Pro Ala Leu Pro
4705                4710                4715                4720

Phe Ile Leu Arg Leu Leu Arg Gly Leu Ala Ile Gln His Pro Gly Thr
            4725                4730                4735

Gln Val Leu Ile Gly Thr Asp Ser Ile Pro Asn Leu His Lys Leu Glu
            4740                4745                4750

Gln Val Ser Ser Asp Glu Gly Ile Gly Thr Leu Ala Glu Asn Leu Leu
        4755                4760                4765

Glu Ala Leu Arg Glu His Pro Asp Val Asn Lys Lys Ile Asp Ala Ala
        4770                4775                4780

Arg Arg Glu Thr Arg Ala Glu Lys Lys Arg Met Ala Met Ala Met Arg
4785                4790                4795                4800

Gln Lys Ala Leu Gly Thr Leu Gly Met Thr Thr Asn Glu Lys Gly Gln
            4805                4810                4815

Val Val Thr Lys Thr Ala Leu Leu Lys Gln Met Glu Glu Leu Ile Glu
            4820                4825                4830

Glu Pro Gly Leu Thr Cys Cys Ile Cys Arg Glu Gly Tyr Lys Phe Gln
        4835                4840                4845

Pro Thr Lys Val Leu Gly Ile Tyr Thr Phe Ile Lys Arg Val Ala Leu
        4850                4855                4860

Glu Glu Met Glu Asn Lys Pro Arg Lys Gln Gln Gly Tyr Ser Thr Val
4865                4870                4875                4880
```

```
Ser His Phe Asn Ile Val His Tyr Asp Cys His Leu Ala Ala Val Arg
            4885            4890                    4895

Leu Ala Arg Gly Arg Glu Glu Trp Glu Ser Ala Ala Leu Gln Asn Ala
            4900            4905                    4910

Asn Thr Lys Cys Asn Gly Leu Leu Pro Val Trp Gly Pro His Val Pro
            4915            4920                    4925

Glu Ser Ala Phe Ala Thr Cys Leu Ala Arg His Asn Thr Tyr Leu Gln
            4930            4935                    4940

Glu Cys Thr Gly Gln Arg Glu Pro Thr Tyr Gln Leu Asn Ile His Asp
4945            4950            4955                    4960

Ile Lys Leu Leu Phe Leu Arg Phe Ala Met Glu Gln Ser Phe Ser Ala
            4965            4970                    4975

Asp Thr Gly Gly Gly Arg Glu Ser Asn Ile His Leu Ile Pro Tyr
            4980            4985                    4990

Ile Ile His Thr Val Leu Tyr Val Leu Asn Thr Thr Arg Ala Thr Ser
            4995            5000                    5005

Arg Glu Glu Lys Asn Leu Gln Gly Phe Leu Gln Pro Lys Glu Lys
            5010            5015                    5020

Trp Val Glu Ser Ala Phe Glu Val Asp Gly Pro Tyr Tyr Phe Thr Val
5025            5030            5035                    5040

Leu Ala Leu His Ile Leu Pro Pro Glu Gln Trp Arg Ala Thr Arg Val
            5045            5050                    5055

Glu Ile Leu Arg Arg Leu Leu Val Thr Ser Gln Ala Arg Ala Val Ala
            5060            5065                    5070

Pro Gly Gly Ala Thr Arg Leu Thr Asp Lys Ala Val Lys Asp Tyr Ser
            5075            5080                    5085

Ala Tyr Arg Ser Ser Leu Leu Phe Trp Ala Leu Val Asp Leu Ile Tyr
            5090            5095            5100

Asn Met Phe Lys Lys Val Pro Thr Ser Asn Thr Glu Gly Gly Trp Ser
5105            5110            5115                    5120

Cys Ser Leu Ala Glu Tyr Ile Arg His Asn Asp Met Pro Ile Tyr Glu
            5125            5130                    5135

Ala Ala Asp Lys Ala Leu Lys Thr Phe Gln Glu Glu Phe Met Pro Val
            5140            5145                    5150

Glu Thr Phe Ser Glu Phe Leu Asp Val Ala Gly Leu Leu Ser Glu Ile
            5155            5160            5165

Thr Asp Pro Glu Ser Phe Leu Lys Asp Leu Leu Asn Ser Val Pro
            5170            5175            5180
```